(12) United States Patent
Bolli et al.

(10) Patent No.: US 8,003,800 B2
(45) Date of Patent: Aug. 23, 2011

(54) THIOPHENE DERIVATIVES AS S1P1/EDG1 RECEPTOR AGONISTS

(75) Inventors: Martin Bolli, Allschwil (CH); David Lehmann, Basel (CH); Boris Mathys, Pratteln (CH); Claus Mueller, Weil Am Rhein (DE); Oliver Nayler, Arlesheim (CH); Beat Steiner, Battwil (CH); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 370 days.

(21) Appl. No.: 12/160,520

(22) PCT Filed: Jan. 10, 2007

(86) PCT No.: PCT/IB2007/050070
§ 371 (c)(1), (2), (4) Date: Jul. 10, 2008

(87) PCT Pub. No.: WO2007/080542
PCT Pub. Date: Jul. 19, 2007

(65) Prior Publication Data
US 2010/0240717 A1     Sep. 23, 2010

(30) Foreign Application Priority Data
Jan. 11, 2006  (WO) .................. PCT/IB2006/050103

(51) Int. Cl.
C07D 271/06      (2006.01)
(52) U.S. Cl. ........................... 548/131; 548/143; 549/60
(58) Field of Classification Search ............... 549/60; 548/131, 143
See application file for complete search history.

(56) References Cited

U.S. PATENT DOCUMENTS

| | | | |
|---|---|---|---|
| 7,605,269 B2 | 10/2009 | Bolli et al. | |
| 7,723,378 B2 | 5/2010 | Bolli et al. | |
| 7,750,040 B2 | 7/2010 | Bolli et al. | |
| 7,846,964 B2 | 12/2010 | Bolli et al. | |
| 2007/0043014 A1 * | 2/2007 | Doherty et al. | 514/210.2 |
| 2010/0075946 A1 | 3/2010 | Bolli et al. | |
| 2010/0261702 A1 | 10/2010 | Bolli et al. | |

FOREIGN PATENT DOCUMENTS

| | | |
|---|---|---|
| WO | WO-91/15583 A1 | 10/1991 |
| WO | WO-99/46277 A1 | 9/1999 |
| WO | WO-03/062248 A2 | 7/2003 |
| WO | WO 03/062252 | 7/2003 |
| WO | WO 03/105771 | 12/2003 |
| WO | WO-2004/035538 A1 | 4/2004 |
| WO | WO 2004/103279 | 12/2004 |
| WO | WO-2005/014525 A2 | 2/2005 |
| WO | WO 2005/032465 * | 4/2005 |
| WO | WO-2005/032465 A2 | 4/2005 |
| WO | WO-2005/058848 A1 | 6/2005 |
| WO | WO-2006/131336 A1 | 12/2006 |
| WO | WO-2006/137019 A1 | 12/2006 |
| WO | WO-2007/085451 A2 | 8/2007 |
| WO | WO-2008/076356 A1 | 6/2008 |
| WO | WO-2008/091967 A1 | 7/2008 |

OTHER PUBLICATIONS

Sausville et al.(Cancer Res. 2006; 66 (7): 3351-3354).*
Lens (Br. J. Nurs., 2008, vol. 17, No. 5, pp. 300-305).*
Divers et al. (Cutis. 2004, vol. 73, No. 4, pp. 257-262).*
Hla, Timothy et al.; "An Abundant Transcript Induced in Differentiating Human Endothelial Cells Encodes a Polypeptide with Structural Similarities to G-protein-coupled Receptors"; The Journal of Biological Chemistry, vol. 265, No. 16, Issue of Jun. 5, 1990, pp. 9308-9313.
Gould, Philip L.; "Salt selection for basic drugs"; International Journal of Pharmaceutics, 33 (1986), pp. 201-217.
Gibson, Mark, Editor, Pharmaceutical Preformulation and Formulation, IHS Health Group, Englewood, CO, USA, 2001.
Mentzel, M. et al.; "$N$-Methoxy-$N$-methylamides (Weinreb Amides) in Modern Organic Synthesis"; Journal fuer praktische Chemie Chemiker-Zeitung 339, 1997, pp. 517-524.
Singh, Jaimala et al. ; "The Growing Synthetic Utility of Weinreb's Amide"; Journal fuer Praktische Chemie (Weinheim, Germany), 342, No. 4, 2000, pp. 340-347.
Khlestkin, Vadim, K. et al.; "Recent Advances in the Application of N,O-Dialkylhydroxylamines in Organic Chemisry"; Current Organic Chemistry, 2003, 7, pp. 967-993.
Gangloff, Anthony R. et al.; "Synthesis of 3,5-disubstituted-1,2,4-oxadiazoles using tetrabutylammonium fluoride as a mild and efficient catalyst"; Tetrahedron Letters 42, (2001), pp. 1441-1443.
Suzuki, Takeshi et al.; "Synthesis of the Selective 5-Hydroxytryptamine 4 (5-HT$_4$) Receptor Agonist (+)-($S$)-2-Chloro-5-methoxy-4-[5-(2-piperidylmethyl)-1,2,4-oxadiazol-3yl]aniline"; Chem. Pharm. Bull., vol. 47, No. 1, 1999, pp. 120-122.
Poulain, Rebecca F. et al.; "Parallel synthesis of 1,2,4-oxadiazoles from carboxylic acids using an improved, uronium-based, activation"; Tetrahedron Letters 42 (2001), pp. 1495-1498.

(Continued)

*Primary Examiner* — Yong Chu
*Assistant Examiner* — Valerie Rodriguez-Garcia
(74) *Attorney, Agent, or Firm* — Hoxie & Associates LLC

(57) ABSTRACT

The invention relates to thiophene derivatives of formula (I)/their preparation and their use as pharmaceutically active compounds. Said compounds particularly act as immunosuppressive agents wherein: A represents *—CO—CH=CH—, *—CO—CH$_2$CH$_2$—, *—CO—CH$_2$—NH—, wherein the asterisks indicate the bond that is linked to the thiophene group of Formula (I), and R1-R3 are as defined in the claims.

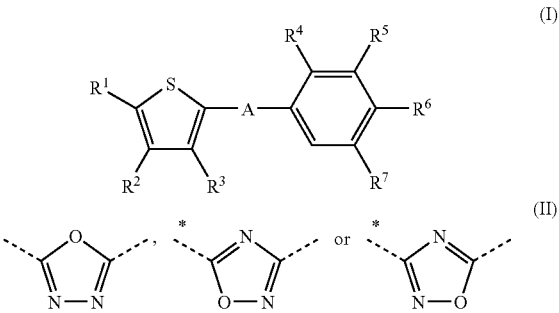

29 Claims, No Drawings

OTHER PUBLICATIONS

Srivastava, R.M. et al.; "Synthesis of 3-Aryl-5-[Thien-3-Yl Methyl]-1,2,4-Oxadiazoles"; Synthetic Communications, 29(9), 1999, pp. 1437-1450.

John, Earnest Obed et al; "Reactions of (Difluoroamino) difluoroacetonitrile and (Difluoroamino) difluoroacetamidoxime"; Inorganic Chemistry, vol. 27, No. 18, 1988, pp. 3100-3104.

Kaboudin, Babak et al.; "One-Pot Synthesis of 1,2,4-Oxadiazoles Mediated by Microwave Irradiation Under Solvent-Free Condition"; Heterocycles, vol. 60, No. 10, 2003, pp. 2287-2292.

Hamze, Abdallah et al.; "Synthesis of Various 3-Substituted 1,2,4-Oxadiazole-Containing Chiral $\beta^3$-and$\alpha$-Amino Acids from Fmoc-Protected Aspartic Acid"; J. Org. Chem., vol. 68, No. 19, 2003, pp. 7316-7321.

Brian, Christopher T. et al.; "Novel procedure for the synthesis of 1,3,4-oxadiazoles from 1,2-diacylhydrazines using polymer-supported Burgess reagent under microwave conditions"; Tetrahedron Letters 40, 1999, pp. 3275-3278.

Cui, Jian et al.; "Design and Synthesis of Highly Constrained Factor Xa Inhibitors: Amidine-Substituted Bis(benzoyl)-[1,3]-diazepan-2-ones and Bis(benzylidene)-bis(gem-dimethyl)cycloketones"; Bioorganic & Medicinal Chemistry 11, 2003, pp. 3379-3392.

Greene, Theodora W. et al.; Protective Groups in Organic Synthesis, 3rd Edition, Wiley, New York, 1991.

Kocienski, Phillip J.; Protecting Groups, Foundations of Organic Chemistry Series, Thieme Stuttgart, 1994.

Mewshaw, Richard E.; "Vilsmeier Reagents: Preparation of $\beta$-HALO-$\alpha,\beta$-Unsaturated Ketones"; Tetrahedron Letters, vol. 30, No. 29, 1989, pp. 3753-3756.

Lakhvich, F. A. et al.; "Zhurnal Organicheskoi Khimii"; 1989, pp. 2541-2549.

Popov, Sergey A. et al.; "Synthesis of 2-Alkyl and 2-Aryl Pyrimidines From $\beta$-Chlorovinyl Ketones of Cyclopentanone Type"; Synthetic Communications, 31(2), 2001, pp. 233-243.

Chrisp, Geoffrey T. et al.; "Palladium-Catalyzed, Carbonylative, Intramolecular Coupling of Hydroxy Vinyl Triflates. Synthesis of Substituted $\alpha\beta$-Butenolides"; J. Org. Chem., vol. 57, 1992, pp. 6972-6975.

Keenan, R. M. et al.; "Imidazole-5-acrylic Acids: Potent Nonpeptide Angiotensin II Receptor Antagonists Designed Using a Novel Peptide Pharmacophore Model[1]"; Journal of Medicinal Chemistry, vol. 35, No. 21, 1992, pp. 3858-3872.

Kashima, Choji et al.; "Preparation of 2,6-Bis(l-menthopyrzol-3-yl)pyridines and their Catalytic Activity for Asymmetric Diels Alder Reaction"; Journal of Heterocyclic Chemistry, vol. 40, 2003, pp. 773-782.

Yavari, Issa et al.; "A new synthesis of highly functionalized 2H-pyran derivatives"; Tetrahedron, 59, 2003, pp. 2001-2005.

Konopelski, Joseph P. et al.; "Carbanion Stabilization by Distal Silyloxy Groups. Origin of the High Diastereoselectivity in the Formation of Quaternary Centers with Aryllead (IV) Triacetate Reagents"; Organic Letters, vol. 4, No. 23, 2002, pp. 4121-4124.

Wiles, Charlotte et al.; "The regioselective preparation of 1,3-diketones"; Tetrahedron Letters 43, 2002, pp. 2945-2948.

Faure, Robert et al.; "Synthesis, $1_H$ and $13_C$ NMR Study of Pyrazoles Derived From Chiral Cyclohexanones (3-Methylcyclohexanone, Menthone, Pulegone, Dihydrocarvone and Carvone"; Heterocycles, vol. 57, No. 2, 2002, pp. 307-316.

Hammadi Mohamed et al.; "Clay Catalysis: Stork's Alkylation and Acylation of Cyclohexanone Without Isolation of Enamine"; Synthetic Communications, vol. 26(15), 1996, pp. 2901-2904.

Alvernhe, Gerard et al.; Synthesis and reactivity of 3-chloro-3-trifluoromethylacroleins: stabilisation of the tetrahedral intermediate in a nucleophilic vinylic "substitution"; Bull. Soc. Chim. Fr., vol. 131, 1994, pp. 167-172.

Meyer, Emerson et al.; "Synthesis of New 1,2,4- and 1,3,4-Oxadiazole Derivatives"; Synthesis 2003, No. 6, pp. 899-905.

Trapani, Giuseppe et al.; "Propofol Analogues. Synthesis, Relationships between Structure and Affinity at $GABA_A$ Receptor in Rat Brain, and Differential Electrophysiological Profile at Recombinant Human $GABA_A$ Receptors"; Journal of Medicinal Chemistry, 1998, vol. 41, No. 11, pp. 1846-1854.

Chakraborti, Asit K. et al.; "One-Pot Synthesis of Nitriles from Aldehydes Under Microwave Irradiation: Influence of the Medium and Mode of Microwave Irradiation on Producet Formation"; Tetrahedron 55, 1999, pp. 13265-13268.

Ecke, George G. et al.; "ortho-Alkylation of Aromatic Amines[1]"; J. Org. Chem., vol. 22, 1957, pp. 639-642.

* cited by examiner

THIOPHENE DERIVATIVES AS S1P1/EDG1 RECEPTOR AGONISTS

CROSS REFERENCE TO RELATED APPLICATIONS

This application is a United States National Stage Application under 35 U.S.C. 371 of PCT Application No. PCT/IB2007/050070, filed on Jan. 10, 2007, which claims the benefit of PCT Application No. PCT/IB2006/050103, filed on Jan. 11, 2006, the contents of each of which are incorporated herein by reference.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies. A further aspect of the invention relates to novel compounds of Formulae (II) and (III) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-infammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I), (II) or (III) is to be understood as referring also to salts, especially pharmaceutically acceptable salts, of a compound of Formula (I), (II) or (III), as appropriate and expedient.

The term $C_{1-4}$-alkyl, alone or in combination with other groups, means saturated, branched or preferably straight chain groups with one to four carbon atoms, preferably one to three carbon atoms. Examples of $C_{1-4}$-alkyl groups are methyl, ethyl, n-propyl, iso-propyl, n-butyl, iso-butyl, sec-butyl, and tert-butyl.

The term $C_{1-4}$-alkoxy, alone or in combination with other groups, means an R—O— group, wherein R is a $C_{1-4}$-alkyl.

Preferred examples of $C_{1-4}$-alkoxy groups are methoxy, ethoxy, propoxy, iso-propoxy, iso-butoxy, sec-butoxy and tert-butoxy.

The term hydroxy-$C_{2-4}$-alkoxy means a straight or branched alkoxy chain bearing a hydroxy group whereby there are at least two carbon atoms between the hydroxy group and the oxygen of the $C_{2-4}$-alkoxy group. Examples of hydroxy-$C_{2-4}$-alkoxy groups are 2-hydroxy-ethoxy, 3-hydroxy-propoxy, 2-hydroxy-propoxy, 4-hydroxy-butoxy, 3-hydroxy-1-methyl-propoxy, and 3-hydroxy-butoxy.

The term $C_{1-4}$-alkylamino or di-($C_{1-4}$-alkyl)amino, alone or in combination with other groups, means an R'—NH— or an R'—NR"— group, wherein R' and R" are each independently a $C_{1-4}$-alkyl group. Preferred examples of $C_{1-4}$-alkylamino or di-($C_{1-4}$-alkyl)amino groups are methylamino, ethylamino, N,N-dimethylamino, and N-methyl-N-ethylamino.

The term halogen means fluoro, chloro, bromo or iodo, preferably fluoro or chloro.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of Formula (I), (II) or (III) is acidic in nature, with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of Formula (I) and (III) may contain one or more stereogenic or asymmetric centers, such as one or more asymmetric carbon atoms. Substituents at a double bond or a ring may be present in cis- or trans-form (E- or Z-form) unless indicated otherwise. The compounds of Formula (I) and (III) may thus be present as mixtures of stereoisomers or preferably as pure stereoisomers. Mixtures of stereoisomers may be separated in a manner known to a person skilled in the art.

i) The invention relates to novel thiophene compounds of the Formula (I),

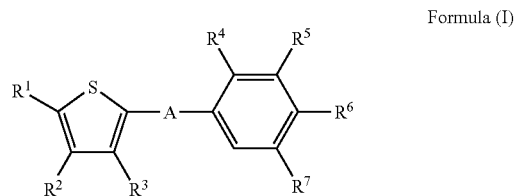

Formula (I)

wherein

A represents *—CO—CH=CH—, *—CO—CH$_2$CH$_2$—, *—CO—CH$_2$—NH—,

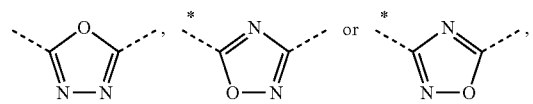

wherein the asterisks indicate the bond that is linked to the thiophene group of Formula (I);

$R^1$ represents hydrogen, methyl, or trifluoromethyl;

$R^2$ represents n-propyl, isobutyl, or cyclopropylmethyl;

$R^3$ represents hydrogen, methyl, trifluoromethyl, ethyl, n-propyl, isopropyl, or isobutyl;

$R^4$ represents hydrogen, $C_{1-4}$-alkyl, methoxy, or halogen;

$R^5$ represents hydrogen, $C_{1-4}$-alkyl, $C_{1-4}$-alkoxy, or halogen;

$R^6$ represents hydroxy-$C_{1-4}$-alkyl, di-(hydroxy-$C_{1-4}$-alkyl)-$C_{1-4}$-alkyl, 2,3-dihydroxypropyl, —CH$_2$—(CH$_2$)$_n$—NR$^{61}$R$^{62}$, —CH$_2$—(CH$_2$)$_n$—NHCOR$^{64}$, —CH$_2$—(CH$_2$)$_n$—NHSO$_2$R$^{63}$, —(CH$_2$)$_k$—(CHR$^{65}$)$_p$—CHR$^{66}$—CONR$^{61}$R$^{62}$, —(CH$_2$)$_n$CH(OH)—CH$_2$—NR$^{61}$R$^{62}$, —(CH$_2$)$_n$CH(OH)—CH$_2$—NHCOR$^{64}$, —(CH$_2$)$_n$CH(OH)—CH$_2$—NHSO$_2$R$^{63}$, —CO—NHR$^{61}$, hydroxy, hydroxy-$C_{2-4}$-alkoxy, di-(hydroxy-$C_{1-4}$-alkyl)-$C_{1-4}$-alkoxy, 1-glyceryl, 2,3-dihydroxypropoxy, 2-hydroxy-3-methoxy-propoxy, —OCH$_2$—(CH$_2$)$_m$—NR$^{61}$R$^{62}$, —OCH$_2$—(CH$_2$)$_m$—NHCOR$^{64}$, —OCH$_2$—(CH$_2$)$_m$—NHSO$_2$R$^{63}$, —OCH$_2$—CH(OH)—CH$_2$—NR$^{61}$R$^{62}$, —OCH$_2$—CH(OH)—CH$_2$—NHCOR$^{64}$, —OCH$_2$—CH(OH)—CH$_2$—NHSO$_2$R$^{63}$, —NR$^{61}$R$^{62}$, —NHCO—R$^{64}$, or —SO$_2$NH—R$^{61}$;

$R^{61}$ represents hydrogen, methyl, ethyl, 2-hydroxyethyl, 2-hydroxy-1-hydroxymethyl-ethyl, 2,3-dihydroxy-propyl, 2-$C_{1-4}$-alkoxyethyl, 3-hydroxypropyl, 3-$C_{1-4}$-alkoxypropyl, 2-aminoethyl, 2-($C_{1-4}$-alkylamino)ethyl, 2-(di-($C_{1-4}$-alkyl)amino)ethyl, carboxymethyl, $C_{1-4}$-alkylcarboxymethyl, 2-carboxyethyl, or 2-($C_{1-4}$-alkylcarboxy)ethyl;

$R^{62}$ represents hydrogen, or methyl;

$R^{63}$ represents methyl, ethyl, 2-hydroxyethyl, 2-methoxyethyl, methylamino, ethylamino, or dimethylamino;

$R^{64}$ represents hydroxymethyl, aminomethyl, methylaminomethyl, dimethylaminomethyl, 2-aminoethyl, or 2-methylamino-ethyl;

$R^{65}$ represents hydrogen;

$R^{66}$ represents hydrogen or hydroxy; and in case $R^{66}$ represents hydroxy, $R^{65}$ may in addition represent hydroxy;

m represents the integer 1 or 2;

n represents 0, 1, or 2;

k represents 0;

p represents 0 or 1; and in case p represents 1, k may in addition represent 1; and $R^7$ represents hydrogen, $C_{1-4}$-alkyl, or halogen;

and salts thereof.

ii) The present invention also relates to thiophene derivatives according to embodiment i), wherein $R^6$ represents hydroxy-$C_{1-4}$-alkyl, di-(hydroxy-$C_{1-4}$-alkyl)-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$(CH_2)_k$—$(CHR^{65})_p$—$CHR^{66}$—$CONR^{61}R^{62}$, —$(CH_2)_n$CH(OH)—$CH_2$—$NR^{61}R^{62}$, —$(CH_2)_n$CH(OH)—$CH_2$—$NHCOR^{64}$, —$(CH_2)_n$CH(OH)—$CH_2$—$NHSO_2R^{63}$, —CO—$NHR^{61}$, hydroxy, hydroxy-$C_{2-4}$-alkoxy, di-(hydroxy-$C_{1-4}$-alkyl)-$C_{1-4}$-alkoxy, 1-glyceryl, 2-hydroxy-3-methoxy-propoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, —$OCH_2$—CH(OH)—$CH_2$—$NR^{61}R^{62}$, —$OCH_2$—CH(OH)—$CH_2$—$NHCOR^{64}$, —$OCH_2$—CH(OH)—$CH_2$—$NHSO_2R^{63}$, —$NR^{61}R^{62}$, —NHCO—$R^{64}$, or —$SO_2NH$—$R^{61}$.

iii) A particular embodiment of the invention relates to thiophene derivatives according to embodiment i) or ii), wherein A represents *—CO—$CH_2$—$CH_2$—,

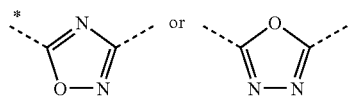

wherein the asterisks indicate the bond that is linked to the thiophene group of Formula (I).

iv) Another particular embodiment of the invention relates to thiophene derivatives according to embodiment i) or ii), wherein A represents *—CO—$CH_2$—$CH_2$—, wherein the asterisk indicates the bond that is linked to the thiophene group of Formula (I).

v) Another particular embodiment of the invention relates to thiophene derivatives according to embodiment i) or ii), wherein A represents

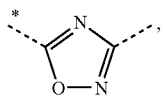

wherein the asterisk indicates the bond that is linked to the thiophene group of Formula (I).

vi) Another particular embodiment of the invention relates to thiophene derivatives according to embodiment i) or ii), wherein A represents

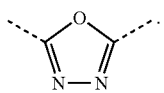

vii) Another particular embodiment of the invention relates to thiophene derivatives according to any one of the embodiments i) to vi), wherein $R^1$ represents hydrogen or methyl.

viii) Another particular embodiment of the invention relates to thiophene derivatives according to any one of the embodiments i) to vi), wherein $R^1$ represents hydrogen.

ix) Another particular embodiment of the invention relates to thiophene derivatives according to any one of the embodiments i) to vi), wherein $R^1$ represents a methyl group.

x) A preferred embodiment of the invention relates to thiophene derivatives according to any one of the embodiments i) to ix), wherein $R^2$ represents an isobutyl group.

xi) Another preferred embodiment of the invention relates to thiophene derivatives according to any one of the embodiments i) to x), wherein $R^3$ represents methyl, ethyl, n-propyl, or isobutyl.

xii) Another preferred embodiment of the invention relates to thiophene derivatives according to any one of the embodiments i) to x), wherein $R^3$ represents a methyl group.

xiii) Another preferred embodiment of the invention relates to thiophene derivatives according to any one of the embodiments i) to xii), wherein $R^4$ represents methoxy, and $R^5$ and $R^7$ represent hydrogen, or wherein $R^4$ represents hydrogen and $R^5$ represents methyl, ethyl, or methoxy and $R^7$ represents methyl, ethyl or halogen.

xiv) Another preferred embodiment of the invention relates to thiophene derivatives according to any one of the embodiments i) to xii), wherein $R^4$ represents a methoxy group, and $R^5$ and $R^7$ represent hydrogen.

xv) Another preferred embodiment of the invention relates to thiophene derivatives according to any one of the embodiments i) to xii), wherein $R^4$ represents hydrogen, and $R^5$ and $R^7$ represent a methyl group.

xvi) Another preferred embodiment of the invention relates to thiophene derivatives according to any one of the embodiments i) to xii), wherein $R^4$ represents hydrogen, and $R^5$ and $R^7$ represent an ethyl group.

xvii) A particularly preferred embodiment of the invention relates to thiophene derivatives according to any one of the embodiments i) to xii), wherein $R^4$ represents hydrogen, $R^5$ represents a methyl group, and $R^7$ represents an ethyl group.

xviii) Another preferred embodiment of the invention relates to thiophene derivatives according to any one of the embodiments i) to xii), wherein $R^4$ represents hydrogen, $R^5$ represents a methoxy group, and $R^7$ represents a chlorine atom.

xix) Another preferred embodiment of the invention relates to thiophene derivatives according to any one of the embodiments i) to xii), wherein $R^4$ represents hydrogen, $R^5$ represents a methyl group, and $R^7$ represents a chlorine atom.

xx) Another preferred embodiment of the invention relates to thiophene derivatives according to any one of the embodiments i) to xix), wherein $R^6$ represents —$(CH_2)_k$—$(CHR^{65})_p$—$CHR^{66}$—$CONR^{61}R^{62}$.

xxi) A particularly preferred embodiment of the invention relates to thiophene derivatives according to any one of the embodiments i) to xix), wherein $R^6$ represents —$(CH_2)_k$—$(CHR^{65})_p$—$CHR^{66}$—$CONR^{61}R^{62}$, wherein k represents 0, p represents 1, and $R^{65}$ and $R^{66}$ represent hydrogen.

xxii) A preferred embodiment of the invention relates to thiophene derivatives according to any one of the embodiments i) to xix), wherein $R^6$ represents —$OCH_2$—CH(OH)—$CH_2$—$NHCOR^{64}$.

xxiii) A particularly preferred embodiment of the invention relates to thiophene derivatives according to any one of the embodiments i) to xix), wherein $R^6$ represents —$OCH_2$—CH(OH)—$CH_2$—$NHCOR^{64}$, wherein $R^{64}$ represents hydroxymethyl.

xxiv) A particular embodiment of the invention relates to thiophene derivatives according to any one of the embodiments i) and iii) to xix), wherein $R^6$ represents 2,3-dihydroxypropoxy.

xxv) Another particular embodiment of the invention relates to thiophene derivatives according to any one of the embodiments ii) to xix), wherein $R^6$ represents 1-glyceryl.

xxvi) An especially preferred embodiment of the invention relates to thiophene derivatives according to embodiment i), wherein A represents *—CO—CH=CH—, *—CO—CH$_2$CH$_2$—,

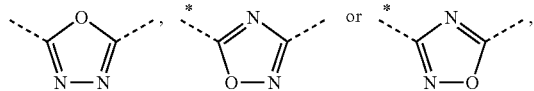

wherein the asterisks indicate the bond that is linked to the thiophene group of Formula (I);
$R^1$ represents hydrogen or methyl;
$R^2$ represents n-propyl or isobutyl;
$R^3$ represents hydrogen, methyl, ethyl, n-propyl, isopropyl, or isobutyl;
$R^4$ represents hydrogen or methoxy;
$R^5$ represents hydrogen, $C_{1-4}$-alkyl, or $C_{1-4}$-alkoxy;
$R^6$ represents hydroxy; hydroxy-$C_{2-4}$-alkoxy; 2,3-dihydroxypropoxy; —OCH$_2$—(CH$_2$)$_m$—NHCOR$^{64}$; —OCH$_2$—CH(OH)—CH$_2$—NR$^{61}$R$^{62}$; —OCH$_2$—CH(OH)—CH$_2$—NHCOR$^{64}$; —OCH$_2$—CH(OH)—CH$_2$—NHSO$_2$R$^{63}$; or —CH$_2$—CH$_2$—CONHR', wherein R' is 2-hydroxyethyl, 2-hydroxy-1-hydroxymethyl-ethyl, hydroxycarbonylmethyl, or methoxycarbonylmethyl;
$R^{61}$ and $R^{62}$ represent hydrogen;
$R^{63}$ represents methyl;
$R^{64}$ represents hydroxymethyl, methylaminomethyl, or 2-methylamino-ethyl;
m represents the integer 1 or 2; and
$R^7$ represents hydrogen, $C_{1-4}$-alkyl, or halogen.

xxvii) Another especially preferred embodiment of the invention relates to thiophene derivatives according to embodiment ii), wherein
A represents *—CO—CH=CH—, *—CO—CH$_2$CH$_2$—,

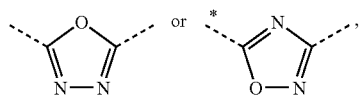

wherein the asterisks indicate the bond that is linked to the thiophene group of Formula (I);
$R^1$ represents hydrogen or methyl;
$R^2$ represents n-propyl or isobutyl;
$R^3$ represents hydrogen, methyl, ethyl, n-propyl, isopropyl, or isobutyl;
$R^4$ represents hydrogen or methoxy;
$R^5$ represents hydrogen or $C_{1-4}$-alkyl;
$R^6$ represents hydroxy, hydroxy-$C_{2-4}$-alkoxy, 1-glyceryl, —OCH$_2$—(CH$_2$)$_m$—NHCOR$^{64}$, —OCH$_2$—CH(OH)—CH$_2$—NR$^{61}$R$^{62}$, or —OCH$_2$—CH(OH)—CH$_2$—NHCOR$^{64}$;
$R^{61}$ and $R^{62}$ represent hydrogen;
$R^{64}$ represents hydroxymethyl, methylaminomethyl, or 2-methylamino-ethyl;
m represents the integer 2; and
$R^7$ represents hydrogen or $C_{1-4}$-alkyl.

xxviii) A preferred embodiment of the invention relates to thiophene derivatives according to embodiment i) or ii), wherein $R^1$ represents hydrogen or methyl, $R^2$ represents isobutyl, $R^3$ represents hydrogen or methyl, $R^4$ represents hydrogen, $R^5$ and $R^7$ represent $C_{1-4}$-alkyl, $R^6$ represents —OCH$_2$—CH(OH)—CH$_2$—NHCOR$^{64}$, and A represents

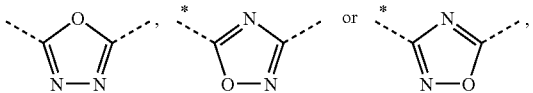

wherein the asterisks indicate the bond that is linked to the thiophene group of Formula (I).

xxix) Especially preferred thiophene compounds according to Formula (I) are:
3-(4-hydroxy-3,5-dimethyl-phenyl)-1-(4-isobutyl-3-propyl-thiophen-2-yl)-propenone;
1-(3,4-diisobutyl-thiophen-2-yl)-3-(4-hydroxy-3,5-dimethyl-phenyl)-propenone;
1-(3,4-diisobutyl-thiophen-2-yl)-3-(4-hydroxy-3,5-dimethyl-phenyl)-propan-1-one;
3-[4-((S)-2,3-dihydroxy-propoxy)-3,5-dimethyl-phenyl]-1-(4-isobutyl-3-propyl-thiophen-2-yl)-propan-1-one;
3-[4-((S)-2,3-dihydroxy-propoxy)-3,5-dimethyl-phenyl]-1-(4-isobutyl-3,5-dimethyl-thiophen-2-yl)-propan-1-one;
2-hydroxy-N-(2-hydroxy-3-{4-[5-(4-isobutyl-5-methyl-thiophen-2-yl)-[1,2,4]oxadiazol-3-yl]-2,6-dimethyl-phenoxy}-propyl)-acetamide;
N-(3-{2-ethyl-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide;
N-(3-{2-ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;
2-hydroxy-N-(2-hydroxy-3-{4-[3-(4-isobutyl-3-propyl-thiophen-2-yl)-3-oxo-propyl]-2,6-dimethyl-phenoxy}-propyl)-acetamide;
N-(3-{4-[3-(3,4-diisobutyl-thiophen-2-yl)-3-oxo-propyl]-2,6-dimethyl-phenoxy}-2-hydroxy-propyl)-2-hydroxy-acetamide;
2-hydroxy-N-(2-hydroxy-3-{4-[5-(4-isobutyl-3-methyl-thiophen-2-yl)-[1,2,4]oxadiazol-3-yl]-2,6-dimethyl-phenoxy}-propyl)-acetamide;
N-(2-hydroxy-3-{4-[5-(4-isobutyl-3-methyl-thiophen-2-yl)-[1,2,4]oxadiazol-3-yl]-2,6-dimethyl-phenoxy}-propyl)-2-methylamino-acetamide;
2-hydroxy-N-(3-{4-[5-(4-isobutyl-3-methyl-thiophen-2-yl)-[1,2,4]oxadiazol-3-yl]-2,6-dimethyl-phenoxy}-propyl)-acetamide;
3-{4-[5-(4-isobutyl-3-methyl-thiophen-2-yl)-[1,3,4]oxadiazol-2-yl]-2,6-dimethyl-phenoxy}-propane-1,2-diol;
3-{4-[5-(3-ethyl-4-isobutyl-thiophen-2-yl)-[1,3,4]oxadiazol-2-yl]-2,6-dimethyl-phenoxy}-propane-1,2-diol;
3-{4-[5-(4-isobutyl-3-propyl-thiophen-2-yl)-[1,3,4]oxadiazol-2-yl]-2,6-dimethyl-phenoxy}-propane-1,2-diol;
3-{4-[5-(3,4-diisobutyl-thiophen-2-yl)-[1,3,4]oxadiazol-2-yl]-2,6-dimethyl-phenoxy}-propane-1,2-diol;
2-hydroxy-N-(2-hydroxy-3-{4-[5-(4-isobutyl-3-methyl-thiophen-2-yl)-[1,3,4]oxadiazol-2-yl]-2,6-dimethyl-phenoxy}-propyl)-acetamide;
N-(3-{4-[5-(3-ethyl-4-isobutyl-thiophen-2-yl)-[1,3,4]oxadiazol-2-yl]-2,6-dimethyl-phenoxy}-2-hydroxy-propyl)-2-hydroxy-acetamide;
2-hydroxy-N-(2-hydroxy-3-{4-[5-(4-isobutyl-3-propyl-thiophen-2-yl)-[1,3,4]oxadiazol-2-yl]-2,6-dimethyl-phenoxy}-propyl)-acetamide;

N-(3-{4-[5-(3,4-diisobutyl-thiophen-2-yl)-[1,3,4]oxadiazol-2-yl]-2,6-dimethyl-phenoxy}-2-hydroxy-propyl)-2-hydroxy-acetamide;

3-{4-[5-(4-isobutyl-5-methyl-thiophen-2-yl)-[1,2,4]oxadiazol-3-yl]-3-methoxy-phenoxy}-propane-1,2-diol;

2-hydroxy-N-(2-hydroxy-3-{4-[5-(4-isobutyl-5-methyl-thiophen-2-yl)-[1,2,4]oxadiazol-3-yl]-3-methoxy-phenoxy}-propyl)-acetamide; and 2-hydroxy-N-(2-hydroxy-3-{4-[5-(4-isobutyl-3,5-dimethyl-thiophen-2-yl)-[1,2,4]oxadiazol-3-yl]-2,6-dimethyl-phenoxy}-propyl)-acetamide.

xxx) Further especially preferred thiophene compounds according to Formula (I) are:

N—((S)-3-{2,6-diethyl-4-[5-(4-isobutyl-5-methyl-thiophen-2-yl)-[1,2,4]oxadiazol-3-yl]-phenoxy}-2-hydroxy-propyl)-2-hydroxy-acetamide;

N—((S)-3-{2-chloro-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide;

N—((R)-3-{2-chloro-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide;

3-{2-ethyl-4-[5-(4-isobutyl-5-methyl-thiophen-2-yl)-[1,2,4]oxadiazol-3-yl]-6-methyl-phenyl}-N-(2-hydroxy-ethyl)-propionamide;

2-hydroxy-N—((S)-2-hydroxy-3-{4-[5-(4-isobutyl-5-methyl-thiophen-2-yl)-[1,3,4]oxadiazol-2-yl]-2,6-dimethyl-phenoxy}-propyl)-acetamide;

2-hydroxy-N—((R)-2-hydroxy-3-{4-[5-(4-isobutyl-5-methyl-thiophen-2-yl)-[1,3,4]oxadiazol-2-yl]-2,6-dimethyl-phenoxy}-propyl)-acetamide;

N—((R)-3-{2-ethyl-4-[5-(4-isobutyl-5-methyl-thiophen-2-yl)-[1,3,4]oxadiazol-2-yl]-6-methyl-phenoxy}-2-hydroxy-propyl)-2-hydroxy-acetamide;

N—((S)-3-{2-ethyl-4-[5-(4-isobutyl-5-methyl-thiophen-2-yl)-[1,3,4]oxadiazol-2-yl]-6-methyl-phenoxy}-2-hydroxy-propyl)-2-hydroxy-acetamide;

N-(2-hydroxy-1-hydroxymethyl-ethyl)-3-{4-[5-(4-isobutyl-5-methyl-thiophen-2-yl)-[1,3,4]oxadiazol-2-yl]-2,6-dimethyl-phenyl}-propionamide;

2-hydroxy-N—((S)-2-hydroxy-3-{4-[5-(4-isobutyl-3-methyl-thiophen-2-yl)-[1,2,4]oxadiazol-3-yl]-2,6-dimethyl-phenoxy}-propyl)-acetamide;

2-hydroxy-N—((R)-2-hydroxy-3-{4-[5-(4-isobutyl-3-methyl-thiophen-2-yl)-[1,2,4]oxadiazol-3-yl]-2,6-dimethyl-phenoxy}-propyl)-acetamide;

N—((S)-3-{2-ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;

N—((R)-3-{2-ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;

N—((S)-3-{2-chloro-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;

N—((R)-3-{2-chloro-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;

N—((S)-3-{2,6-diethyl-4-[5-(4-isobutyl-3-methyl-thiophen-2-yl)-[1,2,4]oxadiazol-3-yl]-phenoxy}-2-hydroxy-propyl)-2-hydroxy-acetamide;

N—((R)-3-{2,6-diethyl-4-[5-(4-isobutyl-3-methyl-thiophen-2-yl)-[1,2,4]oxadiazol-3-yl]-phenoxy}-2-hydroxy-propyl)-2-hydroxy-acetamide;

N—((S)-3-{2-ethyl-4-[5-(4-isobutyl-3-methyl-thiophen-2-yl)-[1,2,4]oxadiazol-2-yl]-6-methyl-phenoxy}-2-hydroxy-propyl)-2-hydroxy-acetamide;

N—((R)-3-{2-ethyl-4-[5-(4-isobutyl-3-methyl-thiophen-2-yl)-[1,3,4]oxadiazol-2-yl]-6-methyl-phenoxy}-2-hydroxy-propyl)-2-hydroxy-acetamide;

2-hydroxy-N—((S)-2-hydroxy-3-{4-[3-(4-isobutyl-3-methyl-thiophen-2-yl)-[1,2,4]oxadiazol-5-yl]-2,6-dimethyl-phenoxy}-propyl)-acetamide;

2-hydroxy-N—((R)-2-hydroxy-3-{4-[3-(4-isobutyl-3-methyl-thiophen-2-yl)-[1,2,4]oxadiazol-5-yl]-2,6-dimethyl-phenoxy}-propyl)-acetamide;

2-hydroxy-N—((S)-2-hydroxy-3-{4-[3-(4-isobutyl-3,5-dimethyl-thiophen-2-yl)-3-oxo-propyl]-2,6-dimethyl-phenoxy}-propyl)-acetamide;

2-hydroxy-N—((R)-2-hydroxy-3-{4-[3-(4-isobutyl-3,5-dimethyl-thiophen-2-yl)-3-oxo-propyl]-2,6-dimethyl-phenoxy}-propyl)-acetamide;

N—((S)-3-{2-ethyl-4-[3-(4-isobutyl-3,5-dimethyl-thiophen-2-yl)-3-oxo-propyl]-6-methyl-phenoxy}-2-hydroxy-propyl)-2-hydroxy-acetamide;

N—((R)-3-{2-ethyl-4-[3-(4-isobutyl-3,5-dimethyl-thiophen-2-yl)-3-oxo-propyl]-6-methyl-phenoxy}-2-hydroxy-propyl)-2-hydroxy-acetamide;

N—((S)-3-{2-chloro-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide;

N—((R)-3-{2-chloro-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide;

2-hydroxy-N—((S)-2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide;

2-hydroxy-N—((R)-2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide;

N—((R)-3-{2-ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide; and N—((S)-3-{2-ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide.

xxxi) A further aspect of the invention relates to novel compounds of Formula (II)

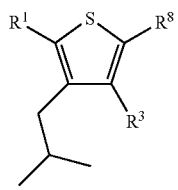

Formula (II)

wherein $R^1$ and $R^3$ are as defined for Formula (I) above, and $R^8$ represents —COOH, —COOCH$_3$, —COOCH$_2$CH$_3$, or —CN;

and salts thereof.

xxxii) A further aspect of the invention relates to novel compounds of Formula (III)

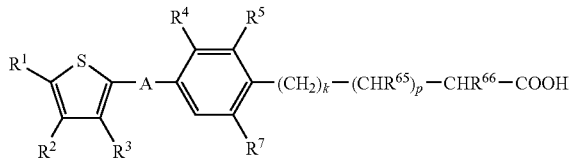

Formula (III)

wherein A, $R^1$, $R^2$, $R^3$, $R^4$, $R^5$, $R^{65}$, $R^{66}$, $R^7$, k and p are as defined for Formula (I) above;
and salts thereof.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

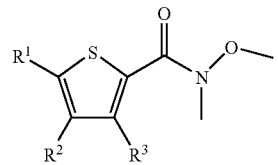

Structure 1

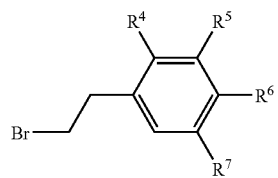

Structure 2

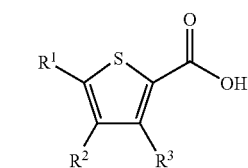

Structure 3

In case A represents —CO—CH$_2$—CH$_2$—, the compounds of Formula (I) may be prepared by reacting a compound of Structure 1 with a compound of Structure 2 under Grignard conditions, preferably at temperatures below rt. The Grignard reagent of Structure 2 is prepared according to standard methodology. The functional groups present in the residues $R^4$ to $R^7$ may require temporary protection or may even be introduced in additional steps that follow the Grignard reaction. The Weinreb amide compound of Structure 1 is prepared by treating a compound of Structure 3 with N,O-dimethylhydroxylamine hydrochloride in the presence of a coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, *Current Organic Chemistry* 7 (2003), 967-993).

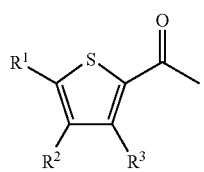

Structure 4

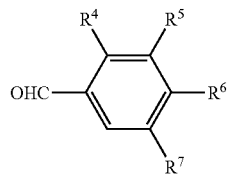

Structure 5

In case A represents —CO—CH═CH—, the compounds of Formula (I) may be prepared by reacting a compound of Structure 4 with a compound of Structure 5 in the presence of a base or an acid. Compounds of Formula (I) wherein A represents —CO—CH$_2$—CH$_2$— may also be prepared by reacting a compound of Formula (I) wherein A represents —CO—CH═CH— (Structure 6) with hydrogen in the presence of a catalyst such as Pd/C, Pt/C, PtO$_2$, etc. in a solvent such as ethanol, methanol, THF, etc.

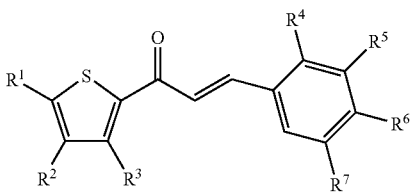

Structure 6

Compounds of the Formula (I) wherein A represents —CO—CH$_2$—NH— may be prepared by reacting a compound of Structure 7 with a compound of Structure 8 in the presence or absence of a base such as K$_2$CO$_3$, Na$_2$CO$_3$, K-tert.butoxide, NaOH, NaH, triethylamine, DIPEA, etc. in a solvent such as acetone, DMF, THF, dioxane, etc., or mixtures thereof. The compounds of Structure 7 can be prepared by reacting a compound of Structure 4 with a brominating agent such as phenyltrimethylammoniumbromid dibromide, benzyltrimethylammonium-tribromid, triphenylphosphine dibromide, etc. in a solvent such as DCM, chloroform, THF, diethyl ether, methanol, ethanol, etc., or mixtures thereof.

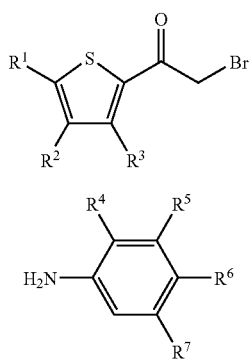

Structure 7

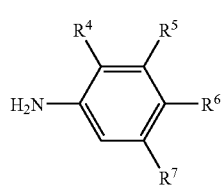

Structure 8

A compound of Structure 4 may be prepared by treating a compound of Structure 3 with MeLi in a solvent such as diethyl ether, THF, and dioxane, at temperatures between −20 and 50° C. Alternatively, a compound of Structure 4 may be prepared by reacting a compound of Structure 1 with methylmagnesium bromide.

Compounds of Formula (I) which represent a 5-thiophen-2-yl-[1,2,4]oxadiazole derivative, are prepared by reacting a compound of Structure 9 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Structure 9

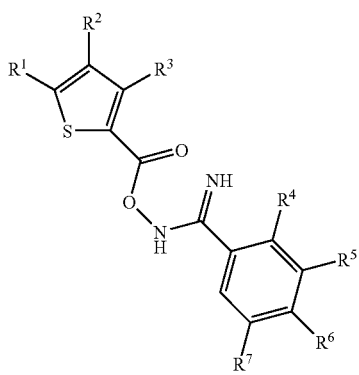

Compounds of Structure 9 may be prepared by reacting a compound of Structure 3 with a compound of Structure 10 in a solvent such as DMF, THF, etc. in the presence or absence of one or more coupling agents such as TBTU, DCC, EDC, HBTU, HOBt, CDI, etc. and in the presence or absence of a base such as triethylamine, Hünig's base, NaH, $K_2CO_3$, etc.

(Lit: e.g. A. Hamze, J.-F. Hernandez, P. Fulcrand, J. Martinez, *J. Org. Chem.* 68 (2003) 7316-7321; and the literature cited above).

Structure 3

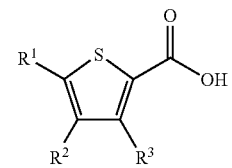

Structure 10

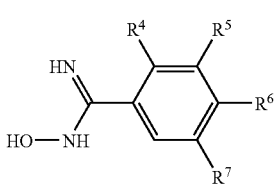

Compounds of Formula (I) which represent a 5-thiophen-2-yl-[1,3,4]oxadiazole or a 3-thiophen-2-yl-[1,2,4]oxadiazole derivative are prepared in an analogous fashion (Lit. e.g. C. T. Brain, J. M. Paul, Y. Loong, P. J. Oakley, *Tetrahedron Lett.* 40 (1999) 3275-3278). Hence, compounds of Formula (I) which represent a 3-thiophen-2-yl-[1,2,4]oxadiazole derivative are prepared by reacting a compound of Structure 11 with a compound of Structure 12.

Structure 11

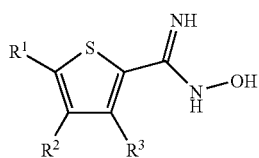

Structure 12

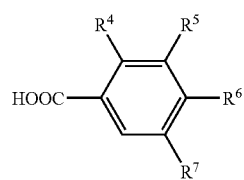

Compounds of Structure 10 and 11 may be prepared by reacting a compound of Structure 13 and 14, respectively, with hydroxylamine or one of its salts in a solvent such as methanol, ethanol, pyridine, etc. in the presence or absence of a base such as $Na_2CO_3$, $K_2CO_3$, triethylamine, etc. (Lit: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

Structure 13

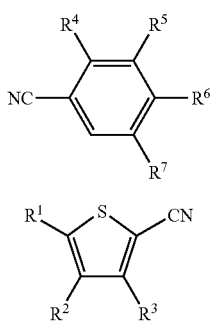

Structure 14

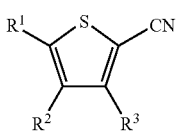

Depending on the nature of the functionalities present in the residues $R^4$ to $R^7$ in Structures 2, 5, 6, 8, 9, 10 and 12, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^4$ to $R^7$ may also be introduced in later steps that follow the reaction of a compound of Structure 1, 4, 7, 3, and 11 with a suitable precursor of a compound of Structure 2, 5, 8, 10 and 12, respectively. The compounds of Structure 2, 5, 8, 12, and 13 or their precursors are either commercially available or are prepared according to procedures known to a person skilled in the art.

A compound of Formula (I), wherein $R^6$ represents —$(CH_2)_k$—$(CHR^{65})_p$—$CHR^{66}$—$CONR^{61}R^{62}$ may be prepared by reacting a compound of Formula (III) with the appropriate amine in the presence of a coupling reagent such as TBTU, EDC, etc. The compounds of Formula (III) are prepared in analogy to the procedures outlined above for the preparation of compounds of Formula (I).

Structure 15

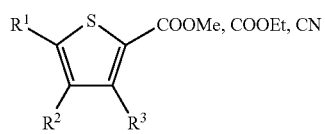

A compound of Structure 3 may be prepared by reacting a compound of Structure 15 with an aqueous base such as aq. NaOH, aq. LiOH, aq. KOH, etc. or an acid such as aq. HCl, TFA, etc. in a solvent such as water, ethanol, methanol, THF, etc. or mixtures thereof.

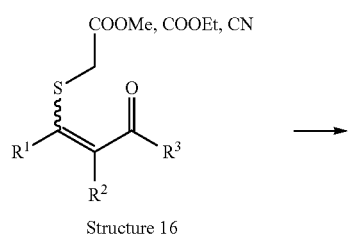

Structure 16

-continued

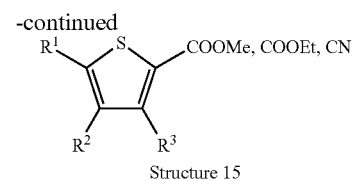

Structure 15

The compounds of Structure 15 are prepared by treating a compound of Structure 16 with a non-aqueous base such as NaOMe, NaOEt, KOtBu, DBU, etc. in a solvent such as methanol, ethanol, THF, DMF, etc. or mixtures thereof, preferably at elevated temperatures.

The compounds of Structure 16 are prepared by treating a compound of Structure 17 with a mercaptoacetic acid ester or mercaptoacetonitrile, which can be generated in situ from thioacetic acid S-cyanomethyl ester, in the presence of a base such a NaH, NaOEt, NaOMe, K tert.-butoxide, etc. in THF, dioxane, DMF, ethanol, methanol, etc. or mixtures thereof. In addition, the compounds of Structure 3 may also be prepared in a one-pot three step procedure starting from a compound of Structure 17 following the above reaction sequence.

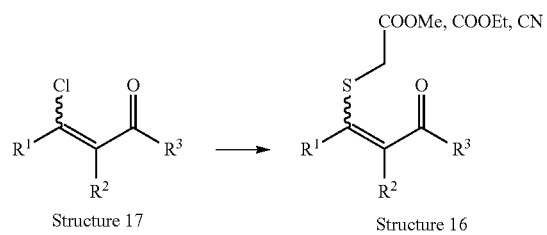

Structure 17          Structure 16

The compounds of Structure 17 are prepared by reacting a compound of Structure 18 with a chlorinating agent such as oxalylchloride or $CCl_4/PPh_3$ in a solvent such as DCM, $CHCl_3$, THF, etc. (Lit. e.g. R. E. Mewshaw, *Tetrahedron Lett.* 30 (1989), 3753-3756; F. A. Lakhvich, T. S. Khlebnikova, A. A. Akhrem, *Zhurnal Organicheskoi Khimii* 25 (1989), 2541-2549; S. A. Popov, A. V. Tkachev, *Synthetic Communications* (2001), 31(2), 233-243).

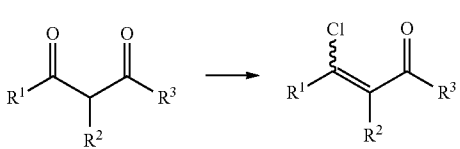

Structure 18          Structure 17

Structure 19

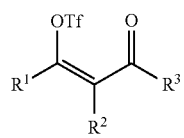

The compounds of Structure 16 may also be obtained by reacting a compound of Structure 18 with e.g. trifluoromethanesulfonic acid anhydride in DCM in the presence of a base to give a compound of Structure 19 (Lit. e.g. G. T. Crisp, A. G. Meyer, *J. Org. Chem.* 57 (1992) 6972-6975; R. M. Keenan, et al. *J. Med. Chem.* 35 (1992) 3858-3872) which is then converted to a compound of Structure 16 by treatment with a mercaptoacetic acid ester or mercaptoacetonitrile as described above.

The compounds of Structure 18 may be prepared by acylating a compound of Structure 20 with an appropriate acylating agent such as ethyl or methyl formate, methyl or ethyl acetate, methyl or ethyl propionate, chloroformate, acetyl chloride, etc. in the presence of a base such as K-tert. butylate, NaOMe, NaH, LDA, etc. in a solvent such as THF, toluene, EtOH etc. at temperatures between 0 and 60° C. (Lit. e.g. Ch. Kashima, S. Shibata, H. Yokoyama, T. Nishio, *Journal of Heterocyclic Chemistry* 40 (2003), 773-782; I. Yavari, Issa, M. Bayat, *Tetrahedron* 59 (2003), 2001-2005; J. P. Konopelski, J. Lin, P. J. Wenzel, H. Deng, G. I. Elliott, B. S. Gerstenberger, *Organic Letters* 4 (2002) 4121-4124; C. Wiles, P. Watts, S. J. Haswell, E. Pombo-Villar, *Tetrahedron Letters* 43 (2002), 2945-2948; R. Faure, A. Frideling, J.-P. Galy, I. Alkorta, J. Elguero, *Heterocycles* 57 (2002) 307-316; via imine: M. Hammadi, D. Villemin, *Synthetic Communications* 26 (1996) 2901-2904).

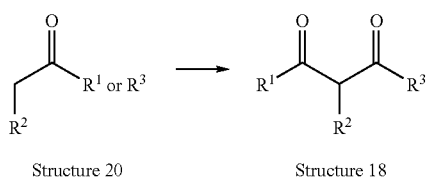

Structure 20    Structure 18

The compounds of Structure 18 may also be prepared by alkylation of the appropriate dicarbonyl compound of Structure 21 under conditions known to a person skilled in the art.

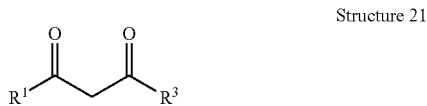

Structure 21

The compounds of Structure 20 and 21 are either commercially available or are prepared according to procedures known to a person skilled in the art. Compounds of Structure 17, wherein $R^3$ represents hydrogen may also be prepared by reacting a compound of Structure 20 containing the desired residue $R^1$ under Vilsmeyer conditions with $POCl_3$/DMF in a solvent such as DCM (e.g. G. Alvernhe, D. Greif, B. Langlois, A. Laurent, I. Le Dréan, M. Pulst, A. Selmi, M. Weissenfels, *Bull. Soc. Chim. Fr.* 131 (1994) 167-172).

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

Abbreviations (as used herein):
aq. aqueous
atm atmosphere
Boc-sarcosine N-tert. butyloxycarbonyl-sarcosine
BSA bovine serum albumin
Bu butyl
CC column chromatography
CU carbonyl diimidazole
DBU 1,8-diazabicylo[5.4.0]undec-7-en
DCC dicyclohexyl carbodiimide
DCM dichloromethane
DIPEA diisopropyl-ethylamine, Hünig's base, ethyl-diisopropylamine
DMF dimethylformamide
DMSO dimethylsulfoxide
DPPP 1,3-bis-(diphenylphosphino)-propane
EA ethyl acetate
EDC N-(3-dimethylaminopropyl)-N'-ethyl-carbodiimide
Et ethyl
EtOH ethanol
h hour(s)
HBTU O-(benzotriazol-1-yl)-N,N,N',N'-tetramethyluronium hexafluorophosphate
HOBt 1-hydroxybenzotriazole
HPLC high performance liquid chromatography
HV high vacuum conditions
KOtBu potassium tert-butoxide
LC-MS liquid chromatography-mass spectrometry
LDA lithium diisopropyl amide
Me methyl
MeOH methanol
min minute(s)
MPLC medium pressure liquid chromatography
NaOAc sodium acetate
NMO N-methyl-morpholine-N-oxide
OAc acetate
Ph phenyl
prep. preparative
rt room temperature
sat. saturated
S1P sphingosine 1-phosphate
TBTU 2-(1H-benzotriazole-1-yl)-1,2,3,3-tetramethyluronium tetrafluoroborate
Tf trifluoromethylsulfonyl
TFA trifluoroacetic acid
THF tetrahydrofuran
TLC thin layer chromatography
$t_R$ retention time given in minutes Intermediate A1

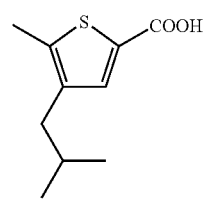

a) Phosphorusoxychloride (53.7 g, 350 mmol) is slowly added to DMF (60 mL) stirred at 5° C. Upon complete addition, the clear solution is stirred for further 30 min at 5° C. before 5-methyl-2-hexanone (20 g, 175 mmol) is added dropwise. The yellow solution is stirred for 30 min at 0° C., then for 90 min at rt. The mixture becomes warm (40° C.) and a thick suspension forms. The mixture is cooled to 25° C. and stirring is continued for 1 h before it is poured into an aq. solution of NaOAc (80 g)/ice mixture. The mixture is extracted twice with diethyl ether. The organic extracts are washed with water, combined, dried over MgSO$_4$, filtered and evaporated to give crude 3-chloro-2-isobutyl-but-2-enal (35.4 g) as a yellow oil, LC-MS: $t_R$=0.97 min.

b) Sodium (10.7 g, 467 mmol) is dissolved in ethanol (500 mL) and the resulting solution is diluted with THF (100 mL) before mercapto-acetic acid ethyl ester (33.7 g, 280 mmol) dissolved in THF (70 mL) is slowly added at 5° C. The mixture is stirred at rt for 1 h before a solution of 3-chloro-2-isobutyl-but-2-enal (30 g, 187 mmol) in THF (100 mL) is slowly added at 8° C. The resulting yellow suspension is stirred at rt for 16 h. The reaction mixture is diluted with diethyl ether (500 mL) and is washed with dilute aq. NaOCl solution, followed by aq. 1N HCl and water. The organic extract is dried over MgSO$_4$, filtered and evaporated. The remaining orange oil is dissolved in ethanol (150 mL) and 2N aq. LiOH (50 mL) is added. The mixture is stirred for 16 h at 50° C., acidified with 2 N aq. HCl and extracted with EA. The organic extract is dried over MgSO$_4$, filtered and evaporated. The crude product is recrystallized from EA/heptane to give 4-isobutyl-5-methyl-thiophene-2-carboxylic acid (10.5 g) as colourless crystals; LC-MS: $t_R$=0.92 min, [M+1+CH$_3$CN]= 240.16; $^1$H NMR (CDCl$_3$): δ 7.59 (s, 1H), 2.40-2.37 (m, 5H), 1.84 (hept, J=7.0 Hz, 1H), 0.90 (d, J=7.0 Hz, 6H).

Intermediate A2

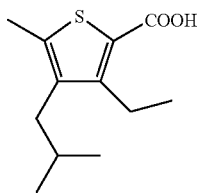

At −78° C., tert.-butyllithium (20 mL, 1.5 M in pentane) is slowly added to a solution of 4-isobutyl-5-methyl-thiophene-2-carboxylic acid (2.0 g, 10.1 mmol) in THF (100 mL). The mixture turns dark. The mixture is stirred at −78° C. for 15 min, then a solution of iodoethane (6.18 g, 39.6 mmol) in THF (10 mL) is added. The mixture is stirred for 1 h at −78° C. Further iodoethane (6.18 g, 39.6 mmol) is added and the mixture allowed to warm to rt over a period of 15 h. The reaction is quenched by adding 1 M aq. NaH$_2$PO$_4$ (20 mL) and 1 N aq. HCl (50 mL) and the mixture is extracted with chloroform (1×100 mL, 3×30 mL). The combined organic extracts are dried over MgSO$_4$, filtered and evaporated. The crude product is purified by MPLC on silica gel eluting with a gradient of EA in hexane to give 3-ethyl-4-isobutyl-5-methyl-thiophene-2-carboxylic acid (1.29 g) as a yellow solid; LC-MS: $t_R$=1.00 min, [M+1+CH$_3$CN]=268.29; $^1$H NMR (CDCl$_3$): δ 2.92 (q, J=7.0 Hz, 2H), 2.40 (s, 3H), 2.37 (d, J=7.6 Hz, 2H), 1.80 (m, J=7.0 Hz, 1H), 1.15 (t, J=7.6 Hz, 3H), 0.92 (d, J=7.0 Hz, 6H).

Intermediate A3

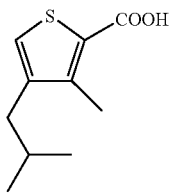

a) To a solution of KOtBu (50 g, 446 mmol) in THF (400 mL) is added during 30 min ethylformate (92 g, 1.25 mol). Strong gas evolution occurs. The mixture is cooled during the addition with a water bath at 10° C. After complete addition, the mixture is stirred until the gas evolution ceases (15 min). The mixture is cooled with ice at 0° C. and a mixture of 5-methyl-2-hexanone (34.25 g, 300 mmol) and ethylformate (41 g, 0.55 mol) is added slowly during 30 min. The mixture is stirred for 15 h, diluted with EA (500 mL) and washed with 1 N aq. HCl (100 mL), 1 M aq. NaH$_2$PO$_4$ solution (100 mL) and brine (100 mL). The organic extract is dried (MgSO$_4$), filtered and evaporated to give crude 4-hydroxy-3-isobutyl-but-3-en-2-one (28 g) which is used without further purification; LC-MS: $t_R$=0.80 min, [M+1]=143.39.

b) To a solution of 4-hydroxy-3-isobutyl-but-3-en-2-one (28 g, 197 mmol) in chloroform (350 mL) a soution of oxalyl-chloride (44.3 g, 349 mmol) in chloroform (50 mL) is added slowly during 5 min. The resulting dark brown mixture is stirred at rt for 2 h before it is cooled to 0° C. and treated with ice (100 g) followed by 1 N aq. NaOH (100 mL). When the quite violent gas evolution ceases the phases are separated (the still acidic aq. phase is discarded). The organic phase is washed with 1N aq. NaOH (3×75 mL) and 1 N aq. NaH$_2$PO$_4$ (75 mL), dried (MgSO$_4$), filtered and evaporated to give crude 4-chloro-3-isobutyl-but-3-en-2-one (31.6 g) as a dark brown oil; LC-MS: $t_R$=0.97 min.

c) KOtBu (44.2 g, 394 mmol) is added portionwise to ethanol (200 mL). The mixture is stirred for 30 min at 20° C. to dissolve all KOtBu. Mercapto-acetic acid ethyl ester (47.3 g, 394 mmol) is added and the temperature is maintained at 20° C. This solution is slowly added at 20° C. to a solution of the crude 4-chloro-3-isobutyl-but-3-en-2-one (31.6 g, 197 mmol) in THF (350 mL). The mixture is stirred at rt for 15 h before sodium ethylate (13.4 g, 197 mmol) is added and stirring is continued at reflux for 1 h. The mixture is cooled to rt, and the solvents are evaporated on a rotavap. The residue is diluted with diethyl ether (500 mL), washed with 1 M aq. NaH$_2$PO$_4$ (200 mL), 1 N aq. NaOH (2×100 mL), sat. aq. NaHCO$_3$ (35 mL) containing 10% aq. NaOCl (15 mL) and brine (100 mL), dried over Na$_2$SO$_4$, filtered and evaporated. The resulting residue (36.3 g) is dissolved in EtOH (250 mL), 2 N aq. LiOH (100 mL) is added, and the mixture is stirred at rt for 48 h before it is extracted with diethyl ether (1×400 mL, 2×150 mL). The organic extracts are washed with 1 N aq. NaOH (3×100 mL). The aq. extracts are carefully acidified with 25% aq. HCl and then extracted with DCM (3×150 mL). The combined DCM extracts are dried over MgSO$_4$, filtered and evaporated. The crude product is purified by crystallisation from acetonitrile (150 mL) at 4° C. to give 4-isobutyl-3-methyl-thiophene-2-carboxylic acid (16.0 g) as a beige-brown crystalline powder; LC-MS: $t_R$=0.95 min; $^1$H NMR (CD$_3$OD): δ 7.21 (s, 1H), 2.43 (s, 3H), 2.42 (d, J=7.0 Hz, 2H), 1.83 (m, J=7.0 Hz, 1H), 0.92 (d, J=7.0 Hz, 6H).

Intermediate A4

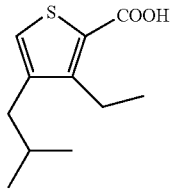

To a solution of 4-isobutyl-3-methyl-thiophene-2-carboxylic acid (991 mg, 5.0 mmol) in THF (30 mL), tert.-BuLi (7.3 mL, 11 mmol, 1.5 M in pentane) is slowly added at −78° C. The mixture is stirred at −78° C. for 1 h, then iodomethane (1.6 mL, 25.7 mmol) is added. The mixture is stirred and is allowed to warm to rt over a period of 15 h before the reaction is quenched with 1 N aq. HCl (50 mL) and extracted with DCM (1×100 mL, 2×50 mL). The combined organic extracts are dried (MgSO$_4$), filtered and evaporated. The residue is purified by CC on silica gel eluting with a gradient of EA in hexane to give 3-ethyl-4-isobutyl-thiophene-2-carboxylic acid (325 mg) as a yellow solid; LC-MS: $t_R$=0.98 min, $^1$H NMR (CD$_3$OD): δ 7.22 (s, 1H), 2.94 (q, J=7.6 Hz, 2H), 2.42 (d, J=7.0 Hz, 2H), 1.86 (hept, J=7.0 Hz, 1H), 1.11 (t, J=7.6 Hz, 3H), 0.93 (d, J=7.0 Hz, 6H).

Intermediate A5

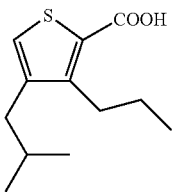

4-Isobutyl-3-propyl-thiophene-2-carboxylic acid is prepared in analogy to Intermediate A4; LC-MS: $t_R$=1.02 min, $^1$H NMR (CD$_3$OD): δ 7.20 (s, 1H), 2.92-2.86 (m, 2H), 2.42 (d, J=7.0 Hz, 2H), 1.92-1.76 (m, 1H), 1.58-1.45 (m, 2H), 0.95 (t, J=7.6 Hz, 3H), 0.94 (d, J=7.0 Hz, 6H).

Intermediate A6

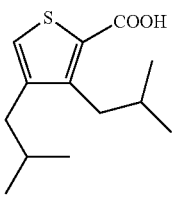

3,4-Diisobutyl-thiophene-2-carboxylic acid is prepared in analogy to Intermediate A4; LC-MS: $t_R$=1.04 min, $^1$H NMR (CD$_3$OD): δ 7.24 (s, 1H), 2.86 (d, J=6.9 Hz, 2H), 2.43 (d, J=7.5 Hz, 2H), 1.96-1.78 (m, 2H), 0.93 (d, J=6.2 Hz, 6H), 0.89 (d, J=6.9 Hz, 6H).

Intermediate A7

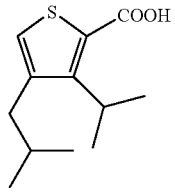

a) To a slurry of Mg turnings (3.89 g, 160 mmol) in dry diethyl ether (150 mL), a solution of isoamylbromide (24.59 g, 163 mmol) in diethyl ether (20 mL) is slowly added. As soon as the reaction starts, the mixture is cooled if necessary with a water bath. After complete addition, the mixture is stirred for 30 min, and is then added slowly to a cooled (0° C.) mixture of isobutyronitrile (34.65 g, 501 mmol) and CuBr (1.15 g, 8.0 mmol) in diethyl ether (50 mL) and THF (50 mL). After complete addition (30 min) the mixture is stirred at rt for 1 h before 1 N aq. NaH$_2$PO$_4$ (50 mL) and 1N aq. HCl (100 mL) is added. Stirring is continued at rt for 15 min. The phases are separated and the aq. phase is extracted with additional diethyl ether (100 mL). The combined organic extracts are washed with aq. 1N aq. HCl (2×50 mL), sat. aq. NH$_4$Cl/sat. aq. NaHCO$_3$ 1:1 (2×50 mL) and brine (50 mL), dried over Na$_2$SO$_4$, filtered and evaporated to give crude 2,6-dimethyl-heptan-3-one (20.1 g) as an oil.

b) To a solution of KOtBu (15.6 g, 139 mmol) in THF (200 mL) is added ethylformate (27.4 g, 370 mmol). During the addition, the mixture is cooled with a water bath to 10° C. Strong gas evolution occurs. The mixture is stirred until the gas evolution ceases (5 min) and is then cooled to −5° C. To this mixture a solution of 2,6-dimethyl-heptan-3-one (20 g, 141 mmol) and ethylformate (13.7 g, 185 mmol) in THF (20 mL) is added slowly during 30 min. The reaction mixture is stirred for 2 h and allowed to slowly warm to rt. The reaction is diluted with diethyl ether (200 mL) and washed with 1 N aq. HCl (2×100 mL). The organic extract is dried (Na$_2$SO$_4$), filtered and evaporated to give 1-hydroxy-2-isobutyl-4-methyl-pent-1-en-3-one (7.35 g) as a brown resin; LC-MS: $t_R$=0.91 min, [M+1]=171.21.

c) Over a period of 20 min, a solution of oxalylchloride (6.5 mL, 9.6 g, 75.6 mmol) in chloroform (10 mL) is added slowly to a solution of 1-hydroxy-2-isobutyl-4-methyl-pent-1-en-3-one (7.35 g, 43.2 mmol) in chloroform (100 mL) cooled to −10° C. The mixture is stirred for further 30 min, quenched with ice (100 g) and 1 N aq. NaOH (100 mL). When the quite violent gas evolution ceases the phases are separated. The organic phase is washed with 1 N aq. NaOH (3×75 mL) and 1 N aq. NaH$_2$PO$_4$ (75 mL), dried (MgSO$_4$), filtered and evaporated to give crude 1-chloro-2-isobutyl-4-methyl-pent-1-en-3-one (14.2 g) as a brown oil.

d) Mercapto-acetic acid ethyl ester (9.86 g, 82.1 mmol) is slowly added to a solution of KOtBu (9.50 g, 84.7 mmol) in ethanol (50 mL) cooled to 10-15° C. The mixture is diluted with THF (100 mL) before a solution of the crude 1-chloro-2-isobutyl-4-methyl-pent-1-en-3-one (corresponds to 8.1 g, 43 mmol) in THF (50 mL) is added. The reaction mixture is stirred at 40° C. for 15 h, then at reflux for further 20 h, and at 35° C. for 48 h. The mixture is diluted with ether (300 mL) and washed with 1N aq. NaOH (3×100 mL), 1 M aq. KHSO$_4$ (100 mL) and brine (100 mL). The organic phase is dried (Na$_2$SO$_4$), filtered and evaporated. The resulting residue is dissolved in ethanol (30 mL), 2 N aq. LiOH (30 mL) is added, and the mixture is stirred at reflux for 48 h. The mixture is extracted with diethyl ether, then the aq. phase is acidified with 25% aq. HCl and extracted with DCM. The organic extracts are dried (MgSO$_4$), filtered and evaporated. The brown oil is diluted in acetonitrile (5 mL) and allowed to crystallize at 4° C. The crystalline material is collected, washed with acetonitrile and dried to afford pure 4-isobutyl-3-isopropyl-thiophene-2-carboxylic acid (98 mg) as pale yellow crystals; $^1$H NMR (CD$_3$OD): δ 7.16 (s, 1H), 3.68 (hept, J=7.0 Hz, 1H), 2.48 (d, J=7.6 Hz, 2H), 1.84 (hept, J=7.0 Hz, 1H), 1.34 (d, J=7.0 Hz, 6H), 0.92 (d, J=6.4 Hz, 6H).

Intermediate A8

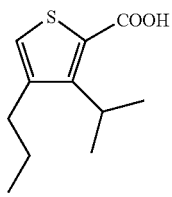

a) 1-Chloro-4-methyl-2-propyl-pent-1-en-3-one is prepared starting from 2-methyl-heptan-3-one in analogy to the preparation of Intermediate A7.

b) 1-Chloro-4-methyl-2-propyl-pent-1-en-3-one (29.7 g, 170 mmol) is reacted with mercaptoacetic acid ethyl ester (40.9 g, 340 mmol) in analogy to the procedure given for Intermediate A7 to give 3-isopropyl-4-propyl-thiophene-2-carboxylic acid (11.0 g) as colourless crystals; $^1$H NMR (CD$_3$OD): δ 7.21 (s, 1H), 3.83 (hept, J=7.0 Hz, 1H), 2.60 (t, J=7.6 Hz, 2H), 1.70-1.56 (m, 2H), 1.33 (d, J=7.6 Hz, 6H), 0.99 (t, J=7.6 Hz, 3H).

Intermediate A9

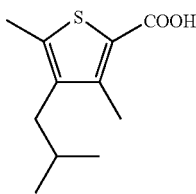

4-Isobutyl-3,5-dimethyl-thiophene-2-carboxylic acid is prepared from 4-isobutyl-5-methyl-thiophene-2-carboxylic acid in analogy to Intermediate A2; LC-MS: t$_R$=0.97 min, [M+1+CH$_3$CN]=254.26; $^1$H NMR (CDCl$_3$): δ 2.46 (s, 3H), 2.39 (s, 3H), 2.36 (d, J=7.0 Hz, 2H), 1.78 (hept, J=7.0 Hz, 1H), 0.91 (d, J=7.0 Hz, 6H).

Intermediate B1

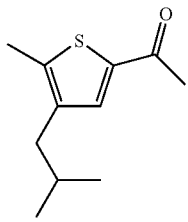

1-(4-Isobutyl-5-methyl-thiophen-2-yl)ethanone is obtained by treating 4-isobutyl-5-methyl-thiophene-2-carboxylic acid with methyllithium in analogy to the procedure described for Intermediate B2; LC-MS: t$_R$=1.02 min, [M+1]=197.01.

Intermediate B2

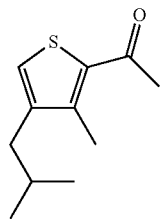

To a solution of 4-isobutyl-3-methyl-thiophene-2-carboxylic acid (2.44 g, 12.3 mmol) in diethyl ether (50 mL), a solution of methyllithium (23.1 mL, 1.6 M solution in diethyl ether) is slowly added at 20-23° C. The resulting suspension is stirred at rt for 30 min before another portion of methyllithium (2.3 mL) is added. Stirring is continued for further 30 min before the mixture is poured into vigorously stirred 1 N. aq. NH$_4$Cl (400 mL). The organic phase is separated and the aq. phase is extracted again with diethyl ether. The combined organic extracts are dried over Na$_2$SO$_4$, filtered and evaporated to leave 1-(4-isobutyl-3-methyl-thiophen-2-yl)ethanone (2.34 g) as pale yellow oil; LC-MS: t$_R$=1.03 min, [M+1]= 197.20; $^1$H NMR (CDCl$_3$): δ7.08 (s, 1H), 2.52 (s, 3H), 2.46 (s, 3H), 2.42 (d, J=7.0 Hz, 2H), 1.82 (m, J=7.0 Hz, 1H), 0.92 (d, J=6.4 Hz, 6H).

Intermediate B3

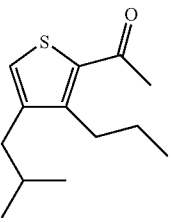

1-(4-Isobutyl-3-propyl-thiophen-2-yl)ethanone is obtained by treating 4-isobutyl-3-propyl-thiophene-2-carboxylic acid with methyllithium in analogy to the procedure described for Intermediate B2; LC-MS: t$_R$=1.11 min, [M+1]= 225.30; $^1$H NMR (CDCl$_3$): δ 7.08 (s, 1H), 2.92-2.85 (m, 2H), 2.51 (s, 3H), 2.42 (d, J=7.0 Hz, 2H), 1.86 (hept, J=7.0 Hz, 1H), 1.55-1.43 (m, 2H), 0.99 (t, J=7.0 Hz, 3H), 0.94 (d, J=7.0 Hz, 6H).

Intermediate B4

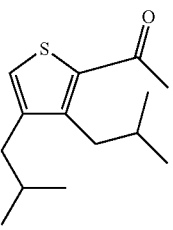

1-(3,4-Diisobutyl-thiophen-2-yl)-ethanone is obtained by treating 3,4-diisobutyl-thiophene-2-carboxylic acid with methyllithium in analogy to the procedure described for Intermediate B2; LC-MS: t$_R$=1.12 min, [M+1]=239.22; $^1$H NMR (CDCl$_3$): δ 7.08 (s, 1H), 2.84 (d, J=7.0 Hz, 2H), 2.50 (s, 3H), 2.41 (d, J=6.4 Hz, 2H), 1.94-1.78 (m, 2H), 0.93 (d, J=6.4 Hz, 6H), 0.90 (d, J=6.4 Hz, 6H).

Intermediate B5

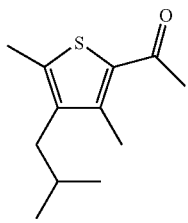

1-(4-Isobutyl-3,5-dimethyl-thiophen-2-yl)ethanone is obtained by treating 4-isobutyl-3,5-dimethyl-thiophene-2-carboxylic acid with methyllithium in analogy to the procedure described for Intermediate B2; LC-MS: $t_R$=1.07 min, [M+1]=211.22; $^1$H NMR (CDCl$_3$): δ 0.90 (d, J=6.4 Hz, 6H), 1.77 (hept, J=7.0 Hz, 1H), 2.37 (d, J=7.3 Hz, 2H), 2.39 (s, 3H), 2.45 (s, 3H), 2.47 (s, 3H).

Intermediate C1

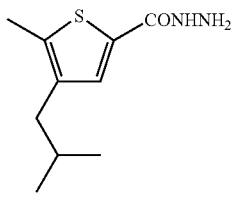

Intermediate A1 (10.0 g, 50.4 mmol) is dissolved in CHCl$_3$ (100 mL) and thionylchloride (15 mL) is added at rt. The mixture is stirred at reflux for 2 h. The mixture is evaporated to provide the crude acid chloride (11.2 g). A part of this material (6.5 g, 30 mmol) is dissolved in DCM (200 mL) and then added to a cold (0° C.) solution of hydrazine (90 mL, 1 M in THF). The mixture is stirred and warmed to rt over a period of 15 h before it is diluted with diethyl ether (150 mL) and washed with 1M aq. HCl (75 mL, then 5×50 mL). The combined aq. extracts are washed with ether (50 mL), basified with 33% aq. KOH and extracted with DCM (5×50 mL). The organic DCM extracts are dried over Na$_2$SO$_4$, filtered and evaporated to give 4-isobutyl-5-methyl-thiophene-2-carboxylic acid hydrazide (6.24 g) as a white solid; LC-MS: $t_R$=0.75 min, [M+1]=213.12; $^1$H NMR (D$_6$-DMSO): δ 0.85 (d, J=6.7 Hz, 6H), 1.76 (hept, J=6.7 Hz, 1H), 2.26-2.34 (m, 5H), 4.34 (s, 2H), 7.41 (s, 1H), 9.52 (s, 1H).

Intermediate C2

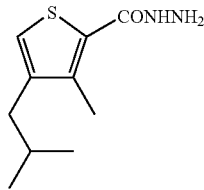

4-Isobutyl-3-methyl-thiophene-2-carboxylic acid hydrazide is prepared in analogy to Intermediate C1 from Intermediate A3; LC-MS: $t_R$=0.75 min, [M+1]=213.20; $^1$H NMR (CDCl$_3$): 0.91 (d, J=6.4 Hz, 6H), 1.81 (hept, J=6.4 Hz, 1H), 2.38 (d, J=6.1 Hz, 2H), 2.40 (s, 3H), 4.04 (d, J=2.3 Hz, 2H), 6.94 (s, 1H), 7.03 (s br, 1H).

Intermediate C3

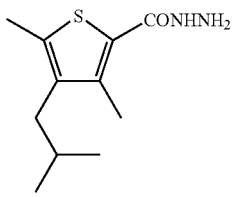

4-Isobutyl-3,5-dimethyl-thiophene-2-carboxylic acid hydrazide is prepared in analogy to Intermediate C1 from Intermediate A9; LC-MS: $t_R$=0.78 min, [M+1]=227.03.

Intermediate D1

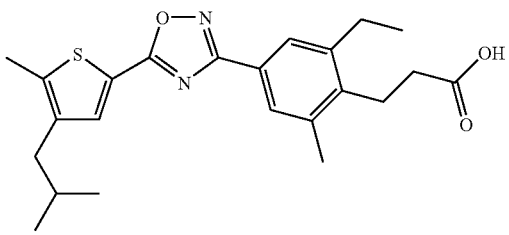

To a solution of 4-isobutyl-5-methyl-thiophene-2-carboxylic acid (126 mg, 637 µmol) in DCM (5 mL), DIPEA (249 mg, 1.93 mmol) is added followed TBTU (202 mg, 628 µmol). The mixture is stirred at rt for 30 min before 3-[2-ethyl-4-(N-hydroxycarbamimidoyl)-6-methyl-phenyl]-propionic acid (159 mg, 637 µmol) is added. The mixture is stirred at rt for 16 h before it is diluted with DCM, washed with 1 N aq. HCl solution, dried over Na$_2$SO$_4$, filtered and concentrated. The residue is dissolved in toluene (20 mL) and the reaction mixture is stirred at 110° C. for 18 h. The solvent is evaporated and the crude product is purified by CC on silica gel eluting with DCM containing 5% of methanol to give 3-{2-ethyl-4-[5-(4-isobutyl-5-methyl-thiophen-2-yl)-[1,2,4]oxadiazol-3-yl]-6-methyl-phenyl}-propionic acid (41 mg) as a beige solid; LC-MS: $t_R$=1.17 min, [M+1]$^+$=413.30; $^1$H NMR (CDCl$_3$): δ 0.94 (d, J=6.4 Hz, 6H), 1.30 (t, J=7.6 Hz, 3H), 1.84-1.96 (m, 1H), 2.43 (s, 3H), 2.45 (s, 3H), 2.46-2.60 (m, 4H), 2.75 (q, J=7.3 Hz, 2H), 3.02-3.12 (m, 2H), 7.66 (s, 1H), 7.79 (s, 1H), 7.81 (s, 1H).

Intermediate D2

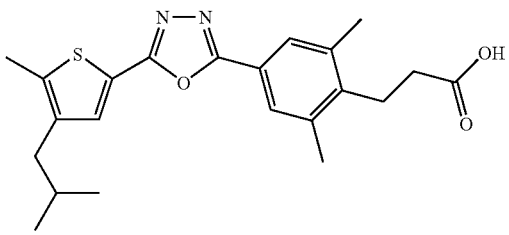

To a solution of 4-(2-tert-butoxycarbonyl-ethyl)-3,5-dimethyl-benzoic acid (763 mg, 3.59 mmol) in DCM (18 mL), DIPEA (542 mg, 4.20 mmol) is added followed by TBTU (1.27 g, 3.95 mmol). The mixture is stirred for 15 min before Intermediate C1 (1.0 g, 3.59 mmol) is added. Stirring is continued at rt for 16 h. The mixture is diluted with diethyl ether, washed with 1 N aq. NaOH solution, then 1 N aq. HCl solution followed by brine, dried over Na₂SO₄, and filtered. The solvent is evaporated to give 3-{4-[N'-(4-isobutyl-5-methyl-thiophene-2-carbonyl)-hydrazinocarbonyl]-2,6-dimethyl-phenyl}-propionic acid (1.66 g) as a colourless foam; LC-MS: $t_R$=1.09 min, [M+1]=473.48. To a solution of this material in THF (15 mL) Burgess reagent (1.26 g, 5.27 mmol) is added. The mixture is heated to 110° C. for 3 min in a microwave oven. The mixture is cooled to rt, diluted with diethyl ether and washed with 1 N aq. NaOH. The organic extract is dried over Na₂SO₄, filtered and concentrated to give 3-{4-[5-(4-isobutyl-5-methyl-thiophen-2-yl)-[1,3,4]oxadiazol-2-yl]-2,6-dimethyl-phenyl}-propionic acid methyl ester (1.26 g) as a yellow oil that slowly solidifies; LC-MS: $t_R$=1.24 min, [M+1]=455.21. A suspension of this ester in formic acid (20 mL) is stirred at rt for 3 h. The formic acid is evaporated and the residue is purified by CC on silica gel eluting with DCM containing 5% of methanol to give 3-{4-[5-(4-isobutyl-5-methyl-thiophen-2-yl)-[1,3,4]oxadiazol-2-yl]-2,6-dimethyl-phenyl}-propionic acid as a pale yellow solid; LC-MS: $t_R$=1.07 min, [M+1]=399.16.

Intermediate D3

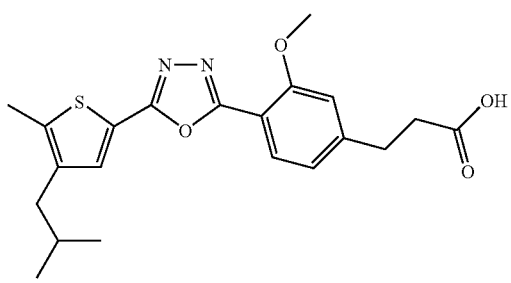

3-{4-[5-(4-Isobutyl-5-methyl-thiophen-2-yl)-[1,3,4]oxadiazol-2-yl]-3-methoxy-phenyl}-propionic acid is prepared in analogy to Intermediate D2 starting from Intermediate C1 and 4-(2-tert-butoxycarbonyl-ethyl)-2-methoxy-benzoic acid; LC-MS: $t_R$=1.18 min, [M+1]=415.37.

Intermediate D4

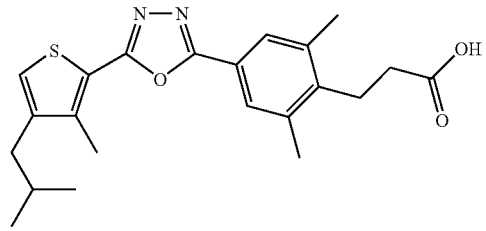

3-{4-[5-(4-Isobutyl-3-methyl-thiophen-2-yl)-[1,3,4]oxadiazol-2-yl]-2,6-dimethyl-phenyl}-propionic acid is prepared in analogy to Intermediate D2 starting from Intermediate C2 and 4-(2-tert-butoxycarbonyl-ethyl)-2-methoxy-benzoic acid; LC-MS: $t_R$=1.10 min, [M+1]=399.41.

Intermediate D5

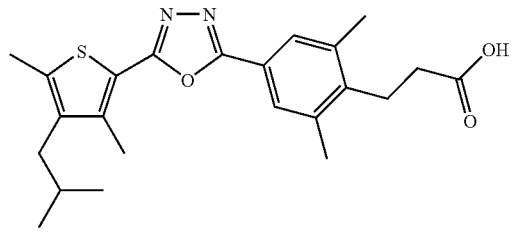

3-{4-[5-(4-Isobutyl-3,5-dimethyl-thiophen-2-yl)-[1,3,4]oxadiazol-2-yl]-2,6-dimethyl-phenyl}-propionic acid is prepared in analogy to Intermediate D2 starting from Intermediate C3 and 4-(2-tert-butoxycarbonyl-ethyl)-2-methoxy-benzoic acid; LC-MS: $t_R$=1.13 min, [M+1]=413.39.

Intermediate E1

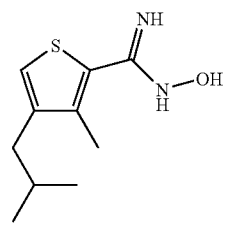

a) 4-Isobutyl-3-methyl-thiophene-2-carbonitrile is obtained by reacting 4-chloro-3-isobutyl-but-3-en-2-one with thioacetic acid S-cyanomethyl ester in the presence of NaOEt as described in step c) for Intermediate A3. The crude product is purified by CC on silica gel eluting with heptane:EA 6:1; LC-MS: $t_R$=1.03 min; ¹H NMR (CDCl₃): δ 0.92 (d, J=6.4 Hz, 12H), 1.78-1.90 (m, 1H), 2.34 (s, 3 H), 2.40 (d, J=7.3 Hz, 2 H), 7.11 (s, 1 H).

b) To a solution of 4-isobutyl-3-methyl-thiophene-2-carbonitrile (2.10 g, 11.7 mmol) in methanol (50 mL), NaHCO₃ (1.38 g, 16.4 mmol) followed by hydroxylamine hydrochloride (977 mg, 14.1 mmol) is added. The mixture is stirred at 60° C. for 20 h before it is filtered. The solvent of the filtrate is evaporated and the remaining residue is dried under HV go give N-hydroxy-4-isobutyl-3-methyl-thiophene-2-carboxamidine (3.0 g) as a yellow solid; LC-MS: $t_R$=0.67 min.

4,N-Dihydroxy-3,5-dimethyl-benzamidine

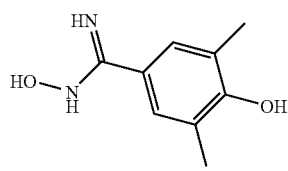

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR (CD$_3$OD): δ 7.20 (s, 2H), 2.20 (s, 6H).

3-Ethyl-4,N-dihydroxy-5-methyl-benzamidine

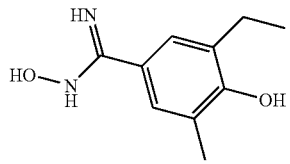

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

3,5-Diethyl-4,N-dihydroxy-benzamidine

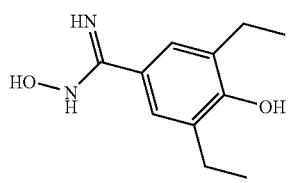

The title compound is prepared from commercially available 2,6-diethylaniline following literature procedures (G. G. Ecke, J. P. Napolitano, A. H. Filbey, A. J. Kolka, *J. Org. Chem.* 22 (1957) 639-642; and literature cited for 3-ethyl-4,N-dihydroxy-5-methyl-benzamidine).

4-Allyloxy-N-hydroxy-2-methoxy-benzamidine

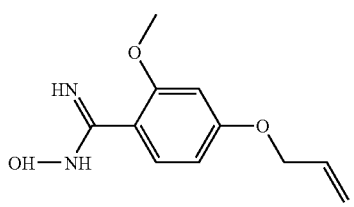

The title compound is prepared from commercially available 4-hydroxy-2-methoxy-benzaldehyde following literature procedures (references cited for 3-Ethyl-4,N-dihydroxy-5-methyl-benzamidine); LC-MS: $t_R$=0.64 min, [M+1]$^+$=223.24; $^1$H NMR (D$_6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

3-Chloro-4,N-dihydroxy-5-methyl-benzamidine

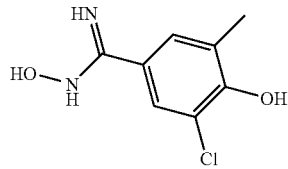

a) To a solution of 2-chloro-6-methyl-phenol (10.0 g, 70 mmol) in trifluoroacetic acid (30 mL), hexamethylene tetraamine (9.81 g, 70 mmol) is added portionwise. The mixture is heated to 70° C. and stirred for 18 h. The mixture is cooled with an ice bath, then stirred at rt for 72 h. The mixture is diluted with water and extracted three times with diethyl ether. The combined organic extracts are dried over Na$_2$SO$_4$, filtered and concentrated. The crude product is purified by CC on silica gel eluting with heptane:EA 4:1 to give 3-chloro-4-hydroxy-5-methyl-benzaldehyde (2.79 g) as a beige solid, LC-MS: $t_R$=0.82 min.

b) 3-Chloro-4,N-dihydroxy-5-methyl-benzamidine is prepared from the above aldehyde following literature procedures (A. K. Chakraborti, G. Kaur, *Tetrahedron* 55 (1999) 13265-13268; E. Meyer, A. C. Joussef, H. Gallardo, *Synthesis* 2003, 899-905), LC-MS: $t_R$=0.48 min, [M+1]=201.17; $^1$H NMR (CD$_3$OD): δ 2.21 (s, 3 H), 7.22 (d, J=2.1 Hz, 1 H), 7.37 (d, J=2.1 Hz, 1 H).

3-Chloro-4,N-dihydroxy-5-methoxy-benzamidine

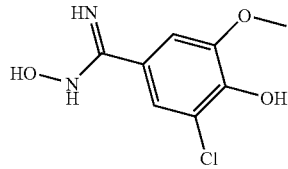

3-Chloro-4,N-dihydroxy-5-methoxy-benzamidine is prepared from 3-chloro-4-hydroxy-5-methoxy benzaldehyde following literature procedures (A. K. Chakraborti, G. Kaur, *Tetrahedron* 55 (1999) 13265-13268; E. Meyer, A. C. Joussef, H. Gallardo, *Synthesis* 2003, 899-905), LC-MS: $t_R$=0.48 min, [M+1]=217.21; $^1$H NMR (CD$_3$OD): δ 3.90 (s, 3H), 7.16 (d, J=1.8 Hz, 1H), 7.23 (d, J=1.8 Hz, 1 H).

4-(2-tert-Butoxycarbonyl-ethyl)-3,5-dimethyl-benzoic acid

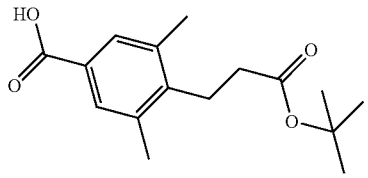

a) To an ice-cooled solution of 4-hydroxy-3,5-dimethyl-benzoic acid methyl ester (7.52 g, 41.7 mmol) in DCM (250 mL) and pyridine (10 mL), trifluoromethanesulfonic acid anhydride (13.0 g, 45.9 mmol) is added over a period of 20 min. Upon complete addition, the ice bath is removed and the reaction is stirred for further 1 h at rt. The mixture is diluted with DCM (150 mL), washed with 10% aq. citric acid solution followed by brine, dried over MgSO$_4$, filtered and evaporated. The residue is purified by flash chromatography on silica gel eluting with heptane:EA 9:1 to give 3,5-dimethyl-4-trifluoromethanesulfonyloxy-benzoic acid methyl ester (11.8 g) as colourless fine needles; LC-MS: $t_R$=1.08 min.

b) To a stirred solution of the above triflate (11.8 g, 37.8 mmol) in dry DMF (155 mL) is sequentially added triethylamine (7.6 g, 75.6 mmol), tert.-butyl acrylate (48.4 g, 378 mmol), DPPP (779 mg, 1.89 mmol) and Pd(OAc)$_2$ (424 mg, 1.89 mmol) under nitrogen. The mixture is stirred at 115° C. for 18 h before another portion of DPPP (160 mg, 0.39 mmol) and Pd(OAc)$_2$ (80 mg, 0.36 mmol) is added. Stirring is continued for 4 h at 115° C. before the mixture is cooled to rt, diluted with diethyl ether (350 mL) and washed with 1 N aq. HCl, followed by sat. aq. NaHCO$_3$ solution. The organic extract is dried over MgSO$_4$, filtered and evaporated. The residue is purified by flash chromatography on silica gel eluting with heptane:EA 4:1 to give 4-(2-tert-butoxycarbonyl-vinyl)-3,5-dimethyl-benzoic acid methyl ester (11.21 g) as a colourless solid; LC-MS: $t_R$=1.09 min.

c) To a solution of 4-(2-tert-butoxycarbonyl-vinyl)-3,5-dimethyl-benzoic acid methyl ester (11.2 g, 38.6 mmol) in ethanol (50 mL) and THF (50 mL), Pd/C (1.0 g, 10% Pd) is added. The mixture is stirred for 16 h at rt under 2.5 bar of H$_2$. The catalyst is filtered off and the filtrate is concentrated and dried under HV to give 4-(2-tert-butoxycarbonyl-ethyl)-3,5-dimethyl-benzoic acid methyl ester (10.8 g) as a colourless oil; LC-MS: $t_R$=1.08 min.

d) To a solution of 4-(2-tert-butoxycarbonyl-ethyl)-3,5-dimethyl-benzoic acid methyl ester (10.8 g, 37.0 mmol) in ethanol (100 mL) a 2 M aq. solution of LiOH (50 mL) is added at 0° C. The turbid mixture is stirred at 0° C. for 30 min, then at rt for 4 h. The mixture is diluted with 10% aq. citric acid solution and extracted three times with diethyl ether. The combined organic extracts are dried over MgSO$_4$, filtered and concentrated. The solid residue is suspended in diethyl ether/heptane, stirred at rt, and filtered. The slurry procedure in diethyl ether/heptane is repeated. The solid material is collected and dried under HV to give 4-(2-tert-butoxycarbonyl-ethyl)-3,5-dimethyl-benzoic acid (5.09 g) as a white crystalline powder; LC-MS: $t_R$=0.95 min, [M+1]$^+$=279.14; $^1$H NMR (CDCl$_3$): δ 1.47 (s, 9 H), 2.30-2.40 (m, 2 H), 2.39 (s, 6 H), 2.94-3.03 (m, 2 H), 7.75 (s, 2 H).

4-(2-tert-Butoxycarbonyl-ethyl)-2-methoxy-benzoic acid

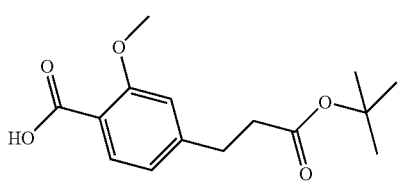

The title compound is prepared in analogy to 4-(2-tert-butoxycarbonyl-ethyl)-3,5-dimethyl-benzoic acid starting from 4-hydroxy-2-methoxy-benzoic acid methyl ester; LC-MS: $t_R$=0.94 min, [M+1]$^+$=281.23; $^1$H NMR (CDCl$_3$): δ 1.34 (s, 9 H), 2.40-2.47 (m, 2 H), 2.76-2.85 (m, 2 H), 3.83 (s, 3 H), 7.21-7.28 (dd, J=7.6, 3.2 Hz, 1 H), 7.41-7.49 (m, 2 H).

3-[2-Ethyl-4-(N-hydroxycarbamimidoyl)-6-methyl-phenyl]-propionic acid

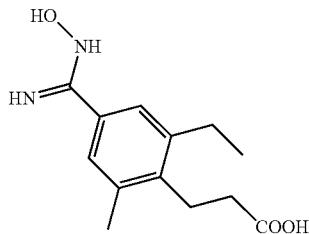

a) To an ice-cooled solution of 5-ethyl-4-hydroxy-3-methylbenzaldehyde (10.0 g, 60.9 mmol) in DCM (50 mL) and pyridine (15 mL), trifluoromethanesulfonic acid anhydride (18.9 g, 67 mmol) is added over a period of 20 min. Upon complete addition, the ice bath is removed and the reaction is stirred for further 2 h at rt. The mixture is diluted with DCM (150 mL), washed three times with water, dried over MgSO$_4$, filtered and evaporated. The residue is purified by flash chromatography on silica gel eluting with heptane:EA 9:1 to give trifluoro-methanesulfonic acid 2-ethyl-4-formyl-6-methyl-phenyl ester (10.75 g) as a pale yellow oil; LC-MS: $t_R$=1.07 min; $^1$H NMR (CDCl$_3$): δ 9.98 (s, 1H), 7.70 (s, 1H), 7.66 (s, 1H), 2.85 (q, J=10.1 Hz, 2H), 2.48 (s, 3H), 1.30 (t, J=10.2 Hz, 3H).

b) To a stirred solution of the above triflate (10.7 g, 36.1 mmol) in dry DMF (75 mL) is sequentially added triethylamine (7.3 g, 72.2 mmol), methyl acrylate (31.1 g, 361 mmol), DPPP (819 mg, 1.99 mmol) and Pd(OAc)$_2$ (405 mg, 1.81 mmol) under nitrogen. The mixture is stirred at 115° C. for 5 h, cooled to rt, diluted with diethyl ether (350 mL) and washed twice with 1 N aq. HCl and once with sat. aq. NaHCO$_3$ solution. The organic extract is dried over MgSO$_4$, filtered and evaporated. The residue is purified by flash chromatography on silica gel eluting with heptane:EA 19:1 to give 3-(2-ethyl-4-formyl-6-methyl-phenyl)-acrylic acid methyl ester (5.93 g) as a colourless liquid; LC-MS: $t_R$=0.99 min.

c) A suspension of 3-(2-ethyl-4-formyl-6-methyl-phenyl)-acrylic acid methyl ester (5.93 g, 25.53 mmol) in methanol (140 mL) and 2 N aq. NaOH (45 mL) is stirred at rt for 1 h. The methanol is evaporated and the aq. solution is extracted twice with DCM. The aq. layer is acidified with 37% aq. HCl. The precipitate that forms is collected, washed with water and dried. The product is further purified by recrystallisation from EA (100 mL) to give 3-(2-ethyl-4-formyl-6-methyl-phenyl)-acrylic acid (4.2 g) as yellow crystals; LC-MS: $t_R$=0.87 min.

d) To a solution of 3-(2-ethyl-4-formyl-6-methyl-phenyl)-acrylic acid (2.75 g, 12.6 mmol) and DIPEA (1.8 g, 13.8 mmol) in ethanol (80 mL), Pd/C (275 mg, 10% Pd, moistened with 50% water) is added. The mixture is stirred for 16 h at rt under 1 atm of H$_2$. The catalyst is filtered off and the filtrate is concentrated. The residue is dissolved in EA, washed with 2 N aq. HCl, followed by 1 N aq. HCl and brine. The organic extract is dried over Na$_2$SO$_4$, filtered and evaporated to give 3-(2-ethyl-4-hydroxymethyl-6-methyl-phenyl)-propionic acid (2.8 g) as a white solid; LC-MS: $t_R$=0.76 min.

e) A solution of 3-(2-ethyl-4-hydroxymethyl-6-methyl-phenyl)-propionic acid (2.8 g, 12.6 mmol) in acetic acid (50 mL) is treated with MnO$_2$ (3.9 g, 45.4 mmol) and the resulting mixture is stirred at 80° C. for 4 h. The mixture is filtered and the filtrate is concentrated. The crude product is purified by CC on silica gel eluting with DCM to give 3-(2-ethyl-4-formyl-6-methyl-phenyl)-propionic acid (1.76 g) as a beige solid; LC-MS: t$_R$=0.86 min.

f) A solution of 3-(2-ethyl-4-formyl-6-methyl-phenyl)-propionic acid (1.67 g, 7.58 mmol) and hydroxylamine hydrochloride (780 mg, 11.36 mmol) in 1-methyl-2-pyrrolidone is heated to 80° C. for 30 min in the microwave (300 W, active cooling during irradiation). The reaction mixture is diluted with diethyl ether and washed with water and brine. The organic extract is dried over Na$_2$SO$_4$, filtered and evaporated to give 3-(4-cyano-2-ethyl-6-methyl-phenyl)-propionic acid (1.55 g) as a beige solid; LC-MS: t$_R$=0.89 min, $^1$H NMR (D$_6$-DMSO): δ 12.25 (s, 1H), 7.45 (s, 2H), 2.91-2.84 (m, 2H), 2.67-2.59 (m, 2H), 2.35-2.30 (m, 5H), 1.14 (t, J=7.6 Hz, 3H).

g) Potassium tert. butoxide (2.71 g, 24.1 mmol) is carefully dissolved in methanol (25 mL). To this solution hydroxylamine hydrochloride (1.44 g, 20.7 mmol) followed by 3-(4-cyano-2-ethyl-6-methyl-phenyl)-propionic acid (1.50 g, 6.90 mmol) dissolved in methanol (7.5 mL) is added. The mixture is refluxed for 8 h and the solvent is evaporated. The residue is dissolved in 2 N aq. HCl and extracted with EA. The pH of the aq. phase is adjusted to pH 5 by adding sat. aq. NaHCO$_3$ and the mixture is extracted three times with EA. The combined organic extracts are dried over Na$_2$SO$_4$, filtered, evaporated and dried to give 3-[2-ethyl-4-(N-hydroxycarbamimidoyl)-6-methyl-phenyl]-propionic acid (1.4 g) as a white solid; LC-MS: t$_R$=0.60 min, [M+1]$^+$=251.17.

4-Benzyloxy-3,5-dimethyl-benzoic acid hydrazide

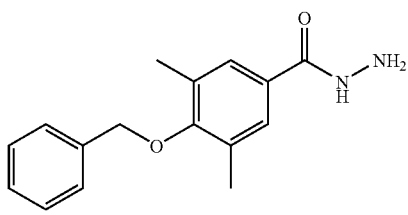

4-Benzyloxy-3,5-dimethyl-benzoic acid (5.37 g, 20.9 mmol) is dissolved in CHCl$_3$ (75 mL) and thionylchloride (10 mL) is added at rt. The mixture is stirred at reflux for 2 h. The mixture is evaporated to provide the crude acid chloride (5.62 g). A part of this material (2.75 g, 10 mmol) is dissolved in THF (10 mL) and cooled to −78° C. before it is treated with hydrazine (25 mL, 1 M solution in THF). The mixture is warmed to rt over a period of 15 h. The mixture is diluted with ether (150 mL) and washed with 1M aq. HCl (75 mL, then 5×50 mL). The combined aq. extracts are washed with ether (50 mL), basified with 33% aq. KOH and extracted with DCM (5×50 mL). The DCM extracts are dried over Na$_2$SO$_4$, filtered and evaporated to give 4-benzyloxy-3,5-dimethyl-benzoic acid hydrazide (1.29 g) as a white solid, LC-MS: t$_R$=0.78 min, [M+1]$^+$=271.19; $^1$H NMR (CDCl$_3$): δ 2.30 (s, 6 H), 3.86 (s br, 2H), 4.82 (s, 2 H), 7.33-7.49 (m, 7 H), 7.56 (s br, 1 H).

4-Benzyloxy-3-ethyl-5-methyl-benzoic acid

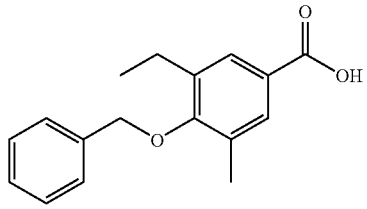

a) 3-Ethyl-4-hydroxy-5-methyl-benzaldehyde is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

b) To a suspension of K$_2$CO$_3$ (21 g, 152 mmol) in acetone (200 mL), 3-ethyl-4-hydroxy-5-methyl-benzaldehyde (5.0 g, 30.5 mmol) followed by benzyl bromide (7.87 g, 45.7 mmol) is added. The suspension is refluxed for 16 h before it is filtered. The filtrate is concetrated and the crude product is purified by CC on silica gel eluting with heptane:EA 4:1 to give 4-benzyloxy-3-ethyl-5-methyl-benzaldehyde (5.04 g) as colourless oil; LC-MS: t$_R$=1.09 min, [M+1]$^+$=255.25.

c) To a solution of 4-benzyloxy-3-ethyl-5-methyl-benzaldehyde (5.0 g, 19.7 mmol) in acetone (200 mL), KMnO$_4$ (4.66 g, 29.5 mmol) is added. The dark violet solution becomes slightly warm and turns dark brown. The mixture is stirred at rt for 90 min before the solvent is evaporated. The residue is treated with 10% aq. citric acid soluiton (200 mL) and brine (200 mL) and extracted four times with DCM (4×200 mL). The combined organic extracts are dried over MgSO$_4$, filtered and concentrated. The crude product is purified by CC on silica gel eluting with heptane:EA 1:1 to give 4-benzyloxy-3-ethyl-5-methyl-benzoic acid (3.70 g) as a white solid; LC-MS: t$_R$=0.98 min, [M+1+CH$_3$CN]$^+$=311.97.

Example 1

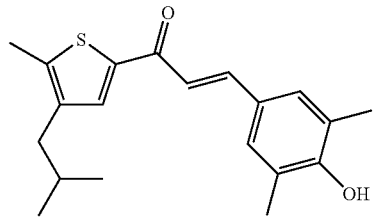

To a solution of 1-(4-isobutyl-5-methyl-thiophen-2-yl) ethanone (1.52 g, 7.74 mmol) and 3,5-dimethyl-4-hydroxy-benzaldehyde (1.75 g, 11.6 mmol) in ethanol (40 mL), 5 N HCl in isopropanol (10 mL) is added. The reaction mixture turns dark red to brownish black and a precipitate forms. The mixture is stirred at rt for 4 h before it is diluted with diethyl ether and washed with sat. aq. NaHCO$_3$:1 N aq. NaOH 1:1 (3×50 mL). The organic extract is dried over MgSO$_4$, filtered and evaporated. The crude product is purified by MPLC on reversed phase silica gel to give 3-(4-hydroxy-3,5-dimethyl-phenyl)-1-(4-isobutyl-5-methyl-thiophen-2-yl)-propenone (482 mg) as an almost black solid; LC-MS: $t_R$=1.12 min, [M+1]=329.10.

Example 2

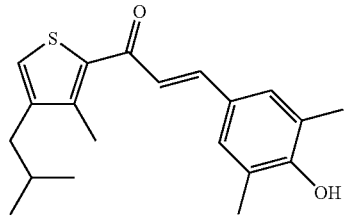

3-(4-Hydroxy-3,5-dimethyl-phenyl)-1-(4-isobutyl-3-methyl-thiophen-2-yl)-propenone is obtained as a yellow powder in analogy to Example 1 starting from 1-(4-isobutyl-3-methyl-thiophen-2-yl)-ethanone; LC-MS: $t_R$=1.13 min, [M+1]=329.20; $^1$H NMR (D$_6$-DMSO): δ 7.52 (s, 1H), 7.51 (d, J=15.2 Hz, 1H), 7.36 (s, 2H), 7.20 (d, J=15.8 Hz, 1H), 4.07 (s br, 1H), 2.45 (s, 3H), 2.42 (d, J=7.0 Hz, 2H), 2.18 (s, 6H), 1.82 (hept, J=7.0 1H), 0.88 (d, J=7.0 Hz, 6H).

Example 3

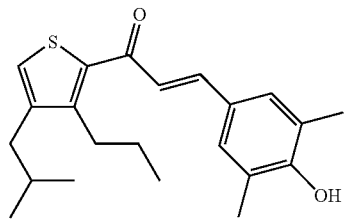

3-(4-Hydroxy-3,5-dimethyl-phenyl)-1-(4-isobutyl-3-propyl-thiophen-2-yl)-propenone is obtained as a yellow powder in analogy to Example 1 starting from 1-(4-isobutyl-3-propyl-thiophen-2-yl)-ethanone; LC-MS: $t_R$=1.16 min, [M+1]=357.27.

Example 4

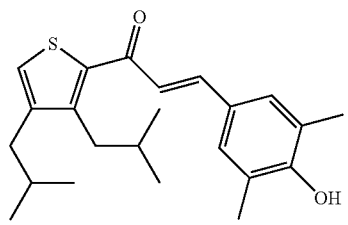

1-(3,4-Diisobutyl-thiophen-2-yl)-3-(4-hydroxy-3,5-dimethyl-phenyl)-propenone is obtained as a yellow solid in analogy to Example 1 starting from 1-(3,4-diisobutyl-thiophen-2-yl)-ethanone; LC-MS: $t_R$=1.18 min, [M+1]=371.29.

Example 5

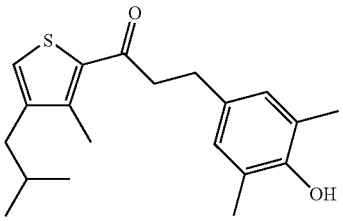

3-(4-Hydroxy-3,5-dimethyl-phenyl)-1-(4-isobutyl-3-methyl-thiophen-2-yl)-propan-1-one is obtained as on orange oil upon hydrogenation of 3-(4-hydroxy-3,5-dimethyl-phenyl)-1-(4-isobutyl-3-methyl-thiophen-2-yl)-propenone in analogy to Example 7; LC-MS: $t_R$=1.11 min, [M+1]=331.3.

Example 6

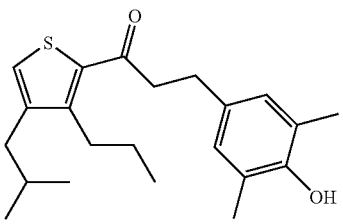

3-(4-Hydroxy-3,5-dimethyl-phenyl)-1-(4-isobutyl-3-propyl-thiophen-2-yl)-propan-1-one is prepared from 3-(4-hydroxy-3,5-dimethyl-phenyl)-1-(4-isobutyl-3-propyl-thiophen-2-yl)-propenone in analogy to Example 7; LC-MS: $t_R$=1.16 min, [M+1]=359.39.

Example 7

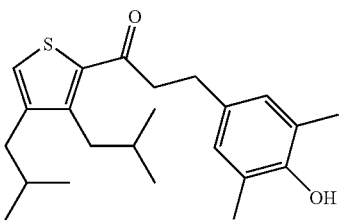

To a solution of 1-(3,4-diisobutyl-thiophen-2-yl)-3-(4-hydroxy-3,5-dimethyl-phenyl)-propenone (699 mg, 1.88 mmol) in methanol (15 mL) and THF (15 mL), Pd/C (150 mg, 10% Pd) is added. The slurry is stirred at rt under 3 bar of H$_2$. The mixture is filtered and the filtrate is evaporated. The crude product is purified by CC on silica gel eluting with heptane/EA 5:1 to 3:1 to give 1-(3,4-diisobutyl-thiophen-2-yl)-3-(4-hydroxy-3,5-dimethyl-phenyl)-propan-1-one (178 mg) as a brown oil; LC-MS: $t_R$=1.18 min, [M+1]=373.35; $^1$H NMR (CDCl$_3$): δ 7.08 (s, 1H), 6.85 (s, 2H), 4.77 (s br, 1H), 3.15-

3.06 (m, 2H), 2.96-2.83 (m, 4H), 2.43 (d, J=7.0 Hz, 2H), 2.23 (s, 6H), 1.96-1.80 (m, 2H), 0.94 (d, J=6.4 Hz, 6H), 0.91 (d, J=6.4 Hz, 6H).

Example 8

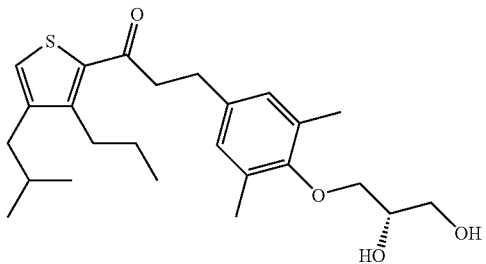

To a solution of 3-(4-hydroxy-3,5-dimethyl-phenyl)-1-(4-isobutyl-3-propyl-thiophen-2-yl)-propan-1-one (108 mg, 0.301 mmol) in isopropanol (5 mL), 3 N aq. NaOH (3 mL) followed by (S)-3-chloro-1,2-propanediol (167 mg, 1.51 mmol) is added. The mixture is stirred at 70° C. for 4 h. After 4, 5, 6, 7 and 8 h an additional portion of (S)-3-chloro-1,2-propanediol (5×97 mg, 0.878 mmol) is added. After the last addition, stirring is continued at 60° C. for 16 h. The mixture is diluted with water and extracted with diethyl ether. The organic extract is dried over $MgSO_4$, filtered and evaporated. The crude product is purified by prep. HPLC to give 3-[4-((S)-2,3-dihydroxy-propoxy)-3,5-dimethyl-phenyl]-1-(4-isobutyl-3-propyl-thiophen-2-yl)-propan-1-one (18 mg) as an almost colourless resin; LC-MS: $t_R$=1.09 min, [M+1]= 433.40; $^1$H NMR ($CDCl_3$): δ 7.08 (s, 1H), 6.87 (s, 2H), 4.11-4.03 (m, 1H), 3.90-3.70 (m, 4H), 3.14-3.06 (m, 2H), 2.94-2.82 (m, 4H), 2.60 (s br, 2H), 2.40 (d, J=7.0 Hz, 2H), 2.24 8s, 6H), 1.90-1.78 (m, 1H), 1.56-1.46 (m, 2H), 1.00 8t, J=7.0 Hz, 3H), 0.93 (d, J=6.4 Hz, 6H).

Example 9

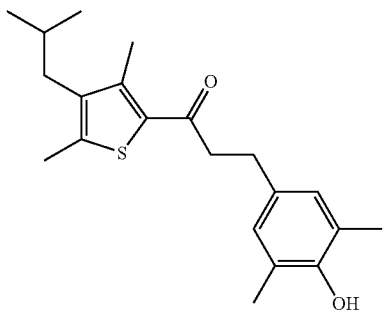

a) A mixture of acetylacetone (2.5 g, 25 mmol), $K_2CO_3$ (3.45 g, 25 mmol) and 3-bromo-2-methylpropene (2.5 mL, 25 mmol) in acetone (80 mL) is stirred at 50° C. for 3 days. The mixture is filtered, the filtercake washed with few acetone and the filtrate evaporated to give 2.48 g of 3-(2-methyl-allyl)-pentane-2,4-dione as a dark oil that is used without further purification in subsequent steps; LC-MS: $t_R$=0.87 min, [M+1]$^+$=155.26.

b) A solution of 3-(2-methyl-allyl)-pentane-2,4-dione (2.48 g, 16 mmol) in DCM (10 mL) is cooled at −78° C. and DIPEA (17 mL, 98 mmol) is slowly added. The mixture is stirred for 0.5 h at −78° C., then a solution of trifluoromethanesulfonic anhydride (3.18 mL, 19.3 mmol) in DCM (15 mL) is slowly added keeping the temperature at below −65° C. The red-brown solution is stirred for 0.5 h at −78° C. and then quenched with ice (50 g) and diethyl ether (200 mL). The phases are separated, the organic phase washed with 1M aq. $KHSO_4$ solution and brine, dried with $Na_2SO_4$, filtered and evaporated. The residue is purified by reversed phase MPLC ($H_2O$-MeOH gradient) to give 1.16 g of trifluoromethanesulfonic acid 2-acetyl-1,4-dimethyl-penta-1,4-dienyl ester; LC-MS: $t_R$=1.03 min, [M+1]$^+$=287.01.

c) Sodium hydride (60% in petrolether, 404 mg, 10 mmol) is washed with dry pentane (3×10 mL), then dry THF (30 mL) is added and the suspension is cooled at 0° C. A solution of mercaptoacetic acid ethyl ester (0.445 mL, 4 mmol) in THF (4 mL) is slowly added. After stirring for 0.5 h at 0° C. a solution of trifluoromethanesulfonic acid 2-acetyl-1,4-dimethyl-penta-1,4-dienyl ester (1.16 g, 4 mmol) in THF (4 mL) is slowly added. The mixture is stirred at 0° C. for 0.5 h, then slowly warmed to rt during 15 h. The reaction mixture is partioned between $H_2O$ (75 mL) and DCM (100 mL), the aq. phase is basified with 1M aq. NaOH (50 mL) and extracted with DCM (50 mL). The combined organic extracts are dried ($Na_2SO_4$), filtered and evaporated. The crude product is purified by reversed phase MPLC ($H_2O$-MeOH gradient) to give 450 mg of 3,5-dimethyl-4-(2-methyl-allyl)-thiophene-2-carboxylic acid ethyl ester; LC-MS: $t_R$=1.10 min, [M+1]$^+$= 239.05.

d) To a solution of 3,5-dimethyl-4-(2-methyl-allyl)-thiophene-2-carboxylic acid ethyl ester (978 mg, 4.1 mmol) in ethanol (20 mL) is added 3M aq. LiOH (10 mL) and the mixture is stirred at 60° C. for 1 h. The mixture is partitioned between DCM (100 mL) and 1M aq. HCl (75 mL). The aq. phase is re-extracted with DCM (2×50 mL). The combined organic extracts are dried ($MgSO_4$), filtered and evaporated to give 653 mg of 3,5-dimethyl-4-(2-methyl-allyl)-thiophene-2-carboxylic acid as a light yellow powder; LC-MS: $t_R$=0.94 min, [M+1+$CH_3CN$]$^+$=252.04; $^1$H NMR ($CDCl_3$): δ 11.50 (br. s, 1H), 4.75 (s, 1H), 4.39 (s, 1H), 3.17 (s, 2H), 2.42 (s, 3H), 2.37 (s, 3H), 1.75 (s, 3H).

e) To a solution of 3,5-dimethyl-4-(2-methyl-allyl)-thiophene-2-carboxylic acid (475 mg, 2.26 mmol) in diethyl ether (15 mL), a solution of methyllithium (3.0 mL, 1.6 M in diethyl ether) is added at rt. The mixture is stirred at rt for 1 h before another portion of methyllithium (0.45 mL) is added. Stirring is continued for 1 h. The reaction is quenched by the addition of 1 N aq. $NaH_2PO_4$ solution. The mixture is diluted with diethyl ether, washed with 1 N aq. NaOH, dried over $Na_2SO_4$ and evaporated to give 1-[3,5-dimethyl-4-(2-methyl-allyl)thiophen-2-yl]-ethanone (395 mg) as a yellow oil; LC-MS: $t_R$=1.03 min, [M+1]=209.14.

f) A solution of 1-[3,5-dimethyl-4-(2-methyl-allyl)-thiophen-2-yl]-ethanone (395 mg, 1.9 mmol) and 4-hydroxy-3,5-dimethyl-benzaldehyde (427 mg, 2.84 mmol) in ethanol (10 mL) and 5 N HCl in isopropanol (5 mL) is stirred at rt for 2 h. The dark solution is diluted with diethyl ether (100 mL) and washed with a mixture of sat. aq. $NaHCO_3$ and 1M aq. NaOH (1:1, 3×35 mL). The organic phase is dried ($Na_2SO_4$), filtered and evaporated. The residue is purified by reversed phase MPLC ($H_2O$-MeOH) to give 1-[3,5-dimethyl-4-(2-methyl-allyl)-thiophen-2-yl]-3-(4-hydroxy-3,5-dimethyl-phenyl)-propenone (661 mg) as a yellow solid; LC-MS: $t_R$=1.13 min, [M+1]=341.15.

g) A solution of 1-[3,5-dimethyl-4-(2-methyl-allyl)-thiophen-2-yl]-3-(4-hydroxy-3,5-dimethyl-phenyl)-propenone (38.5 mg, 0.11 mmol) in methanol (5 mL) is treated with Pd/C (10 mg, 10% Pd) and the resulting slurry is stirred at rt for 2 h under 1 bar of H₂. The catalyst is filtered off and the filtrate purified by TLC (SiO₂, EA-heptane) to give 3-(4-hydroxy-3,5-dimethyl-phenyl)-1-(4-isobutyl-3,5-dimethyl-thiophen-2-yl)-propan-1-one (18 mg) as a yellow oil; LC-MS: $t_R$=1.14 min, [M+1]+=345.12; ¹H NMR (CDCl₃): δ 6.78 (s, 2H), 2.97 (t, J=7.4 Hz, 2H), 2.82 (t, J=7.4 Hz, 2H), 2.39 (s, 3H), 2.32-2.28 (m, 5H), 2.15 (s, 6H), 0.84 (d, J=6.4 Hz, 6H).

Example 10

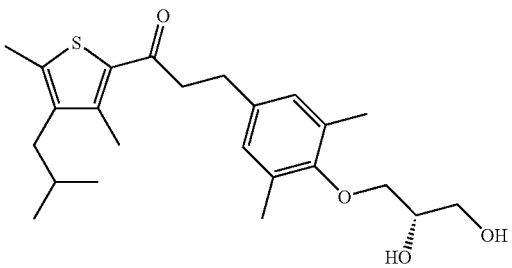

3-[4-((S)-2,3-Dihydroxy-propoxy)-3,5-dimethyl-phenyl]-1-(4-isobutyl-3,5-dimethyl-thiophen-2-yl)-propan-1-one is prepared from 3-(4-hydroxy-3,5-dimethyl-phenyl)-1-(4-isobutyl-3,5-dimethyl-thiophen-2-yl)-propan-1-one in analogy to Example 8; LC-MS: $t_R$=1.06 min, [M+1]=419.22.

Example 11

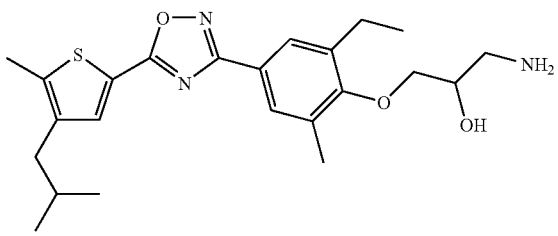

rac-1-Amino-3-{2-ethyl-4-[5-(4-isobutyl-5-methyl-thiophen-2-yl)-[1,2,4]oxadiazol-3-yl]-6-methyl-phenoxy}-propan-2-ol is prepared from 4-isobutyl-5-methyl-thiophene-2-carboxylic acid and 3-ethyl-4-hydroxy-5-methyl benzaldehyde in analogy to Example 22; LC-MS: $t_R$=0.91 min, [M+1]=430.30.

Example 12

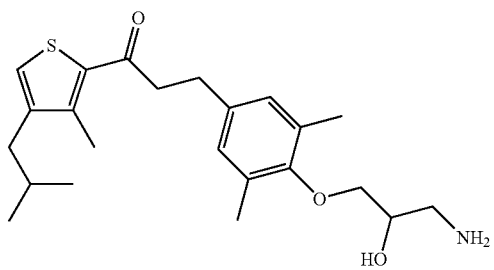

To a solution of 3-(4-hydroxy-3,5-dimethyl-phenyl)-1-(4-isobutyl-3-methyl-thiophen-2-yl)-propan-1-one (317 mg, 0.96 mmol) in isopropanol (10 mL), 3 N aq. NaOH (2.5 mL) followed by epichlorohydrine (284 mg, 3.07 mmol) is added. The dark red mixture is stirred at rt for 16 h before it is diluted with sat. aq. NaHCO₃ and extracted twice with diethyl ether. The organic extracts are washed with water, dried over Na₂SO₄, filtered and evaporated to give crude 3-(3,5-dimethyl-4-oxiranylmethoxy-phenyl)-1-(4-isobutyl-3-methyl-thiophen-2-yl)-propan-1-one (339 mg) as a yellow oil. The material is dissolved in 7 N NH₃ in methanol (7.5 mL) and the resulting solution is stirred in an autoklave at 65° C. for 2.5 h. The solvent is removed in vacuo and the residue is dried under HV to leave rac-3-[4-(3-amino-2-hydroxy-propoxy)-3,5-dimethyl-phenyl]-1-(4-isobutyl-3-methyl-thiophen-2-yl)-propan-1-one (353 mg) as an orange oil; LC-MS: $t_R$=0.88 min, [M+1]=404.20; ¹H NMR (CDCl₃): δ 7.06 (s, 1H), 6.88 (s, 2H), 3.98-3.90 (m 1H), 3.85-3.73 (m, 2H), 3.15-3.07 (m, 2H), 3.00-2.84 (m, 4H), 2.47 (s, 3H), 2.42 (d, J=7.6 Hz, 2H), 2.25 (s, 6H), 1.83 (hept, J=7.0 Hz, 1H), 0.92 (d, J=6.4 Hz, 6H).

Example 13

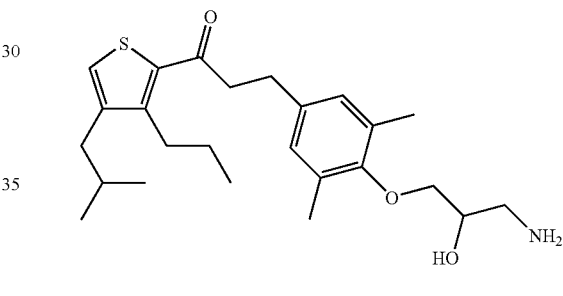

rac-3-[4-(3-Amino-2-hydroxy-propoxy)-3,5-dimethyl-phenyl]-1-(4-isobutyl-3-propyl-thiophen-2-yl)-propan-1-one is prepared from 3-(4-hydroxy-3,5-dimethyl-phenyl)-1-(4-isobutyl-3-propyl-thiophen-2-yl)-propan-1-one in analogy to Example 12; LC-MS: $t_R$=0.92 min, [M+1]= 432.39.

Example 14

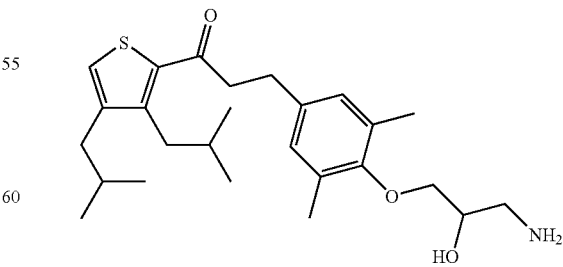

rac-3-[4-(3-Amino-2-hydroxy-propoxy)-3,5-dimethyl-phenyl]-1-(3,4-diisobutyl-thiophen-2-yl)-propan-1-one is prepared from 1-(3,4-diisobutyl-thiophen-2-yl)-3-(4-hydroxy-3,5-dimethyl-phenyl)-propan-1-one in analogy to Example 12; LC-MS: $t_R$=0.93 min, [M+1]=446.34.

Example 15

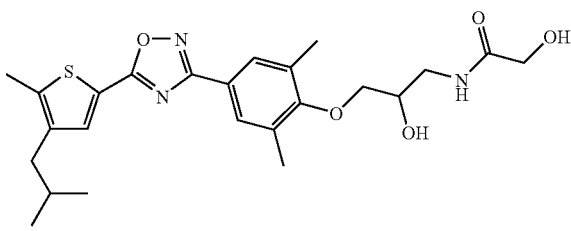

rac-2-Hydroxy-N-(2-hydroxy-3-{4-[5-(4-isobutyl-5-methyl-thiophen-2-yl)-[1,2,4]oxadiazol-3-yl]-2,6-dimethyl-phenoxy}-propyl)-acetamide is prepared from rac-1-amino-3-{4-[5-(4-isobutyl-5-methyl-thiophen-2-yl)-[1,2,4] oxadiazol-3-yl]-2,6-dimethyl-phenoxy}-propan-2-ol in analogy to Example 17; LC-MS: $t_R$=1.02 min, [M+1]= 474.31.

Example 16

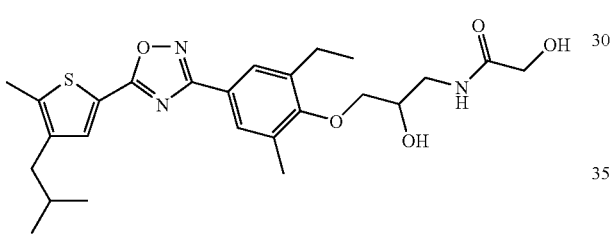

rac-N-(3-{2-Ethyl-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide is prepared from rac-1-amino-3-{2-ethyl-4-[5-(4-isobutyl-5-methyl-thiophen-2-yl)-[1,2,4] oxadiazol-3-yl]-6-methyl-phenoxy}-propan-2-ol in analogy to Example 17; LC-MS: $t_R$=1.04 min, [M+1]=488.30.

Example 17

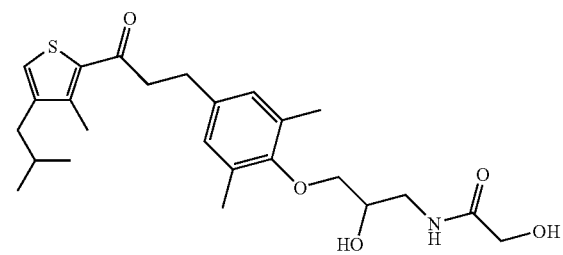

To a solution of rac-3-[4-(3-amino-2-hydroxy-propoxy)-3,5-dimethyl-phenyl]-1-(4-isobutyl-3-methyl-thiophen-2-yl)-propan-1-one (353 mg, 0.876 mmol) in DCM (10 mL), glycolic acid (127 mg, 1.67 mmol) followed by DIPEA (521 mg, 4.03 mmol) and TBTU (439 mg, 1.37 mmol) is added and the reaction mixture is stirred at rt for 16 h. The mixture is diluted with DCM and washed twice with water. The aq. washings are extracted three times with DCM. The combined organic extracts are dried over $MgSO_4$, filtered and evaporated. The crude product is purified by CC on silica gel eluting with EA containing 0 to 100% of MeOH to give racemic 2-hydroxy-N-(2-hydroxy-3-{4-[3-(4-isobutyl-3-methyl-thiophen-2-yl)-3-oxo-propyl]-2,6-dimethyl-phenoxy}-propyl)-acetamide (160 mg) as a beige solid; LC-MS: $t_R$=0.99 min, [M+1]= 462.40; $^1$H NMR ($D_6$-DMSO): δ 7.66 (t, J=5.9 Hz, 1H), 7.45 8s, 1H), 6.86 (s, 2H), 5.63 (s br, 1H), 5.26 (s br, 1H), 3.91-3.83 (m, 1H), 3.79 (s, 2H), 3.63-3.55 (m, 2H), 3.45-3.36 (m, 1H), 3.22-3.12 (m 1H), 0.310-3.04 (m, 2H), 2.80-2.73 (m, 2H), 2.40-2.37 (m, 5H), 2.15 (s, 6H), 1.76 (m, J=7.0 Hz, 1H), 0.85 (d, J=6.4 Hz, 6H).

Example 18

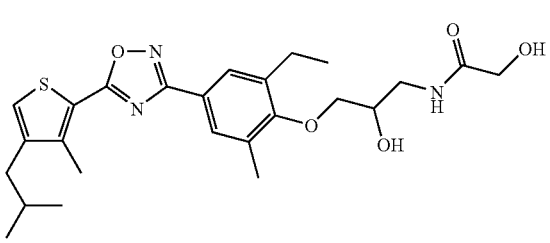

rac-N-(3-{2-Ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide is prepared from rac-3-[4-(3-amino-2-hydroxy-propoxy)-3-ethyl-5-methyl-phenyl]-1-(4-isobutyl-3-methyl-thiophen-2-yl)-propan-1-one in analogy to Example 17; LC-MS: $t_R$=1.04 min, [M+1]=488.29.

Example 19

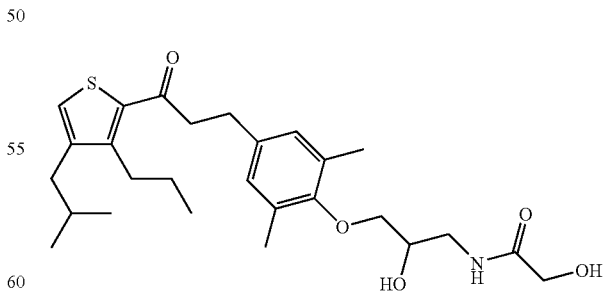

rac-2-Hydroxy-N-(2-hydroxy-3-{4-[3-(4-isobutyl-3-propyl-thiophen-2-yl)-3-oxo-propyl]-2,6-dimethyl-phenoxy}-propyl)-acetamide is prepared from rac-3-[4-(3-amino-2-hydroxy-propoxy)-3,5-dimethyl-phenyl]-1-(4-isobutyl-3- propyl-thiophen-2-yl)-propan-1-one in analogy to Example 17; LC-MS: $t_R$=1.05 min, [M+1]=490.40.

Example 20

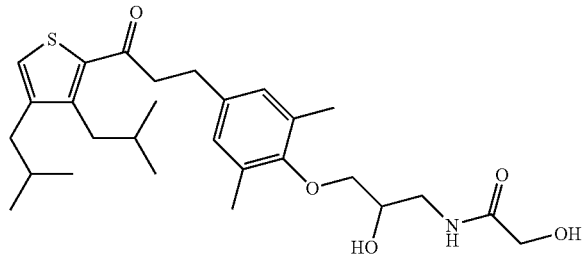

rac-N-(3-{4-[3-(3,4-Diisobutyl-thiophen-2-yl)-3-oxo-propyl]-2,6-dimethyl-phenoxy}-2-hydroxy-propyl)-2-hydroxy-acetamide is prepared from rac-3-[4-(3-amino-2-hydroxy-propoxy)-3,5-dimethyl-phenyl]-1-(3,4-diisobutyl-thiophen-2-yl)-propan-1-one in analogy to Example 17; LC-MS: $t_R$=1.07 min, [M+1]=504.35.

Example 21

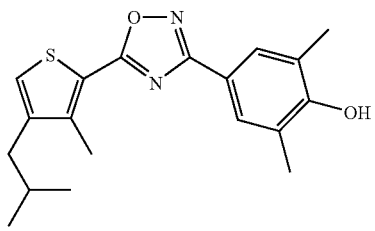

a) A solution of 4-isobutyl-3-methyl-thiophene-2-carboxylic acid (1.78 g, 9.0 mmol), DIPEA (3.78 g, 29.2 mmol) and TBTU (3.21 g, 10.0 mmol) in DMF (20 mL) is stirred at rt for 15 min before 4,N-dihydroxy-3,5-dimethyl-benzamidine (1.80 g, 10.0 mmol) is added. The mixture is stirred for 15 h at rt. The solvent is evaporated and the residue taken up in EA (100 mL) and sat. aq. Na$_2$CO$_3$ (100 mL). The phases are separated and the aq. phase is extracted with additional EA (2×75 mL). The combined organic extracts are washed with sat. aq. Na$_2$CO$_3$ (50 mL) and brine (50 mL), dried (Na$_2$SO$_4$), filtered and evaporated. The brown residue is suspended in CHCl$_3$ (50 mL) and filtered. The solid is washed with CHCl$_3$ (25 mL) and dried to give 4-isobutyl-3-methyl-thiophene-2-carboxylic acid (4,N-dihydroxy-3,5-dimethyl-benzamidine) ester (2.34 g) as a beige powder; LC-MS: $t_R$=1.02 min, [M+1]=361.49; $^1$H NMR (D$_6$-DMSO): δ 8.66 (s br, 1H), 7.45 (s, 1H), 7.33 (s, 2H), 6.43 (s br, 2H), 2.42-2.39 (m, 5H), 2.18 (s, 6H), 1.80 (hept, J=7.0 Hz, 1H), 0.88 (d, J=7.0 Hz, 6H).

b) 4-Isobutyl-3-methyl-thiophene-2-carboxylic acid (4,N-dihydroxy-3,5-dimethyl-benzamidine) ester (1.85 g, 5.13 mmol) is suspended in dry toluene and the mixture is heated at reflux in a Dean-Stark apparatus for 15 h. The mixture is filtered and the filtrate is evaporated. The residue is purified by CC on silica gel eluting with a gradient of EA in heptane to give 4-[5-(4-isobutyl-3-methyl-thiophen-2-yl)-[1,2,4]oxadiazol-3-yl]-2,6-dimethyl-phenol (668 mg) as a light yellow powder; LC-MS: $t_R$=1.16 min, [M+1]=343.19; $^1$H NMR (CDCl$_3$): δ 7.79 (s, 2H), 7.17 8s, 1H), 5.27 (s, 1H), 2.61 (s, 3H), 2.47 (d, J=7.0 Hz, 2H), 2.31 (s, 6H), 1.88 (hept, J=7.0 Hz, 1H), 0.95 (d, J=7.0 Hz, 6H).

Example 22

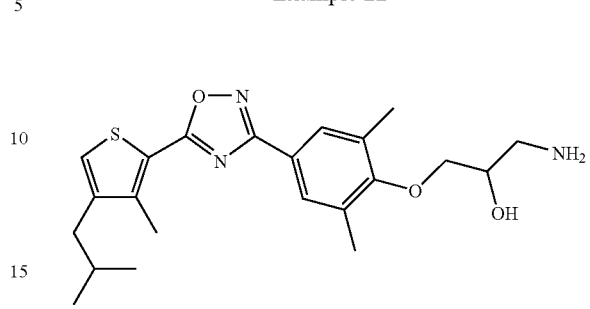

a) To a solution of 4-[5-(4-isobutyl-3-methyl-thiophen-2-yl)-[1,2,4]oxadiazol-3-yl]-2,6-dimethyl-phenol (515 mg, 1.50 mmol) in isopropanol (20 mL), 3 N aq. NaOH (5 mL) followed by epichlorohydrine (473 mg, 5.12 mmol) is added and the mixture is stirred at rt for 15 h. Another portion of epichlorohydrine (473 mg, 5.12 mmol) is added and stirring is continued for 24 h. The mixture is diluted with sat. aq. Na$_2$CO$_3$ and is then extracted with DCM (4×75 mL). The combined organic extracts are dried (Na$_2$SO$_4$), filtered and evaporated. The residue is purified by CC on silica gel eluting with heptane:EA 4:1 to give rac-3-(3,5-dimethyl-4-oxiranyl-methoxy-phenyl)-5-(4-isobutyl-3-methyl-thiophen-2-yl)-[1,2,4]oxadiazole (382 mg) as a white powder; LC-MS: $t_R$=1.22 min, [M+1]=399.28.

b) A suspension of rac-3-(3,5-dimethyl-4-oxiranyl-methoxy-phenyl)-5-(4-isobutyl-3-methyl-thiophen-2-yl)-[1,2,4]oxadiazole (382 mg, 0.959 mmol) in 7 N NH$_3$ in MeOH (10 mL) and THF (5 mL) is stirred at 60° C. for 15 h. The mixture is diluted with 1M aq. NaOH (30 mL) and extracted with DCM (4×75 mL). The combined organic extracts are dried (Na$_2$SO$_4$), filtered and evaporated to give rac-1-amino-3-{4-[5-(4-isobutyl-3-methyl-thiophen-2-yl)-[1,2,4]oxadiazol-3-yl]-2,6-dimethyl-phenoxy}-propan-2-ol (419 mg) as a pale yellow solid; LC-MS: $t_R$=0.90 min, [M+1]=416.42.

Example 23

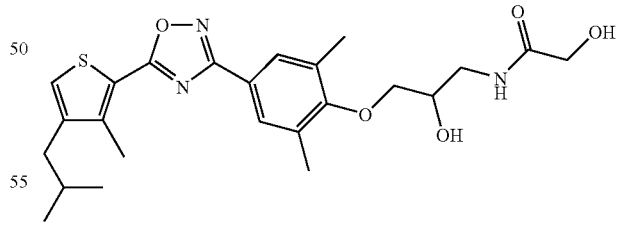

rac-2-Hydroxy-N-(2-hydroxy-3-{4-[5-(4-isobutyl-3-methyl-thiophen-2-yl)-[1,2,4]oxadiazol-3-yl]-2,6-dimethyl-phenoxy}-propyl)acetamide is prepared from rac-1-amino-3-{4-[5-(4-isobutyl-3-methyl-thiophen-2-yl)-[1,2,4]oxadiazol-3-yl]-2,6-dimethyl-phenoxy}-propan-2-ol in analogy to Example 17; LC-MS: $t_R$=1.04 min, [M+1]=474.19; $^1$H NMR (D$_6$-DMSO): δ 7.71 (s, 2H), 7.68 (t br, J=6 Hz, 1H), 7.62 (s, 2H), 5.54 (t, J=5 Hz, 1H), 5.28 (d, J=5.3 Hz, 1H), 3.96-3.88 (m, 1H), 3.81 (d, J=5 Hz, 2H), 3.79-3.66 (m, 2H), 3.46-3.36 (m, 1H), 3.28-3.17 (m, 1H), 2.58 (s, 3H), 2.31 (s, 6H), 1.85 (hept, J=7.0 Hz, 1H), 0.90 (d, J=6.4 Hz, 6H).

Example 24

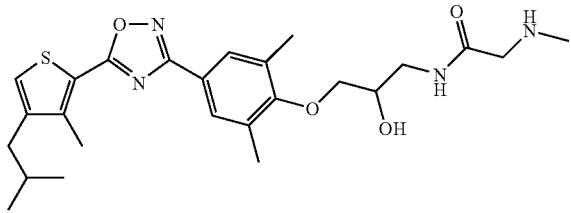

A solution of rac-1-amino-3-{4-[5-(4-isobutyl-3-methyl-thiophen-2-yl)-[1,2,4]oxadiazol-3-yl]-2,6-dimethyl-phenoxy}-propan-2-ol (100 mg, 0.241 mmol) in DCM (1 mL) is added to a stirred solution of Boc-sarcosine (60 mg, 0.317 mmol), DIPEA (38 mg, 0.292 mmol) and TBTU (85 mg, 0.265 mmol) in DCM (5 mL). The mixture is stirred at rt for 1 h, diluted with DCM (50 mL) and washed with sat. aq. $Na_2CO_3$ (2×20 mL). The organic extract is dried ($Na_2SO_4$), filtered and evaporated. The residue dissolved in 4M HCl in dioxane (10 mL) and stirred for 1 h. The mixture is diluted with DCM (75 mL) and washed with 1 N aq. NaOH (50 mL). The aq. phase is extracted with DCM (3×30 mL). The combined organic extracts are dried ($Na_2SO_4$), filtered and evaporated. The residue is purified on prep. TLC plates with DCM containing 10% of 7 N $NH_3$ in MeOH to give rac-N-(2-hydroxy-3-{4-[5-(4-isobutyl-3-methyl-thiophen-2-yl)-[1,2,4]oxadiazol-3-yl]-2,6-dimethyl-phenoxy}-propyl)-2-methylamino-acetamide (89 mg) as a white powder; LC-MS: $t_R$=0.89 min, [M+1]=487.26; $^1$H NMR ($D_6$-DMSO): δ 7.85 (t, J=6 Hz, 1H), 7.70 (s, 2H), 7.65 (s, 1H), 5.27 (d br, J=5 Hz, 1H), 3.93-3.85 (m, 1H), 3.76-3.65 (m, 2H), 3.43-3.35 (m, 1H), 3.24-3.14 (m, 1H), 3.02 (s, 2H), 2.54 (s, 3H), 2.45 (d, J=6.4 Hz, 2H), 2.30 (s, 6H), 2.20 (s, 3H), 1.83 (hept, J=7.0 Hz, 1H), 0.88 (d, J=7.0 Hz, 6H).

Example 25

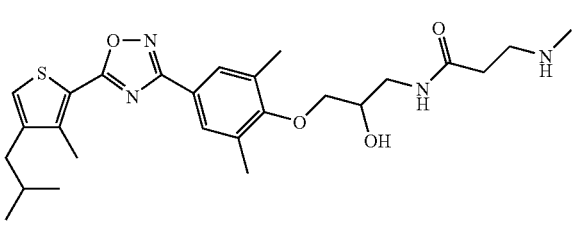

rac-N-(2-Hydroxy-3-{4-[5-(4-isobutyl-3-methyl-thiophen-2-yl)-[1,2,4]oxadiazol-3-yl]-2,6-dimethyl-phenoxy}-propyl)-3-methylamino-propionamide is prepared from rac-1-amino-3-{4-[5-(4-isobutyl-3-methyl-thiophen-2-yl)-[1,2,4]oxadiazol-3-yl]-2,6-dimethyl-phenoxy}-propan-2-ol in analogy to Example 24; LC-MS: $t_R$=0.90 min, [M+1]=501.36.

Example 26

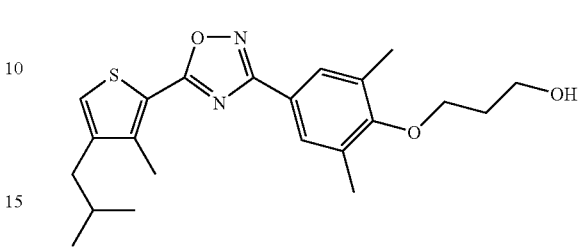

3-{4-[5-(4-Isobutyl-3-methyl-thiophen-2-yl)-[1,2,4]oxadiazol-3-yl]-2,6-dimethyl-phenoxy}-propan-1-ol is prepared by alkylating 3-(4-hydroxy-3,5-dimethyl-phenyl)-1-(4-isobutyl-3-methyl-thiophen-2-yl)-propan-1-one with 3-bromo-propan-1-ol following the alkylation procedure in Example 12; LC-MS: $t_R$=1.17 min, [M+1]=401.26.

Example 27

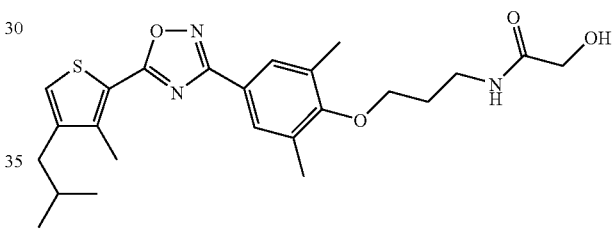

2-Hydroxy-N-(3-{4-[5-(4-isobutyl-3-methyl-thiophen-2-yl)-[1,2,4]oxadiazol-3-yl]-2,6-dimethyl-phenoxy}-propyl)-acetamide is prepared from 3-{4-[5-(4-isobutyl-3-methyl-thiophen-2-yl)-[1,2,4]oxadiazol-3-yl]-2,6-dimethyl-phenoxy}-propan-1-ol following the procedure given in Example 35; LC-MS: $t_R$=1.14 min, [M+1]=458.26.

Example 28

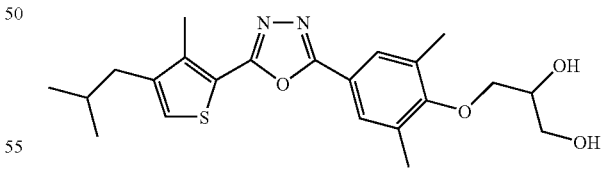

a) 4-Allyloxy-3,5-dimethyl-benzoic acid (Moffett, R. B.; Seay, P. H.; *J. Med. Pharm. Chem.* (1960) 2201-2212) (620 mg, 3 mmol), tert.-butylcarbazate (475 mg, 3.6 mmol) and $NEt_3$ 0.5 mL) are dissolved in DMF (10 mL) and TBTU (1.15 g, 3.6 mmol) is added at 0° C. The mixture is stirred for 2 h at 0° C. to rt, quenched into ether (200 mL) and washed with 1M aq. HCl (2×50 mL), 1M aq. NaOH (2×50 mL) and brine (50 mL). The organic phase is dried ($MgSO_4$), filtered and evaporated. The residue is dissolved in dioxane (10 mL) and 4M HCl in dioxane (4 mL) is added. The mixture is stirred at rt for 15 h; the mixture is diluted with dry diethyl ether (10 mL), the precipitate filtered, washed with dry diethyl ether (10 mL) and dried in vacuo to give 487 mg of 4-allyloxy-3,5-dimethyl-benzoic acid hydrazide hydrochloride as a white powder; LC-MS: $t_R$=0.69 min, [M+1]$^+$=221.21.

b) A solution of 4-isobutyl-3-methyl-thiophene-2-carboxylic acid (100 mg, 0.5 mmol), 4-allyloxy-3,5-dimethyl-benzoic acid hydrazide hydrochloride (192 mg, 0.75 mmol) and NEt$_3$ (0.28 mL) in DMF (10 mL) is cooled at 0° C. and TBTU (200 mg, 0.6 mmol) is added. The mixture is stirred for 15 h while warming from 0° C. to rt. The mixture is diluted with diethyl ether (50 mL) and washed with 1M aq. NaOH (2×20 mL), 1M aq. HCl (2×20 mL) and brine (10 mL). The organic phase is dried (Na$_2$SO$_4$), filtered and evaporated to give 160 mg of 4-allyloxy-3,5-dimethyl-benzoic acid N'-(4-isobutyl-3-methyl-thiophene-2-carbonyl)-hydrazide; LC-MS: $t_R$=1.05 min, [M+1]$^+$=400.83.

c) A solution of 4-allyloxy-3,5-dimethyl-benzoic acid N'-(4-isobutyl-3-methyl-thiophene-2-carbonyl)-hydrazide (160 mg, 0.4 mmol) and (methoxycarbonyl-sulfamoyl)triethylammonium hydroxide (350 mg, 1.27 mmol) in dry THF (5 mL) is heated at 110° C. in a microwave oven for 6 min. The mixture is poured into diethyl ether (10 mL) and washed with 1M aq. HCl (10 mL). The aq. phase is re-extracted with ether (10 mL). The combined organic extracts are dried (Na$_2$SO$_4$), filtered and evaporated to give 181 mg of crude 2-(4-allyloxy-3,5-dimethyl-phenyl)-5-(4-isobutyl-3-methyl-thiophen-2-yl)-[1,3,4]oxadiazole; LC-MS: $t_R$=1.23 min, [M+1]$^+$=383.35.

d) To a solution of 2-(4-allyloxy-3,5-dimethyl-phenyl)-5-(4-isobutyl-3-methyl-thiophen-2-yl)-[1,3,4]oxadiazole (181 mg crude, 0.4 mmol) in a mixture of acetone and water (15:1.5 mL) are added N-methylmorpholine-N-oxide (250 mg, 1.85 mmol) and, subsequently, 2.5% OsO$_4$ in tert.-butanol (0.1 mL). The mixture is stirred at rt for 36 h. The mixture is quenched into diethyl ether (75 mL) and washed with 1M aq. NaOH (50 mL), 1M aq. HCl (30 mL) and brine (20 mL). The organic phase is dried (Na$_2$SO$_4$), filtered and evaporated. The residue is purified by TLC (SiO$_2$, EA-heptane) to give 118 mg of 3-{4-[5-(4-isobutyl-3-methyl-thiophen-2-yl)-[1,3,4]oxadiazol-2-yl]-2,6-dimethyl-phenoxy}-propane-1,2-diol as a white powder; LC-MS: $t_R$=1.00 min, [M+1]$^+$=417.28; $^1$H NMR (D$_6$-DMSO): δ, 7.70 (s, 2 H) 7.51 (s, 1 H), 4.96 (d, J=5.0 Hz, 1 H), 4.63 (t, J=5.6 Hz, 1 H), 3.68-3.89 (m, 3 H), 3.47 (t, J=5.6 Hz, 2 H), 2.51 (s, 3 H), 2.45 (m, 2 H), 2.33 (s, 6 H), 1.85 (m, 1 H), 0.90 (d, J=6.7 Hz, 6 H).

Example 29

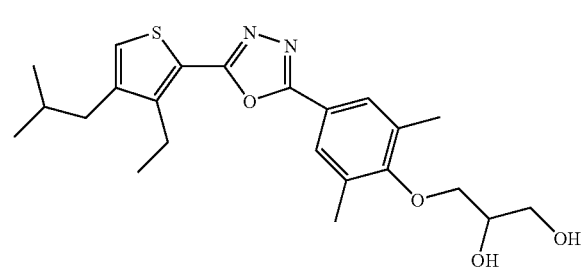

3-{4-[5-(3-Ethyl-4-isobutyl-thiophen-2-yl)-[1,3,4]oxadiazol-2-yl]-2,6-dimethyl-phenoxy}-propane-1,2-diol is prepared from 3-ethyl-4-isobutyl-thiophene-2-carboxylic acid in analogy to Example 28; LC-MS: $t_R$=1.04 min, [M+1]=431.28.

Example 30

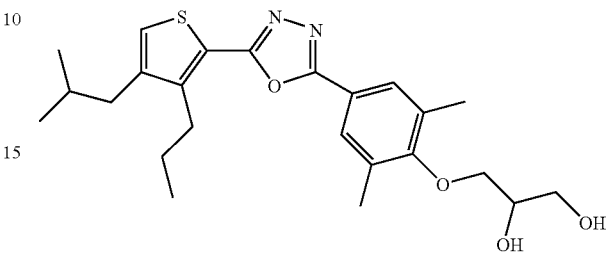

3-{4-[5-(4-Isobutyl-3-propyl-thiophen-2-yl)-[1,3,4]oxadiazol-2-yl]-2,6-dimethyl-phenoxy}-propane-1,2-diol is prepared from 4-isobutyl-3-propyl-thiophene-2-carboxylic acid in analogy to Example 28; LC-MS: $t_R$=1.08 min, [M+1]=445.26.

Example 31

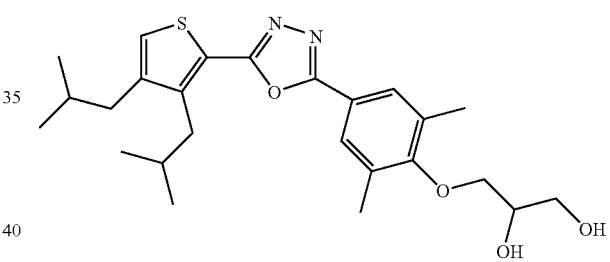

3-{4-[5-(3,4-Diisobutyl-thiophen-2-yl)-[1,3,4]oxadiazol-2-yl]-2,6-dimethyl-phenoxy}-propane-1,2-diol is prepared from 3,4-diisobutyl-thiophene-2-carboxylic acid in analogy to Example 28; LC-MS: $t_R$=1.09 min, [M+1]=459.23.

Example 32

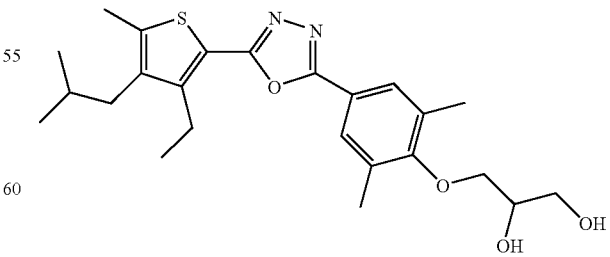

3-{4-[5-(3-Ethyl-4-isobutyl-5-methyl-thiophen-2-yl)-[1,3,4]oxadiazol-2-yl]-2,6-dimethyl-phenoxy}-propane-1,2-diol is prepared from 3-ethyl-4-isobutyl-5-methylthiophene-2-carboxylic acid in analogy to Example 28; LC-MS: $t_R$=1.07 min, [M+1]=445.38.

Example 33

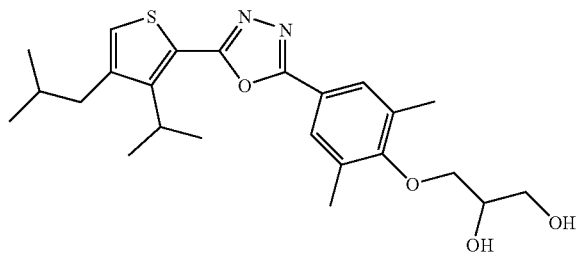

3-{4-[5-(4-Isobutyl-3-isopropyl-thiophen-2-yl)-[1,3,4]oxadiazol-2-yl]-2,6-dimethyl-phenoxy}-propane-1,2-diol is prepared from 4-isobutyl-3-isopropyl-thiophene-2-carboxylic acid in analogy to Example 28; LC-MS: $t_R$=1.06 min, [M+1]=445.26.

Example 34

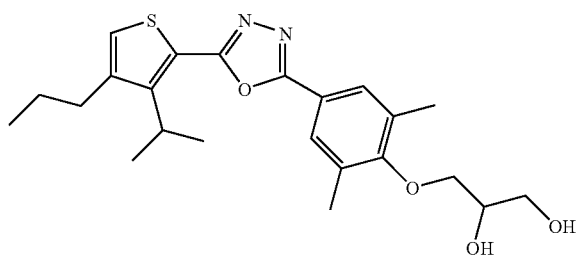

3-{4-[5-(3-Isopropyl-4-propyl-thiophen-2-yl)-[1,3,4]oxadiazol-2-yl]-2,6-dimethyl-phenoxy}-propane-1,2-diol is prepared from 3-isopropyl-4-propyl-thiophene-2-carboxylic acid in analogy to Example 28; LC-MS: $t_R$=1.03 min, [M+1]=431.3.

Example 35

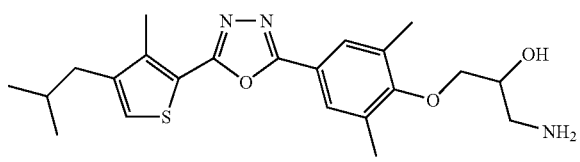

To a solution of 3-{4-[5-(4-isobutyl-3-methyl-thiophen-2-yl)-[1,3,4]oxadiazol-2-yl]-2,6-dimethyl-phenoxy}-propane-1,2-diol (90 mg, 0.22 mmol) in THF (4 mL) are added NEt$_3$ (0.14 mL) and, subsequently, methanesulfonylchloride (0.02 mL, 0.26 mmol). The mixture is stirred at rt for 3 h. A solution of NH$_3$ in MeOH (7M, 4 mL) is added and the mixture is heated at 60° C. for 15 h. The mixture is evaporated, 1M aq. NaOH (3 mL) is added and the mixture is extracted with EA (2×20 mL). The organic extracts are dried (Na$_2$SO$_4$), filtered and evaporated to give crude 1-amino-3-{4-[5-(4-isobutyl-3-methyl-thiophen-2-yl)-[1,3,4]oxadiazol-2-yl]-2,6-dimethylphenoxy}-propan-2-ol; LC-MS: $t_R$=0.86 min, [M+1]$^+$=416.32.

Example 36

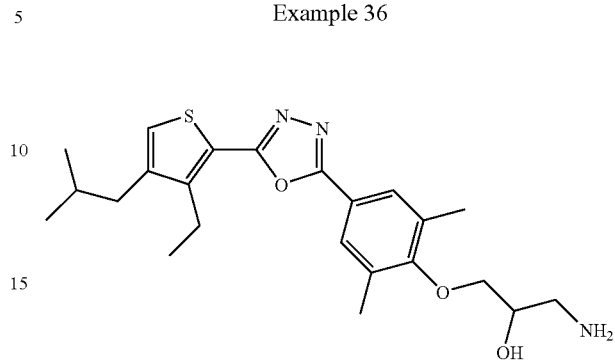

1-Amino-3-{4-[5-(3-ethyl-4-isobutyl-thiophen-2-yl)-[1,3,4]oxadiazol-2-yl]-2,6-dimethyl-phenoxy}-propan-2-ol is prepared from 3-{4-[5-(3-ethyl-4-isobutyl-thiophen-2-yl)-[1,3,4]oxadiazol-2-yl]-2,6-dimethyl-phenoxy}-propane-1,2-diol in analogy to Example 35; LC-MS: $t_R$=0.87 min, [M+1]=430.31.

Example 37

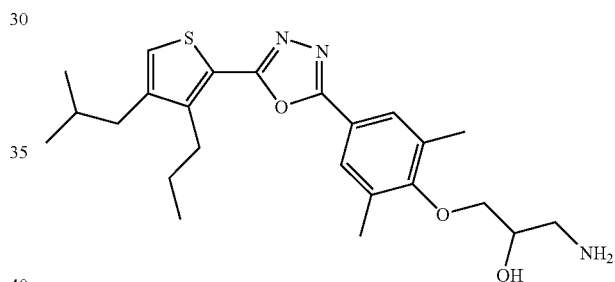

1-Amino-3-{4-[5-(4-isobutyl-3-propyl-thiophen-2-yl)-[1,3,4]oxadiazol-2-yl]-2,6-dimethyl-phenoxy}-propan-2-ol is prepared from 3-{4-[5-(4-isobutyl-3-propyl-thiophen-2-yl)-[1,3,4]oxadiazol-2-yl]-2,6-dimethyl-phenoxy}-propane-1,2-diol in analogy to Example 35; LC-MS: $t_R$=0.90 min, [M+1]=444.26.

Example 38

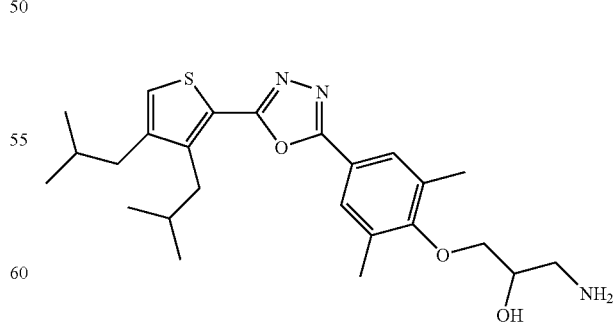

1-Amino-3-{4-[5-(3,4-diisobutyl-thiophen-2-yl)-[1,3,4]oxadiazol-2-yl]-2,6-dimethyl-phenoxy}-propan-2-ol is prepared from 3-{4-[5-(3,4-diisobutyl-thiophen-2-yl)-[1,3,4]oxadiazol-2-yl]-2,6-dimethyl-phenoxy}-propane-1,2-diol in analogy to Example 35; LC-MS: $t_R$=0.91 min, [M+1]=458.25; $^1$H NMR (CD$_3$OD): δ7.71 (s, 2H), 7.36 (s, 1 H), 4.05-4.17 (m, 1 H), 4.01 (s, 2 H), 3.80-3.92 (m, 2 H), 3.63 (dd, J=13.5, 4.4 Hz, 1H), 3.44 (dd, J=13.8, 7.3 Hz, 1 H), 2.94 (d, J=7.3 Hz, 2 H), 2.50 (d, J=7.3 Hz, 2 H), 2.37 (s, 6 H), 1.86-2.05 (m, 2 H), 0.96 (m, 12 H).

Example 39

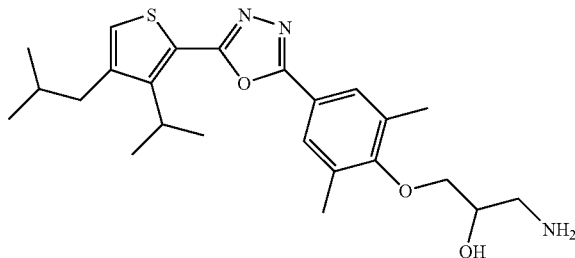

1-Amino-3-{4-[5-(4-isobutyl-3-isopropyl-thiophen-2-yl)-[1,3,4]oxadiazol-2-yl]-2,6-dimethyl-phenoxy}-propan-2-ol is prepared from 3-{4-[5-(4-isobutyl-3-isopropyl-thiophen-2-yl)-[1,3,4]oxadiazol-2-yl]-2,6-dimethyl-phenoxy}-propane-1,2-diol in analogy to Example 35; LC-MS: $t_R$=0.89 min, [M+1]=444.34.

Example 40

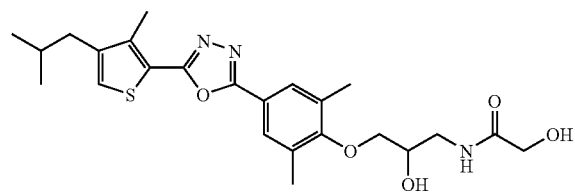

To a solution of crude 1-amino-3-{4-[5-(4-isobutyl-3-methyl-thiophen-2-yl)-[1,3,4]oxadiazol-2-yl]-2,6-dimethyl phenoxy}-propan-2-ol (0.22 mmol) in DMF (1 mL) are added glycolic acid (25 mg), DIPEA (0.1 mL) and finally TBTU (60 mg). The mixture is stirred for 15 h at rt, evaporated and the residue purified by TLC (SiO$_2$, EA) to give 2-hydroxy-N-(2-hydroxy-3-{4-[5-(4-isobutyl-3-methyl-thiophen-2-yl)-[1,3,4]oxadiazol-2-yl]-2,6-dimethyl-phenoxy}-propyl)-acetamide (1.8 mg); LC-MS: $t_R$=0.97 min, [M+1]$^+$=474.26.

Example 41

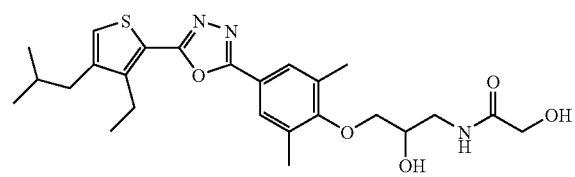

N-(3-{4-[5-(3-Ethyl-4-isobutyl-thiophen-2-yl)-[1,3,4]oxadiazol-2-yl]-2,6-dimethyl-phenoxy}-2-hydroxy-propyl)-2-hydroxy-acetamide is prepared from 1-amino-3-{4-[5-(3-ethyl-4-isobutyl-thiophen-2-yl)-[1,3,4]oxadiazol-2-yl]-2,6-dimethyl-phenoxy}-propan-2-ol in analogy to Example 40; LC-MS: $t_R$=1.00 min, [M+1]=488.28.

Example 42

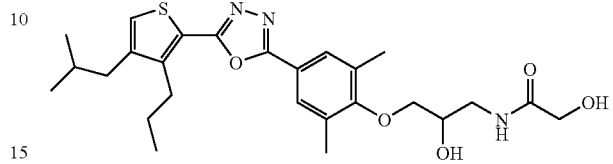

2-Hydroxy-N-(2-hydroxy-3-{4-[5-(4-isobutyl-3-propyl-thiophen-2-yl)-[1,3,4]oxadiazol-2-yl]-2,6-dimethyl-phenoxy}-propyl)-acetamide is prepared from 1-amino-3-{4-[5-(4-isobutyl-3-propyl-thiophen-2-yl)-[1,3,4]oxadiazol-2-yl]-2,6-dimethyl-phenoxy}-propan-2-ol in analogy to Example 40; LC-MS: $t_R$=1.03 min, [M+1]=502.26.

Example 43

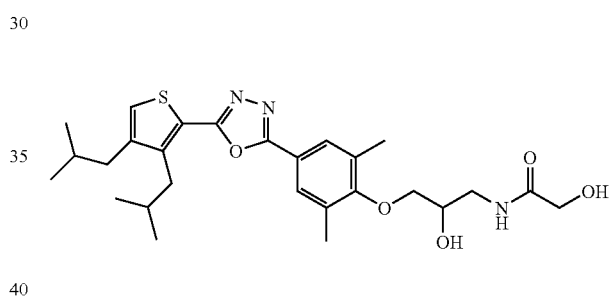

N-(3-{4-[5-(3,4-Diisobutyl-thiophen-2-yl)-[1,3,4]oxadiazol-2-yl]-2,6-dimethyl-phenoxy}-2-hydroxy-propyl)-2-hydroxy-acetamide is prepared from 1-amino-3-{4-[5-(3,4-diisobutyl-thiophen-2-yl)-[1,3,4]oxadiazol-2-yl]-2,6-dimethyl-phenoxy}-propan-2-ol in analogy to Example 40; LC-MS: $t_R$=1.05 min, [M+1]=516.37.

Example 44

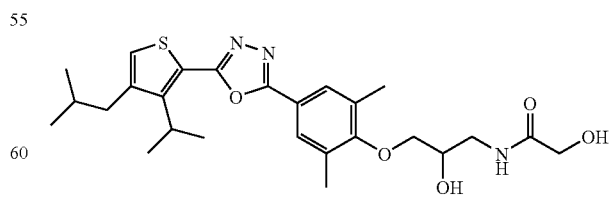

2-Hydroxy-N-(2-hydroxy-3-{4-[5-(4-isobutyl-3-isopropyl-thiophen-2-yl)-[1,3,4]oxadiazol-2-yl]-2,6-dimethyl-phenoxy}-propyl)-acetamide is prepared from 1-amino-3-{4-[5-(4-isobutyl-3-isopropyl-thiophen-2-yl)-[1,3,4]

oxadiazol-2-yl]-2,6-dimethyl-phenoxy}-propan-2-ol in analogy to Example 40; LC-MS: $t_R$=1.02 min, [M+1]=502.3.

Example 45

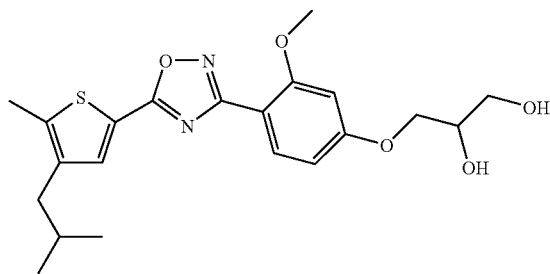

a) To a mixture of 4-isobutyl-5-methyl-thiophene-2-carboxylic acid (505 mg, 2.55 mmol), 4-allyloxy-N-hydroxy-2-methoxy-benzamidine (611 mg, 2.75 mmol) and DIPEA (377 mg, 2.92 mmol) in DMF (10 mL) is added TBTU (882 mg, 2.75 mmol). The mixture is stirred at rt for 15 h before it is diluted with diethyl ether (100 mL) and washed with 1 N aq. NaOH (2×30 mL), 1 M aq. KHSO₄ (30 mL) and brine (30 mL). The organic extract is dried (Na₂SO₄), filtered and evaporated. The yellow oily residue is dissolved in dry toluene (10 mL) and heated at 150° C. for 20 min in a microwave oven. The mixture is poured into diethyl ether (100 mL) and washed with brine (75 mL). The organic extract is dried (Na₂SO₄), filtered and evaporated to give 3-(4-allyloxy-2-methoxy-phenyl)-5-(4-isobutyl-5-methyl-thiophen-2-yl)-[1,2,4]oxadiazole (609 mg) as a yellow solid; LC-MS: $t_R$=1.19 min, [M+1]=385.23.

b) To a solution of 3-(4-allyloxy-2-methoxy-phenyl)-5-(4-isobutyl-5-methyl-thiophen-2-yl)-[1,2,4]oxadiazole (609 mg, 1.59 mmol) in acetone (15 mL) and water (1.5 mL), NMO (750 mg, 5.55 mmol) and OsO₄ (0.1 mL, 2.5% solution in tert.butanol, 8 μmol) is added. The mixture is stirred at rt for 48 h. The mixture is diluted with water (50 mL) and extracted with EA (100 mL, 2×50 mL). The combined organic extracts are dried (Na₂SO₄), filtered and evaporated. The residue is purified by CC on silica gel eluting with EA to give rac-3-{4-[5-(4-isobutyl-5-methyl-thiophen-2-yl)-[1,2,4]oxadiazol-3-yl]-3-methoxy-phenoxy}-pro-pane-1,2-diol (480 mg) as a pale yellow solid; LC-MS: $t_R$=0.99 min, [M+1]=419.19; ¹H NMR (CD₃OD): δ 7.96 (d, J=8.8 Hz, 1H), 7.66 (s, 1H), 6.72-6.60 (m, 2H), 4.20-3.98 (m, 3H), 3.93 (s, 3H), 3.74-3.64 (m, 2H), 2.50-2.40 (m, 5H), 1.90 (hept, J=7.0 Hz, 1H), 0.94 (d, J=6.4 Hz, 6H).

Example 46

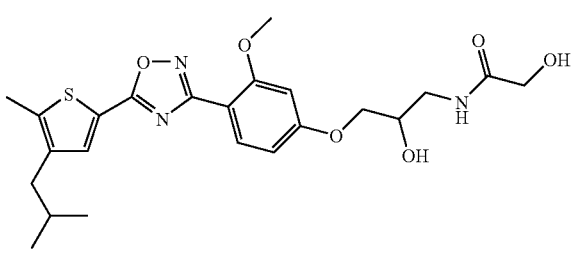

To a solution of rac-3-{4-[5-(4-isobutyl-5-methyl-thiophen-2-yl)-[1,2,4]oxadiazol-3-yl]-3-methoxy-phenoxy}-propane-1,2-diol (400 mg, 0.956 mmol) and DIPEA (257 mg, 1.99 mmol) in THF (40 mL), methanesulfonylchloride (125 mg, 1.095 mmol) dissolved in THF (10 mL) is added at −10° C. The reaction is allowed to warm to rt and is stirred for 15 h. Another portion of methanesulfonylchloride (30 mg, 0.258 mmol) in THF (2 mL) and DIPEA (128 mg, 0.993 mmol) is added and stirring is continued for 24 h. The mixture is evaporated and the residue is dissolved in 7 N NH₃ in MeOH (17 mL). The resulting solution is stirred at 70° C. for 5 h before it is evaporated. The remaining residue is dissolved in DMF (15 mL) and glycolic acid (110 mg, 1.45 mmol), DIPEA (257 mg, 1.99 mmol) and TBTU (370 mg, 1.15 mmol) is added. The mixture is stirred at rt for 5 h, evaporated and the residue is purified on prep. TLC plates with EA to give 2-hydroxy-N-(2-hydroxy-3-{4-[5-(4-isobutyl-5-methyl-thiophen-2-yl)-[1,2,4]oxadiazol-3-yl]-3-methoxy-phenoxy}-propyl)-acetamide (135 mg) as colourless foam; LC-MS: $t_R$=0.95 min, [M+1]=476.29; ¹H NMR (D₆-acetone): δ 7.92 (d, J=8.8 Hz, 1H), 7.71 (s, 1H), 7.57 (s br, 1H), 6.77 (d, J=2.3 Hz, 1H), 6.71 (dd, J=2.3, 8.8 Hz, 1H), 4.74-4.67 (m, 2H), 4.15-4.07 (m, 3H), 3.99 (d, J=5.0 Hz, 2H), 3.93 (s, 3H), 3.66-3.57 (m, 1H), 3.48-3.39 (m, 1H), 2.52 (d, J=7.0 Hz, 2H), 2.49 (s, 3H), 1.95 (hept, J=7.0 Hz, 1H), 0.95 (d, J=6.4 Hz, 6H).

Example 47

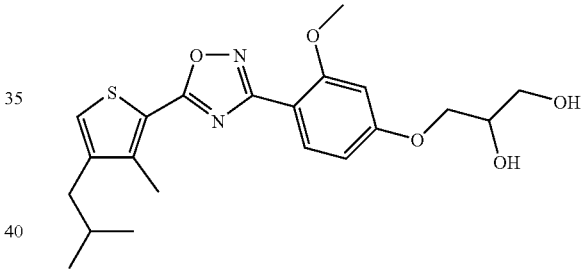

rac-3-{4-[5-(4-Isobutyl-3-methyl-thiophen-2-yl)-[1,2,4]oxadiazol-3-yl]-3-methoxy-phenoxy}-propane-1,2-diol is prepared from 4-isobutyl-3-methyl-thiophene-2-carboxylic acid and 4-allyloxy-N-hydroxy-2-methoxy-benzamidine in analogy to Example 45; LC-MS: $t_R$=1.00 min, [M+1]=419.20.

Example 48

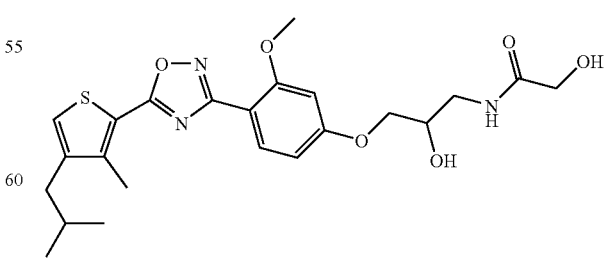

rac-2-Hydroxy-N-(2-hydroxy-3-{4-[5-(4-isobutyl-3-methyl-thiophen-2-yl)-[1,2,4]oxadiazol-3-yl]-3-methoxy-phenoxy}-propyl)acetamide is prepared from rac-3-{4-[5-(4- isobutyl-3-methyl-thiophen-2-yl)-[1,2,4]oxadiazol-3-yl]-3-methoxy-phenoxy}-propane-1,2-diol in analogy to Example 46; LC-MS: $t_R$=0.96 min, [M+1]=476.31.

Example 49

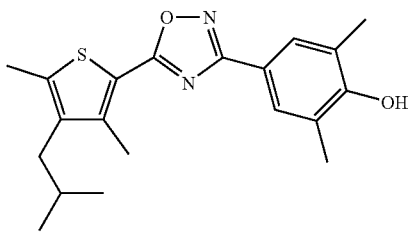

4-[5-(4-Isobutyl-3,5-dimethyl-thiophen-2-yl)-[1,2,4]oxadiazol-3-yl]-2,6-dimethyl-phenol is prepared from 4-isobutyl-3,5-dimethyl-thiophene-2-carboxylic acid and 4,N-dihydroxy-3,5-dimethyl-benzamidine in analogy to Example 21; LC-MS: $t_R$=1.20 min, [M+1]=357.35; $^1$H NMR (D$_6$-DMSO): δ 8.91 (s, 1H), 7.60 (s, 2H), 2.53 (s, 3H), 2.44-2.40 (m, 5H), 2.23 (s, 6H), 1.81-1.72 (m, 1H), 0.89 (d, J=6.4 Hz, 6H).

Example 50

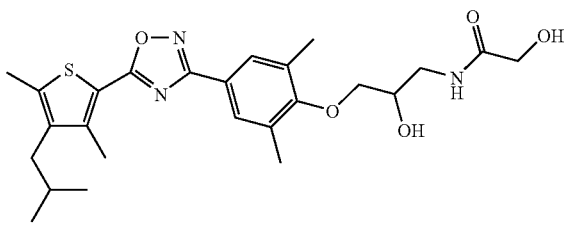

rac-2-Hydroxy-N-(2-hydroxy-3-{4-[5-(4-isobutyl-3,5-dimethyl-thiophen-2-yl)-[1,2,4]oxadiazol-3-yl]-2,6-dimethyl-phenoxy}-propyl)acetamide is prepared from 4-[5-(4-isobutyl-3,5-dimethyl-thiophen-2-yl)-[1,2,4]oxadiazol-3-yl]-2,6-dimethyl-phenol in analogy to the procedures described in Examples 22 and 17; LC-MS: $t_R$=1.05 min, [M+1]=488.09; $^1$H NMR (D$_6$-DMSO): δ 7.70 (s, 2H), 7.68 (t br, J=4 Hz, 1H), 5.53 (t, J=5.9 Hz, 1H), 5.27 (d, J=5.3 Hz, 1H), 3.97-3.87 (m, 1H), 3.81 (d, J=5.9 Hz, 2H), 3.80-3.68 (m, 2H), 3.46-3.37 (m, 1H), 3.28-3.19 (m, 1H), 2.54 (s, 3H), 2.44-2.39 (m, 5H), 2.30 (s, 6H), 1.83-1.72 (m, 1H), 0.89 (d, J=7.0 Hz, 6H).

Example 51

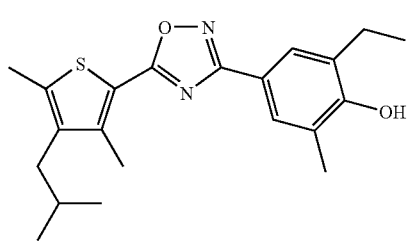

2-Ethyl-4-[5-(4-isobutyl-3,5-dimethyl-thiophen-2-yl)-[1,2,4]oxadiazol-3-yl]-6-methyl-phenol is prepared in analogy to Example 21 starting from 4-isobutyl-3,5-dimethyl-thiophene-2-carboxylic acid and 4,N-dihydroxy-3-ethyl-5-methyl-benzamidine; LC-MS: $t_R$=1.20 min, [M+1]=371.04.

Example 52

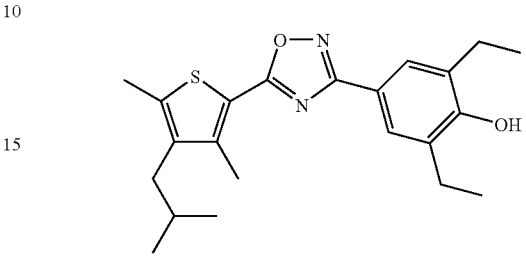

2,6-Diethyl-4-[5-(4-isobutyl-3,5-dimethyl-thiophen-2-yl)-[1,2,4]oxadiazol-3-yl]-phenol is prepared from 4-isobutyl-3,5-dimethyl-thiophene-2-carboxylic acid and 4,N-dihydroxy-3,5-diethyl-benzamidine in analogy to Example 21; LC-MS: $t_R$=1.24 min, [M+1]=385.28.

Example 53

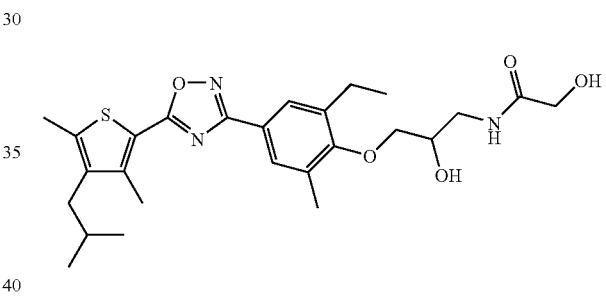

rac-N-(3-{2-Ethyl-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide is prepared from 4-[5-(4-isobutyl-3,5-dimethyl-thiophen-2-yl)-[1,2,4]oxadiazol-3-yl]-2-ethyl-6-methyl-phenol in analogy to the procedures described in Examples 22 and 17; LC-MS: $t_R$=1.10 min, [M+1]=502.32.

Example 54

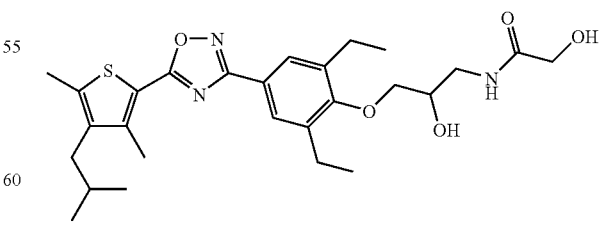

N-(3-{2,6-Diethyl-4-[5-(4-isobutyl-3,5-dimethyl-thiophen-2-yl)-[1,2,4]oxadiazol-3-yl]-phenoxy}-2-hydroxy-propyl)-2-hydroxy-acetamide is prepared from 4-[5-(4-isobutyl-3,5-dimethyl-thiophen-2-yl)-[1,2,4]oxadiazol-3- yl]-2,6-diethyl-phenol in analogy to the procedures described in Examples 22 and 17; LC-MS: $t_R$=1.10 min, [M+1]= 516.42.

Example 55

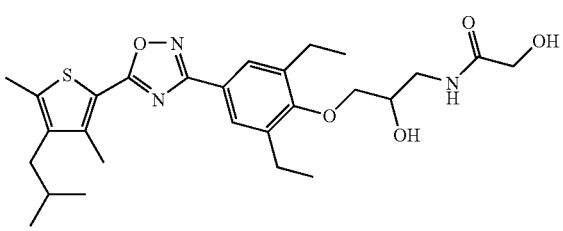

rac-N-(3-{2,6-Diethyl-4-[5-(4-isobutyl-5-methyl-thiophen-2-yl)-[1,2,4]oxadiazol-3-yl]-phenoxy}-2-hydroxy-propyl)-2-hydroxy-acetamide is prepared starting from Intermediate A1 and 3,5-diethyl-4-N-dihydroxy-benzamidine following the procedures described in Examples 21, 22 and 17; LC-MS: $t_R$=1.09 min, [M+1]=502.36.

Example 56

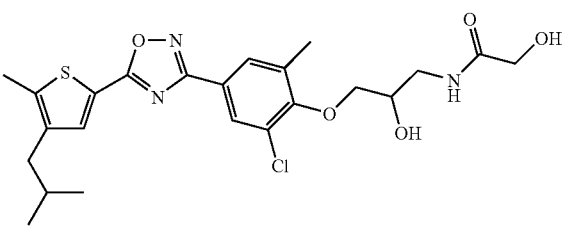

rac-N-(3-{2-Chloro-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide is prepared starting from Intermediate A1 and 3-chloro-4,N-dihydroxy-5-methyl-benzamidine following the procedures described in Examples 21, 22 and 17; LC-MS: $t_R$=1.07 min, [M+1]=494.44.

Example 57

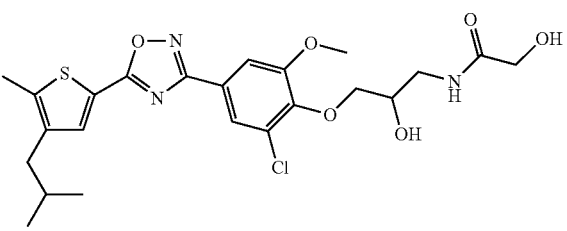

rac-N-(3-{2-Chloro-4-[5-(4-isobutyl-5-methyl-thiophen-2-yl)-[1,2,4]oxadiazol-3-yl]-6-methoxy-phenoxy}-2-hydroxy-propyl)-2-hydroxy-acetamide is prepared starting from Intermediate A1 and 3-chloro-4,N-dihydroxy-5-methoxy-benzamidine following the procedures described in Examples 21, 22 and 17; LC-MS: $t_R$=1.06 min, [M+1]= 510.40.

Example 58

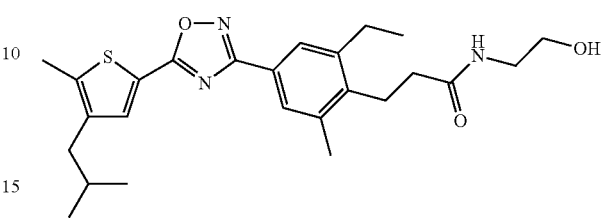

To a solution of 3-{2-ethyl-4-[5-(4-isobutyl-5-methyl-thiophen-2-yl)-[1,2,4]oxadiazol-3-yl]-6-methyl-phenyl}-propionic acid (42 mg, 100 µmol) and DIPEA (39 mg, 300 µmol) in DCM (2 mL), TBTU (32 mg, 100 µmol) followed by ethanolamine (18 mg, 300 µmol) is added. The mixture is stirred at 0° C. for 16 h before it is diluted with EA, washed with 1 N aq. NaOH solution, dried over $Na_2SO_4$ and filtered. The solvent is evaporated and the residue is dried under HV to give 3-{2-ethyl-4-[5-(4-isobutyl-5-methyl-thiophen-2-yl)-[1,2,4]oxadiazol-3-yl]-6-methyl-phenyl}-N-(2-hydroxy-ethyl)-propionamide (39 mg) as a beige solid; LC-MS: $t_R$=1.10 min, [M+1]=456.47.

Example 59

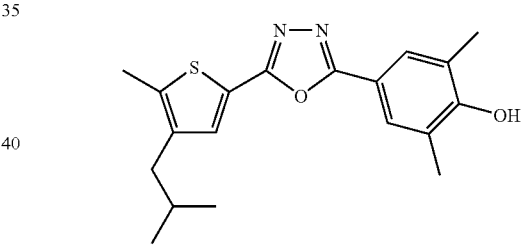

To a solution of Intermediate A1 (291 mg, 1.47 mmol) in DCM (10 mL), DIPEA (573 mg, 4.44 mmol) and TBTU (474 mg, 1.48 mmol) is added. The mixture is stirred for 15 min before 4-benzyloxy-3,5-dimethyl-benzoic acid hydrazide (396 mg, 1.47 mmol) is added. Stirring is continued at rt for 16 h. The mixture is diluted with diethyl ether, washed twice with 1 N aq. NaOH solution, once with 1 N aq. HCl solution, dried over $Na_2SO_4$, and filtered. The solvent is evaporated to give 4-benzyloxy-3,5-dimethyl-benzoic acid N'-(4-isobutyl-5-methyl-thiophene-2-carbonyl)-hydrazide (371 mg) as a beige solid; LC-MS: $t_R$=1.07 min, [M+1]=451.40. To a solution of this material in THF (5 mL), Burgess reagent (305 mg, 1.28 mmol) is added. The mixture is heated to 110° C. for 5 min in a microwave oven. The mixture is cooled to rt, diluted with diethyl ether and washed with brine. The organic extract is dried over $Na_2SO_4$, filtered and concentrated to give 2-(4-benzyloxy-3,5-dimethyl-phenyl)-5-(4-isobutyl-5-methyl-thiophen-2-yl)-[1,3,4]oxadiazole (348 mg) as an orange oil; LC-MS: $t_R$=1.26 min, [M+1]=433.40. This material is dissolved in THF:ethanol 1:1 (20 mL) and treated with a suspension of Pd/C (100 mg, 10% Pd) in ethanol. The mixture is stirred at rt for 3 h under 1 bar or $H_2$. The catalyst is removed by filtration and the filtrate is evaporated to give 4-[5-(4-isobutyl-5-methyl-thiophen-2-yl)-[1,3,4]oxadiazol-2-yl]-2,6-dimethyl-phenol (274 mg) as a grey solid, LC-MS: $t_R$=1.12 min, [M+1]=343.25.

Example 60

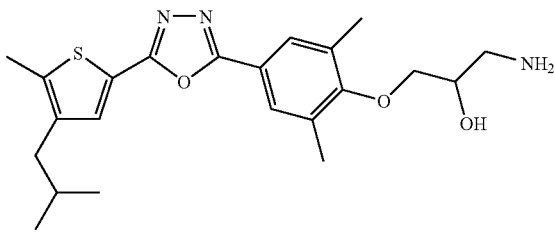

rac-1-Amino-3-{4-[5-(4-isobutyl-5-methyl-thiophen-2-yl)-[1,3,4]oxadiazol-2-yl]-2,6-dimethyl-phenoxy}-propan-2-ol is prepared starting from Example 59 in analogy to Example 22; LC-MS: $t_R$=0.85 min, [M+1]=416.21.

Example 61

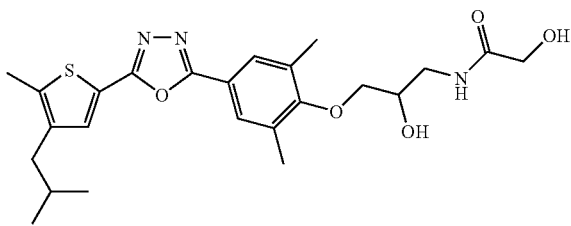

rac-2-Hydroxy-N-(2-hydroxy-3-{4-[5-(4-isobutyl-5-methyl-thiophen-2-yl)-[1,3,4]oxa-diazol-2-yl]-2,6-dimethyl-phenoxy}-propyl)-acetamide is obtained as a beige solid starting from Example 60 in analogy to Example 17; LC-MS: $t_R$=0.97 min, [M+1]=474.32.

Examples 62 to 64

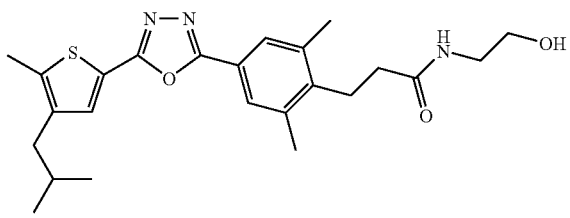

Starting from Intermediate C1 and 4-benzyloxy-3-ethyl-5-methyl-benzoic acid, the following examples are prepared following the procedures given for Examples 59, 22 and 17 using either racemic or enantiomerically pure epichlorohydrine:

| Example | epichlorohydrine used | Stereochemistry of Example | LC-MS $t_R$ [min] | [M + H]+ |
|---|---|---|---|---|
| 62 | racemic | racemic | 1.00 | 488.47 |
| 63 | (S) | (R) | 1.00 | 488.42 |
| 64 | (R) | (S) | 1.00 | 488.45 |

Example 62

$^{13}$C NMR (D$_6$-DMSO): δ 13.87, 15.53, 16.77, 22.83, 22.90, 29.82, 37.16, 42.14, 62.09, 69.24, 75.96, 119.41, 120.07, 126.18, 127.88, 132.82, 133.24, 138.68, 139.74, 139.94, 158.80, 160.73, 163.72, 172.62.

Example 65

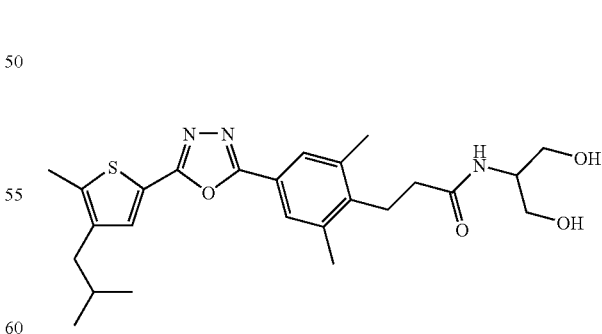

N-(2-Hydroxy-ethyl)-3-{4-[5-(4-isobutyl-5-methyl-thiophen-2-yl)-[1,3,4]oxadiazol-2-yl]-2,6-dimethyl-phenyl}-propionamide is prepared starting from Intermediate D2 and ethanolamine in analogy to Example 58; LC-MS: $t_R$=1.00 min, [M+1]=488.42; $^1$H NMR (D$_6$-DMSO): δ 0.88 (d, J=6.4 Hz, 6H), 1.87 (hept, J=6.4 Hz, 1H), 2.22 (m, 2H), 2.38 (s, 6H), 2.39-2.45 (m, 5H), 2.80-2.91 (m, 2H), 3.11 (q, J=5.9 Hz, 2H), 3.34-3.42 (m, 2H), 4.65 (t, J=5.3 Hz, 1H), 7.65 (s, 1H), 7.68 (s, 2H), 7.90 (t, J=5.6 Hz, 1H).

Example 66

N-(2-Hydroxy-1-hydroxymethyl-ethyl)-3-{4-[5-(4-isobutyl-5-methyl-thiophen-2-yl)-[1,3,4]oxadiazol-2-yl]-2,6-dimethyl-phenyl}-propionamide is prepared starting from Intermediate D2 and 2-amino-propane-1,3-diol in analogy to Example 58; LC-MS: $t_R$=0.96 min, [M+1]=472.25.

Example 67

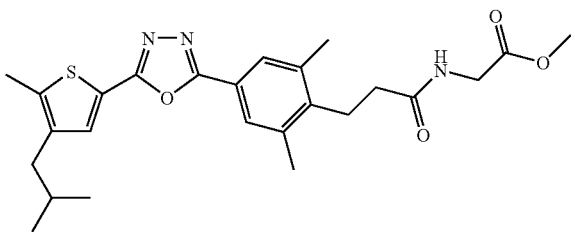

(3-{4-[5-(4-Isobutyl-5-methyl-thiophen-2-yl)-[1,3,4]oxadiazol-2-yl]-2,6-dimethyl-phenyl}-propionylamino)-acetic acid methyl ester is prepared starting from Intermediate D2 and glycine methyl ester in analogy to Example 58; LC-MS: $t_R$=1.10 min, [M+1]=470.41.

Example 68

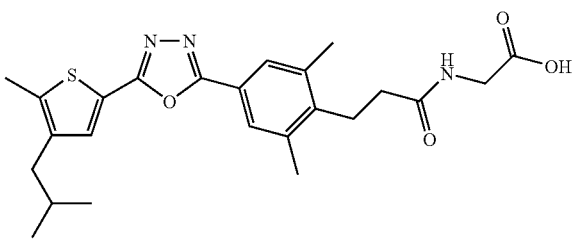

A solution of (3-{4-[5-(4-isobutyl-5-methyl-thiophen-2-yl)-[1,3,4]oxadiazol-2-yl]-2,6-dimethyl-phenyl}-propionylamino)-acetic acid methyl ester in THF (1 mL), MeOH (1 mL) and 2 N aq. LiOH solution (0.25 mL) is stirred at rt for 4 h. The precipitate that formes is collected, washed with water and dried under HV to give (3-{4-[5-(4-isobutyl-5-methyl-thiophen-2-yl)-[1,3,4]oxadiazol-2-yl]-2,6-dimethyl-phenyl}-propionylamino)-acetic acid (9 mg) as a white powder; LC-MS: $t_R$=0.99 min, [M+1]=456.17.

Example 69

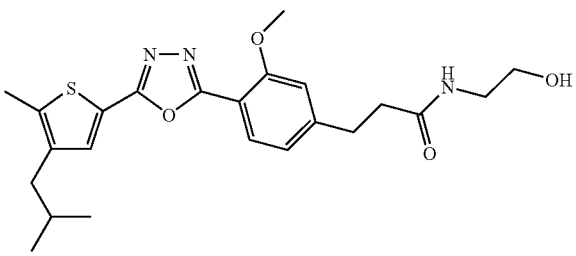

N-(2-Hydroxy-ethyl)-3-{4-[5-(4-isobutyl-5-methyl-thiophen-2-yl)-[1,3,4]oxadiazol-2-yl]-3-methoxy-phenyl}-propionamide is prepared in analogy to Example 58 starting from Intermediate D3 and ethanolamine; LC-MS: $t_R$=0.99 min, [M+1]=444.35; $^1$H NMR (CDCl$_3$): δ 0.88 (d, J=6.7 Hz, 6 H), 1.83 (hept, J=6.7 Hz, 1 H), 2.34-2.41 (m, 5 H), 2.46 (t, J=7.6 Hz, 2 H), 2.95 (t, J=7.3 Hz, 2 H), 3.28-3.37 (m, 2 H), 3.57-3.63 (m, 2 H), 3.84 (s, 3 H), 5.98 (t, J=5.3 Hz, 1 H), 7.18-7.21 (m, 1 H), 7.44-7.52 (m, 3 H).

Example 70

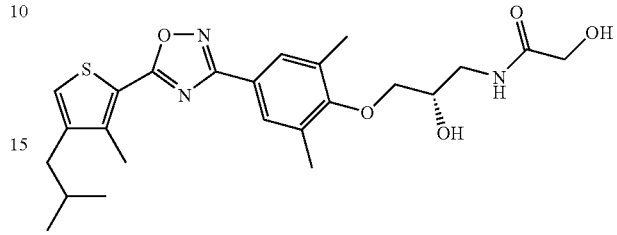

(S)-2-Hydroxy-N-(2-hydroxy-3-{4-[5-(4-isobutyl-3-methyl-thiophen-2-yl)-[1,2,4]oxa-diazol-3-yl]-2,6-dimethyl-phenoxy}-propyl)-acetamide is prepared following the procedures given in Examples 22 and 17 using (R)-epichlorohydrine and starting from Example 21; LC-MS: $t_R$=1.05 min, [M+1]=474.10.

Example 71

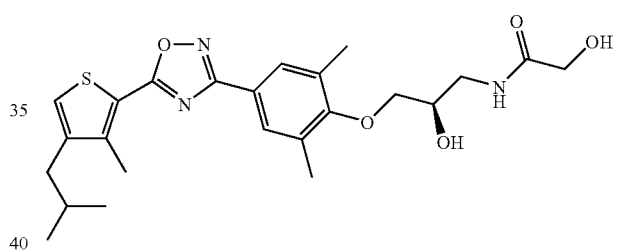

(R)-2-Hydroxy-N-(2-hydroxy-3-{4-[5-(4-isobutyl-3-methyl-thiophen-2-yl)-[1,2,4]oxa-diazol-3-yl]-2,6-dimethyl-phenoxy}-propyl)-acetamide is prepared following the procedures given in Examples 22 and 17 using (S)-epichlorohydrine and starting from Example 21; LC-MS: $t_R$=1.05 min, [M+1]=474.37.

Example 72

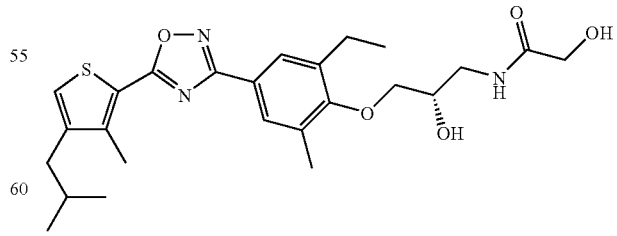

(S)—N-(3-{2-Ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide is prepared following the procedures given in Examples 21, 22 and 17 starting from Intermediate A3 and 3-ethyl-4,N-dihydroxy-5-methyl-benzamidine; LC-MS: $t_R$=1.07 min, [M+1]=488.16.

Example 73

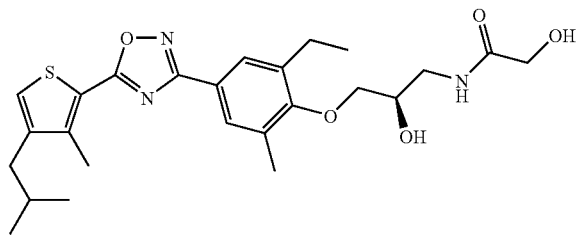

(R)—N-(3-{2-Ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide is prepared following the procedures given in Examples 21, 22 and 17 starting from Intermediate A3 and 3-ethyl-4,N-dihydroxy-5-methyl-benzamidine; LC-MS: $t_R$=1.07 min, [M+1]=488.16.

Example 74

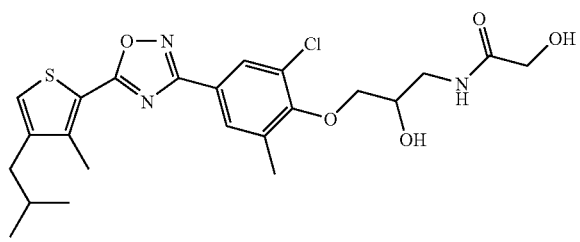

rac-N-(3-{2-Chloro-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide is prepared following the procedures given in Examples 21, 22 and 17 starting from Intermediate A3 and 3-chloro-4,N-dihydroxy-5-methyl-benzamidine; LC-MS: $t_R$=1.07 min, [M+1]=493.43.

Example 75

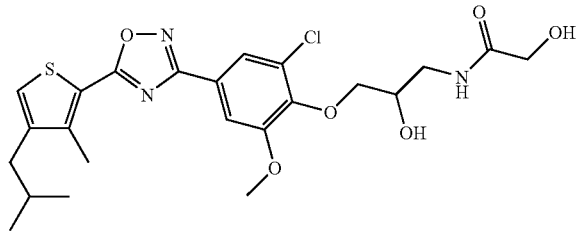

rac-N-(3-{2-Chloro-4-[5-(4-isobutyl-3-methyl-thiophen-2-yl)-[1,2,4]oxadiazol-3-yl]-6-methoxy-phenoxy}-2-hydroxy-propyl)-2-hydroxy-acetamide is prepared following the procedures given in Examples 21, 22 and 17 starting from Intermediate A3 and 3-chloro-4,N-dihydroxy-5-methoxy-benzamidine; LC-MS: $t_R$=1.06 min, [M+1]=510.38.

Example 76

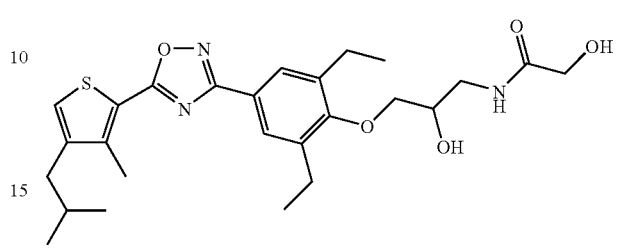

rac-N-(3-{2,6-Diethyl-4-[5-(4-isobutyl-3-methyl-thiophen-2-yl)-[1,2,4]oxadiazol-3-yl]-phenoxy}-2-hydroxy-propyl)-2-hydroxy-acetamide is prepared following the procedures given in Examples 21, 22 and 17 starting from Intermediate A3 and 3,5-diethyl-4,N-dihydroxy-benzamidine; LC-MS: $t_R$=1.07 min, [M+1]=503.25.

Example 77

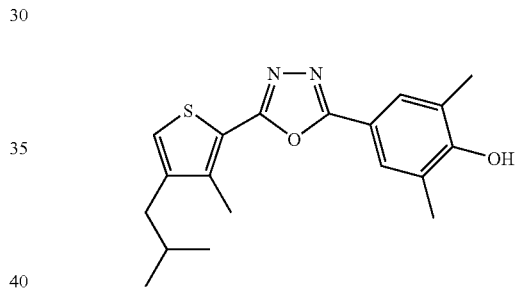

4-[5-(4-Isobutyl-3-methyl-thiophen-2-yl)-[1,3,4]oxadiazol-2-yl]-2,6-dimethyl-phenol is prepared in analogy to Example 59 starting from Intermediate A3; LC-MS: $t_R$=1.12 min, [M+1]=343.21; $^1$H NMR (CD$_3$OD): δ 0.97 (d, J=6.7 Hz, 6 H), 1.84-1.96 (m, 1H), 2.30 (s, 6 H), 2.52 (d, J=7.0 Hz, 2 H), 2.56 (s, 3 H), 7.32 (s, 1 H), 7.66 (s, 2 H).

Example 78

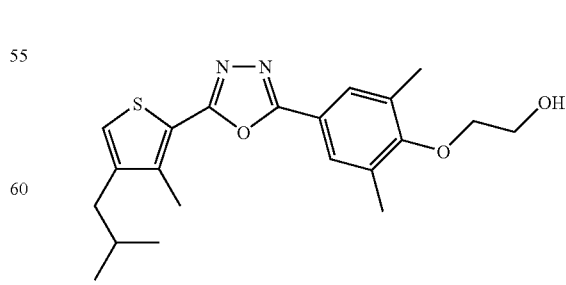

Alkylation of Example 77 with 2-bromoethanol following the procedure given in Example 12 gives 2-{4-[5-(4-isobutyl- 3-methyl-thiophen-2-yl)-[1,3,4]oxadiazol-2-yl]-2,6-dimethyl-phenoxy}-ethanol; LC-MS: $t_R$=1.09 min, [M+1]= 387.30.

Example 79

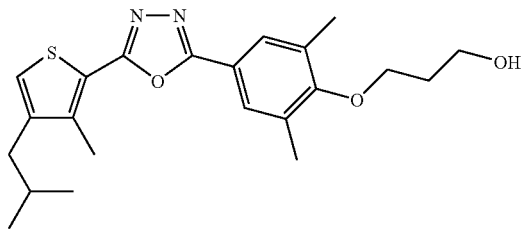

Alkylation of Example 77 with 3-bromopropanol following the procedure given in Example 12 gives 3-{4-[5-(4-isobutyl-3-methyl-thiophen-2-yl)-[1,3,4]oxadiazol-2-yl]-2,6-dimethyl-phenoxy}-propan-1-ol; LC-MS: $t_R$=1.12 min, [M+1]=401.30.

Example 80

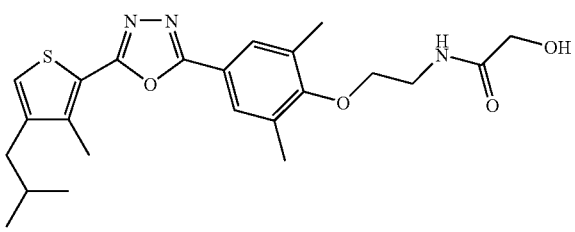

2-Hydroxy-N-(2-{4-[5-(4-isobutyl-3-methyl-thiophen-2-yl)-[1,3,4]oxadiazol-2-yl]-2,6-dimethyl-phenoxy}-ethyl)-acetamide is obtained from Example 78 following the reaction sequence described in Example 35; LC-MS: $t_R$=1.05 min, [M+1]=444.30.

Example 81

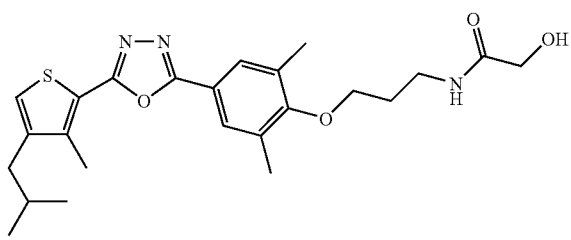

2-Hydroxy-N-(3-{4-[5-(4-isobutyl-3-methyl-thiophen-2-yl)-[1,3,4]oxadiazol-2-yl]-2,6-dimethyl-phenoxy}-propyl)-acetamide is obtained from Example 79 following the reaction sequence described in Example 35; LC-MS: $t_R$=1.07 min, [M+1]=458.30.

Example 82

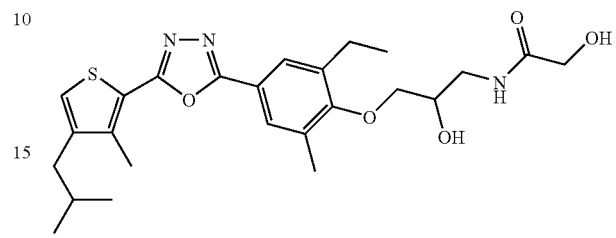

N-(3-{2-Ethyl-4-[5-(4-isobutyl-3-methyl-thiophen-2-yl)-[1,3,4]oxadiazol-2-yl]-6-methyl-phenoxy}-2-hydroxy-propyl)-2-hydroxy-acetamide is prepared from Intermediate C2 and 4-benzyloxy-3-ethyl-5-methyl-benzoic acid following the procedures given for Examples 59, 22 and 17; LC-MS: $t_R$=1.00 min, [M+1]=488.45.

Examples 83 to 85

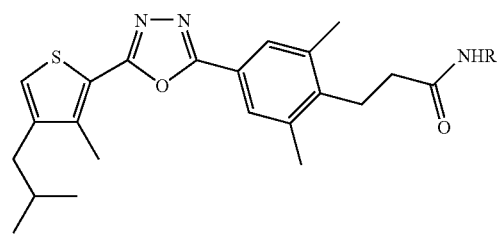

Starting from Intermediate D4 the following examples are prepared in analogy to previous examples:

| Example | in analogy to Example | R | LC-MS $t_R$ [min] | [M + H]+ |
|---|---|---|---|---|
| 83 | 66 | ![OH/OH] | 0.96 | 472.46 |
| 84 | 67 | ![OMe ester] | 1.07 | 470.21 |
| 85 | 68 | ![OH acid] | 1.02 | 456.42 |

Example 86

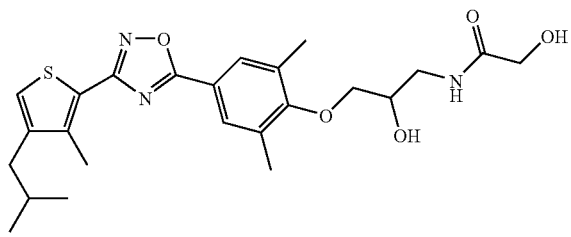

2-Hydroxy-N-(2-hydroxy-3-{4-[3-(4-isobutyl-3-methyl-thiophen-2-yl)-[1,2,4]oxa-diazol-5-yl]-2,6-dimethyl-phenoxy}-propyl)-acetamide is prepared starting from Intermediate E1 and 3,5-dimethyl-4-hydroxy-benzoic acid following the procedures given in Examples 21, 22 and 17; LC-MS: $t_R$=1.05 min, [M+1]=474.26; $^1$H NMR (D$_6$-DMSO): δ 0.90 (d, J=6.7 Hz, 6 H), 1.78-1.90 (m, 1H), 2.33 (s, 6 H), 3.68-3.84 (m, 4H), 3.87-3.97 (m, 1 H), 4.06-4.12 (m, 1 H), 5.25-5.31 (m, 1 H), 5.53 (t, J=5.6 Hz, 1 H), 7.45 (s, 1 H), 7.68 (t, J=5.9 Hz), 7.83 (s, 2 H) (some signals under solvent resonance).

Example 87

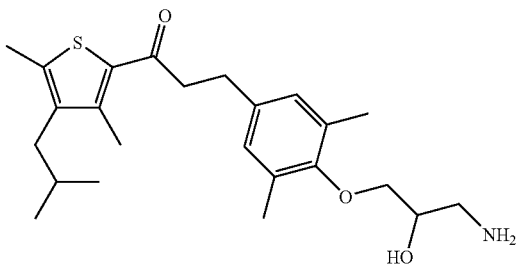

rac-3-[4-(3-Amino-2-hydroxy-propoxy)-3,5-dimethyl-phenyl]-1-(4-isobutyl-3,5-dimethyl-thiophen-2-yl)-propan-1-one is produced starting from Example 9 following the procedures given in Example 22; LC-MS: $t_R$=0.87 min, [M+1]=418.27.

Example 88

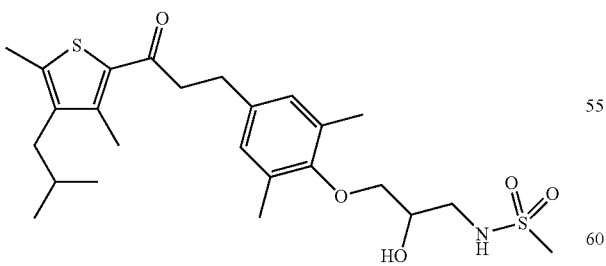

To a solution of rac-3-[4-(3-amino-2-hydroxy-propoxy)-3,5-dimethyl-phenyl]-1-(4-isobutyl-3,5-dimethyl-thiophen-2-yl)-propan-1-one (545 mg, 1.31 mmol) in DCM (27 mL), DIPEA (270 mg, 2.09 mmol) is added. The mixture is cooled to 0° C. before methanesulfonylchloride (180 mg, 1.51 mmol) is added. Stirring is continued at 0° C. for 1 h. The mixute is diluted with DCM, washed with water, dried over MgSO$_4$, filtered and concentrated. The crude product is purified by chromatography on prep. TLC plates with DCM containing 4% of MeOH to give N-(2-hydroxy-3-{4-[3-(4-isobutyl-3,5-dimethyl-thiophen-2-yl)-3-oxo-propyl]-2,6-dimethyl-phenoxy}-propyl)-methanesulfonamide (545 mg) as a yellow oil; LC-MS: $t_R$=1.06 min, [M+1]=496.24.

Example 89

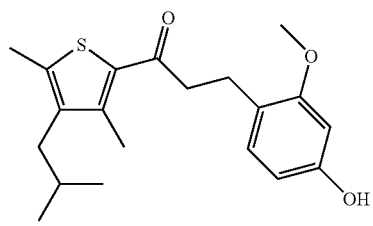

To a solution of Intermediate B5 (300 mg, 1.27 mmol) in MeOH (11 mL), NaOH (2.03 g, 50.7 mmol) followed by 4-hydroxy-2-methoxy-benzaldehyde is added. The mixture is stirred at 70° C. for 1 h then at rt for 16 h. The mixture is diluted with diethyl ether, 25% aq. HCl and sat. NaHCO$_3$ solution so that the pH of the aq. phase is about 7. The org. phase is separated and the aq. phase is extracted once more with diethyl ether. The combined organic extracts are dried over MgSO$_4$, filtered and concentrated. The crude product is purified by CC on silica gel eluting with heptane:EA 7:3 to give 3-(4-hydroxy-2-methoxy-phenyl)-1-(4-isobutyl-3,5-dimethyl-thiophen-2-yl)-propenone (270 mg) as a yellow solid; LC-MS: $t_R$=1.07 min, [M+1]=345.18. This material is hydrogenated as described in Example 7 to give 3-(4-hydroxy-2-methoxy-phenyl)-1-(4-isobutyl-3,5-dimethyl-thiophen-2-yl)-propan-1-one (203 mg) as an orange oil; LC-MS: $t_R$=1.07 min, [M+1]=347.19.

Examples 90 to 99

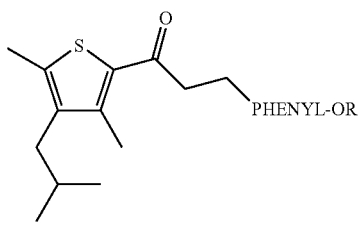

The following examples are prepared in analogy to previous examples:

| Example | starting material | prepared in analogy to Example(s) | PHENYL | R | LC-MS $t_R$ [min] | $[M+H]^+$ |
|---|---|---|---|---|---|---|
| 90 | Intermediate B5, 3-ethyl-4-hydroxy-5-ethyl benzaldehyde | 1, 7 | 3-ethyl-5-methyl phenyl | H | 1.15 | 359.26 |
| 91 | Intermediate B5, 3,5-diethyl-4-hydroxy-benzaldehyde | 1, 7 | 3,5-diethyl phenyl | H | 1.17 | 373.28 |
| 92 | Example 90 | 8 | 3-ethyl-5-methyl phenyl | CH₂CH(OH)CH₂OH | 1.08 | 433.40 |
| 93 | Example 91 | 8 | 3,5-diethyl phenyl | CH₂CH(OH)CH₂OH | 1.11 | 447.49 |
| 94 | Example 9 | 22, 17 | 3,5-dimethyl phenyl | CH₂CH(OH)CH₂NHC(O)CH₂OH | 1.02 | 476.45 |
| 95 | Example 90 | 22, 17 | 3-ethyl-5-methyl phenyl | CH₂CH(OH)CH₂NHC(O)CH₂OH | 1.02 | 490.29 |
| 96 | Example 91 | 22, 17 | 3,5-diethyl phenyl | CH₂CH(OH)CH₂NHC(O)CH₂OH | 1.04 | 504.28 |
| 97 | Example 89 | 22, 17 | 3-methoxy phenyl | CH₂CH(OH)CH₂NHC(O)CH₂OH | 0.99 | 478.46 |
| 98 | Example 90 | 22, 88 | 3-ethyl-5-methyl phenyl | CH₂CH(OH)CH₂NHS(O)₂CH₃ | 1.10 | 510.42 |

-continued

| Example | starting material | prepared in analogy to Example(s) | PHENYL | R | LC-MS $t_R$ [min] | [M + H]⁺ |
|---|---|---|---|---|---|---|
| 99 | Example 91 | 22, 88 | 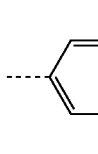 | 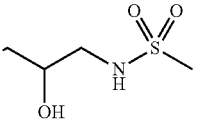 | 1.12 | 524.45 |

Example 95

¹H NMR (CDCl₃): δ 0.90 (d, J=6.4 Hz, 6 H), 1.20 (t, J=7.3 Hz, 3 H), 1.77 (hept, J=6.4 Hz, 1H), 2.25 (s, 3 H), 2.35 (d, J=6.4 Hz, 2 H), 2.39 (s, 3 H), 2.46 (s, 3 H), 2.61 (q, J=7.6 Hz, 2 H), 2.88-2.98 (m, 2 H), 3.00-3.10 (m, 2 H), 3.39-3.51 (m, 1 H), 3.68-3.84 (m, 4 H), 4.09-4.15 (m, 1 H), 4.14 (s, 2 H), 6.88 (s, 1 H), 6.89 (s, 1 H), 7.05 (t, J=5.0 Hz, 1 H).

Example 100

rac-N-(3-{2-Chloro-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide is prepared following the procedures given in Examples 21, 22, and 17 starting from Intermediate A9 and 3-chloro-4,N-dihydroxy-5-methyl-benzamidine; LC-MS: $t_R$=1.10 min, [M+1]=508.42.

Example 101

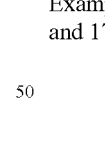

3-{4-[5-(4-Isobutyl-3,5-dimethyl-thiophen-2-yl)-[1,3,4]oxadiazol-2-yl]-2,6-dimethyl-phenoxy}-propane-1,2-diol is prepared starting from Intermediate C3 in analogy to Example 28; LC-MS: $t_R$=1.05 min, [M+1]=431.39.

Example 102

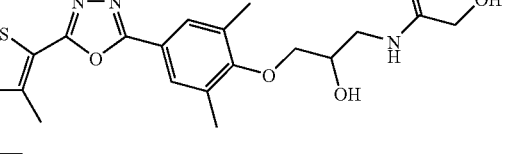

rac-2-Hydroxy-N-(2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide is prepared from Example 101 following the procedures given in Examples 35 and 17; LC-MS: $t_R$=0.98 min, [M+1]=488.21.

Example 103

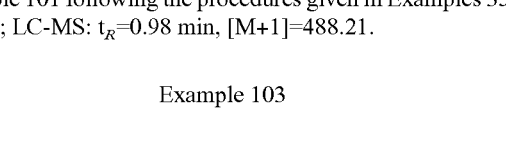

(S)-2-Hydroxy-N-(2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide is obtained by chiral Example 104

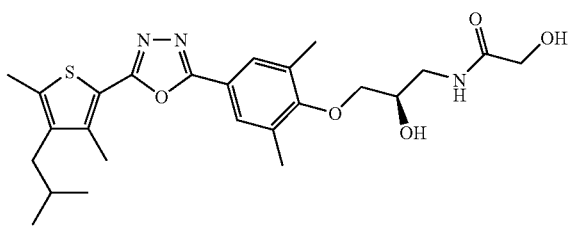

(R)-2-Hydroxy-N-(2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide is obtained by chiral resolution of the compound of Example 102 by HPLC on a chiral stationary phase (Chiralpack AD); LC-MS: $t_R$=0.98 min, [M+1]=488.43.

Example 104

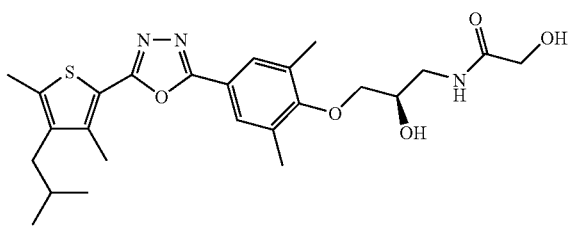

(R)-2-Hydroxy-N-(2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide is obtained by chiral resolution of the compound of Example 102 by HPLC on a chiral stationary phase (Chiralpack AD); LC-MS: $t_R$=0.98 min, [M+1]=488.46.

Example 105

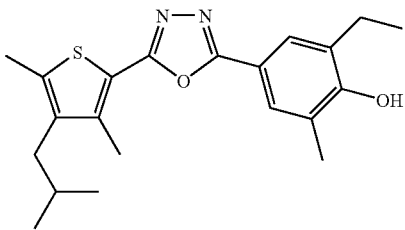

2-Ethyl-4-[5-(4-isobutyl-3,5-dimethyl-thiophen-2-yl)-[1,3,4]oxadiazol-2-yl]-6-methyl-phenol is prepared in analogy to Example 59 starting from Intermediate C3 and 4-benzyloxy-3-ethyl-5-methyl-benzoic acid; LC-MS: $t_R$=1.17 min, [M+1]=371.10.

Example 106

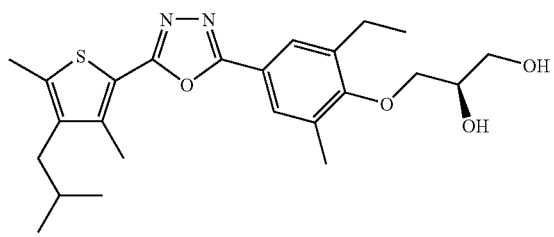

(R)-3-{2-Ethyl-4-[5-(4-isobutyl-3,5-dimethyl-thiophen-2-yl)-[1,3,4]oxadiazol-2-yl]-6-methyl-phenoxy}-propane-1,2-diol is prepared from Example 105 in analogy to Example 8; LC-MS: $t_R$=1.06 min, [M+1]=445.40.

Example 107

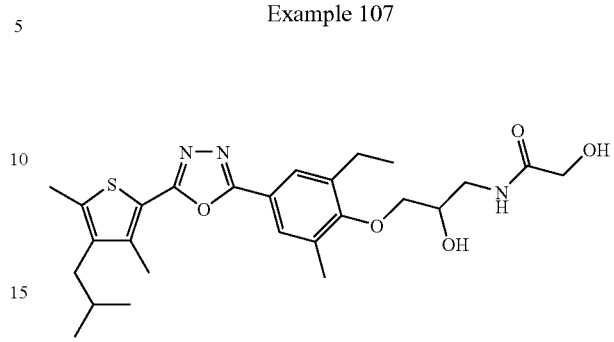

rac-N-(3-{2-Ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide is prepared from Example 105 following the procedures given in Examples 35 and 17; LC-MS: $t_R$=1.03 min, [M+1]=502.50.

Example 108

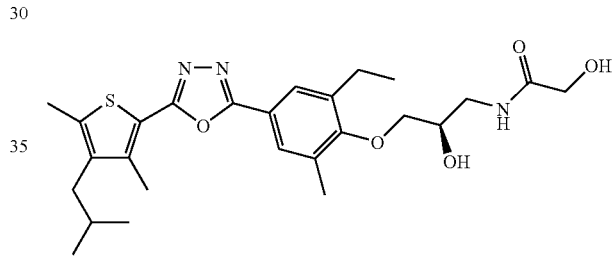

(R)—N-(3-{2-Ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide is prepared from Example 105 following the procedures given in Examples 35 and 17 using (S)-epichlorohydrine; LC-MS: $t_R$=1.01 min, [M+1]=502.42.

Example 109

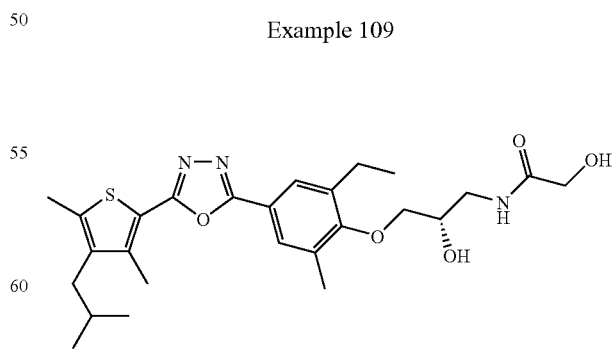

(S)—N-(3-{2-Ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide is prepared from Example 105 following the procedures given in Examples 35 and 17 using (R)-epichlorohydrine; LC-MS: $t_R$=1.01 min, [M+1]=502.41.

Example 110

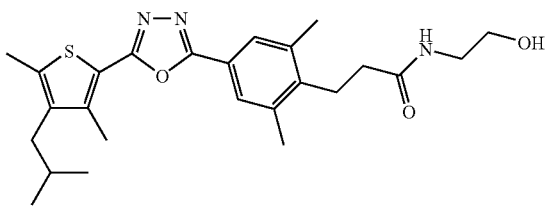

N-(2-Hydroxy-ethyl)-3-{4-[5-(4-isobutyl-3,5-dimethyl-thiophen-2-yl)-[1,3,4]oxadiazol-2-yl]-2,6-dimethyl-phenyl}-propionamide is prepared from Intermediate D5 in analogy to Example 58; LC-MS: $t_R$=1.03 min, [M+1]=456.23.

Example 111

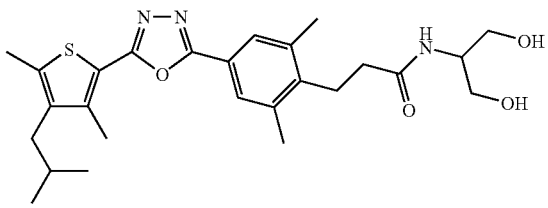

N-(2-Hydroxy-1-hydroxymethyl-ethyl)-3-{4-[5-(4-isobutyl-3,5-dimethyl-thiophen-2-yl)-[1,3,4]oxadiazol-2-yl]-2,6-dimethyl-phenyl}-propionamide is prepared from Intermediate D5 in analogy to Example 58 using 2-amino-propane-1,3-diol; LC-MS: $t_R$=0.97 min, [M+1]=486.27.

Example 112

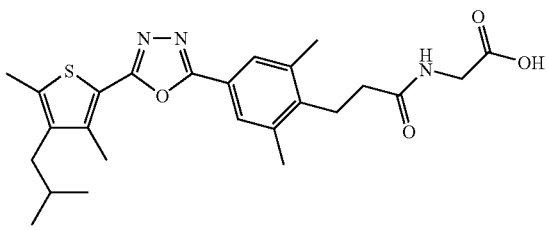

(3-{4-[5-(4-Isobutyl-3,5-dimethyl-thiophen-2-yl)-[1,3,4]oxadiazol-2-yl]-2,6-dimethyl-phenyl}-propionylamino)-acetic acid is prepared from Intermediate D5 in following the procedures given in Examples 67 and 68; LC-MS: $t_R$=1.05 min, [M+1]=470.49; $^1$H NMR (D$_6$-DMSO, 100° C.): δ 0.86 (d, J=6.7 Hz, 6 H), 1.76 (hept, J=6.7 Hz, 1H), 2.23-2.32 (m, 2 H), 2.35 (s, 6 H), 2.37 (s, 3 H), 2.38-2.42 (m, 2 H), 2.45 (s, 3 H), 2.82-2.91 (m, 2 H), 3.73 (s, 2 H), 7.59 (s, 2 H).

Example 113

GTPγS Assay to Determine EC$_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 µM GDP (Sigma, G-7127), 2.5% DMSO (Fluka, 41644), 50 µM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 µl MicroScint20 (Packard Biosciences, order #6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

Table 1 shows the EC$_S$, value of some compounds of the present invention. The EC$_{50}$ values were determined according to the method described above:

TABLE 1

| Compound of Example | EC$_{50}$ [nM] |
|---|---|
| 3 | 5.8 |
| 7 | 8.4 |
| 8 | 7.5 |
| 16 | 5.5 |
| 50 | 2.1 |
| 58 | 7.5 |
| 70 | 1.1 |
| 109 | 0.4 |

Example 114

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Züurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of compounds of the present invention to normotensive male Wistar rats as compared to a group of animals treated with vehicle only.

TABLE 2

| Compound of Example | Lymphocyte counts |
| --- | --- |
| 23 | −73 ± 2 |
| 46 | −77 ± 3 |
| 50 | −93 ± 1 |
| 64 | −66 ± 1 |

The invention claimed is:

1. A compound selected from the group consisting of thiophene compounds of Formula (I),

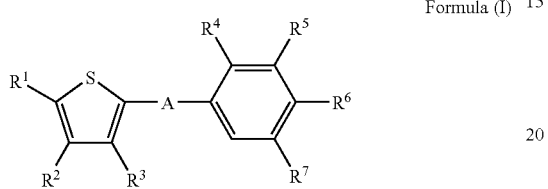

Formula (I)

wherein

A represents

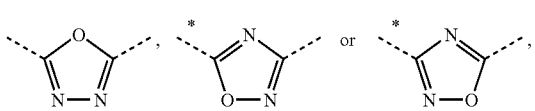

wherein the asterisks indicate the bond that is linked to the thiophene group of Formula (I);

$R^1$ represents hydrogen, methyl, or trifluoromethyl;

$R^2$ represents n-propyl, isobutyl, or cyclopropylmethyl;

$R^3$ represents hydrogen, methyl, trifluoromethyl, ethyl, n-propyl, isopropyl, or isobutyl;

$R^4$ represents hydrogen, $C_{1-4}$-alkyl, methoxy, or halogen;

$R^5$ represents hydrogen, $C_{1-4}$-alkyl, $C_{1-4}$-alkoxy, or halogen;

$R^6$ represents hydroxy-$C_{1-4}$-alkyl, di-(hydroxy-$C_{1-4}$-alkyl)-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$(CH_2)_k$—$(CHR^{65})_p$—$CHR^{66}$—$CONR^{61}R^{62}$, —$(CH_2)_n CH(OH)$—$CH_2$—$NR^{61}R^{62}$, —$(CH_2)_n CH(OH)$—$CH_2$—$NHCOR^{64}$, —$(CH_2)_2 CH(OH)$—$CH_2$—$NHSO_2R^{63}$, —CO—$NHR^{61}$, hydroxy, hydroxy-$C_{2-4}$-alkoxy, di-(hydroxy-$C_{1-4}$-alkyl)-$C_{1-4}$-alkoxy, 1-glyceryl, 2,3-dihydroxypropoxy, 2-hydroxy-3-methoxy-propoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, —$OCH_2$—$CH(OH)$—$CH_2$—$NR^{61}R^{62}$, —$OCH_2$—$CH(OH)$—$CH_2$—$NHCOR^{64}$, —$OCH_2$—$CH(OH)$—$CH_2$—$NHSO_2R^{63}$, —$NR^{61}R^{62}$, —NHCO—$R^{64}$, or —$SO_2NH$—$R^{61}$;

$R^{61}$ represents hydrogen, methyl, ethyl, 2-hydroxyethyl, 2-hydroxy-1-hydroxymethyl-ethyl, 2,3-dihydroxy-propyl, 2-$C_{1-4}$-alkoxyethyl, 3-hydroxypropyl, 3-$C_{1-4}$-alkoxypropyl, 2-aminoethyl, 2-($C_{1-4}$-alkylamino)ethyl, 2-(di-($C_{1-4}$-alkyl)amino)ethyl, carboxymethyl, $C_{1-4}$-alkylcarboxymethyl, 2-carboxyethyl, or 2-($C_{1-4}$-alkylcarboxy)ethyl;

$R^{62}$ represents hydrogen, or methyl;

$R^{63}$ represents methyl, ethyl, 2-hydroxyethyl, 2-methoxyethyl, methylamino, ethylamino, or dimethylamino;

$R^{64}$ represents hydroxymethyl, aminomethyl, methylaminomethyl, dimethylaminomethyl, 2-aminoethyl, or 2-methylamino-ethyl;

$R^{65}$ represents hydrogen;

$R^{66}$ represents hydrogen or hydroxy; and in case $R^{66}$ represents hydroxy, $R^{65}$ may in addition represent hydroxy;

m represents the integer 1 or 2;

n represents 0, 1, or 2;

k represents 0;

p represents 0 or 1; and in case p represents 1, k may in addition represent 1; and $R^7$ represents hydrogen, $C_{1-4}$-alkyl, or halogen;

or a salt thereof.

2. The compound according to claim 1, wherein $R^6$ represents hydroxy -$C_{1-4}$-alkyl, di-(hydroxy-$C_{1-4}$-alkyl)-$C_{1-4}$-alkyl, 2,3-dihydroxypropyl, —$CH_2$—$(CH_2)_n$—$NR^{61}R^{62}$, —$CH_2$—$(CH_2)_n$—$NHCOR^{64}$, —$CH_2$—$(CH_2)_n$—$NHSO_2R^{63}$, —$(CH_2)_k$—$(CHR^{65})_p$—$CHR^{66}$—$CONR^{61}R^{62}$, —$(CH_2)_n CH(OH)$—$CH_2$—$NR^{61}R^{62}$, —$(CH_2)_n CH(OH)$—$CH_2$—$NHCOR^{64}$, —$(CH_2)_n CH(OH)$—$CH_2$—$NHSO_2R^{63}$, —CO—$NHR^{61}$, hydroxy, hydroxy-$C_{2-4}$-alkoxy, di-(hydroxy-$C_{1-4}$-alkyl)-$C_{1-4}$-alkoxy, 1-glyceryl, 2-hydroxy-3-methoxy-propoxy, —$OCH_2$—$(CH_2)_m$—$NR^{61}R^{62}$, —$OCH_2$—$(CH_2)_m$—$NHCOR^{64}$, —$OCH_2$—$(CH_2)_m$—$NHSO_2R^{63}$, —$OCH_2$—$CH(OH)$—$CH_2$—$NR^{61}R^{62}$, —$OCH_2$—$CH(OH)$—$CH_2$—$NHCOR^{64}$, —$OCH_2$—$CH(OH)$—$CH_2$—$NHSO_2R^{63}$, —$NR^{62}R^{62}$, —NHCO—$R^{64}$, or —$SO_2NH$—$R^{61}$.

3. The compound according to claim 1, wherein A represents

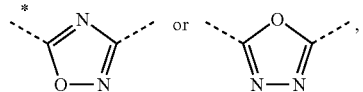

wherein the asterisk indicates the bond that is linked to the thiophene group of Formula (I).

4. The compound according to claim 1, wherein A represents

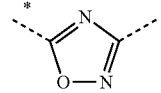

wherein the asterisk indicates the bond that is linked to the thiophene group of Formula (I).

5. The compound according to claim 1, wherein A represents

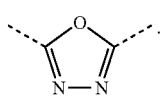

6. The compound according to claim 1, wherein $R^1$ represents hydrogen or methyl.

7. The compound according to claim 1, wherein $R^1$ represents hydrogen.

8. The compound according to claim 1, wherein $R^1$ represents a methyl.

9. The compound according to claim 1, wherein $R^2$ represents an isobutyl.

10. The compound according to claim 1, wherein $R^3$ represents methyl, ethyl, n-propyl, or isobutyl.

11. The compound according to claim 1, wherein $R^3$ represents a methyl.

12. The compound according to claim 1, wherein $R^4$ represents methoxy, and $R^5$ and $R^7$ represent hydrogen, or wherein $R^4$ represents hydrogen and $R^5$ represents methyl, ethyl, or methoxy and $R^7$ represents methyl, ethyl or halogen.

13. The compound according to claim 1, wherein $R^4$ represents a methoxy, and $R^5$ and $R^7$ represent hydrogen.

14. The compound according to claim 1, wherein $R^4$ represents hydrogen, and $R^5$ and $R^7$ represent a methyl.

15. The compound according to claim 1, wherein $R^4$ represents hydrogen, and $R^5$ and $R^7$ represent an ethyl.

16. The compound according to claim 1, wherein $R^4$ represents hydrogen, $R^5$ represents a methyl, and $R^7$ represents an ethyl.

17. The compound according to claim 1, wherein $R^4$ represents hydrogen, $R^5$ represents a methoxy, and $R^7$ represents a chloro atom.

18. The compound according to claim 1, wherein $R^4$ represents hydrogen, $R^5$ represents a methyl, and $R^7$ represents a chloro atom.

19. The compound according to claim 1, wherein $R^6$ represents —$(CH_2)_k$—$(CHR^{65})_p$—$CHR^{66}$—$CONR^{61}R^{62}$.

20. The compound according to claim 1, wherein $R^6$ represents —$(CH_2)_k$—$(CHR^{65})_p$—$CHR^{66}$—$CONR^{61}R^{62}$, wherein k represents 0, p represents 1, and $R^{65}$ and $R^{66}$ represent hydrogen.

21. The compound according to claim 1, wherein $R^6$ represents —$OCH_2$—$CH(OH)$—$CH_2$—$NHCOR^{64}$.

22. The compound according to claim 1, wherein $R^6$ represents —$OCH_2$—$CH(OH)$—$CH_2$—$NHCOR^{64}$, wherein $R^{64}$ represents hydroxymethyl.

23. The compound according to claim 1, wherein $R^6$ represents 2,3-dihydroxypropoxy.

24. The compound according to claim 1, wherein A represents

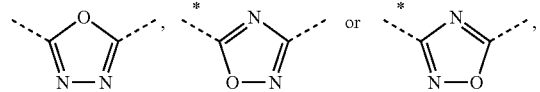

wherein the asterisks indicate the bond that is linked to the thiophene group of Formula (I);
$R^1$ represents hydrogen or methyl;
$R^2$ represents n-propyl or isobutyl;
$R^3$ represents hydrogen, methyl, ethyl, n-propyl, isopropyl, or isobutyl;
$R^4$ represents hydrogen or methoxy;
$R^5$ represents hydrogen, $C_{1-4}$-alkyl, or $C_{1-4}$-alkoxy;
$R^6$ represents hydroxy; hydroxy-$C_{2-4}$-alkoxy; 2,3-dihydroxypropoxy; —$OCH_2$—$(CH_2)_m$—$NHCOR^{64}$; —$OCH_2$—$CH(OH)$—$CH_2$—$NR^{61}R^{62}$; —$OCH_2$—$CH(OH)$—$CH_2$—$NHCOR^{64}$; —$OCH_2$—$CH(OH)$—$CH_2$—$NHSO_2R^{63}$; or —$CH_2$—$CH_2$—$CONHR'$, wherein R' is 2-hydroxyethyl, 2-hydroxy-1-hydroxymethyl-ethyl, hydroxycarbonylmethyl, or methoxycarbonylmethyl;
$R^{61}$ and $R^{62}$ represent hydrogen;
$R^{63}$ represents methyl;
$R^{64}$ represents hydroxymethyl, methylaminomethyl, or 2-methylamino-ethyl;

m represents the integer 1 or 2; and
$R^7$ represents hydrogen, $C_{1-4}$-alkyl, or halogen.

25. The compound according to claim 1, wherein $R^1$ represents hydrogen or methyl, $R^2$ represents isobutyl, $R^3$ represents hydrogen or methyl, $R^4$ represents hydrogen, $R^5$ and $R^7$ represent $C_{1-4}$-alkyl, $R^6$ represents —$OCH_2$—$CH(OH)$—$CH_2$-$NHCOR^{64}$, and A represents

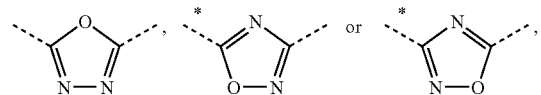

wherein the asterisks indicate the bond that is linked to the thiophene group of Formula (I).

26. The compound according to claim 1 selected from the group consisting of:
2-hydroxy-N-(2-hydroxy-3-{4-[5(4-isobutyl-5-methyl-thiophen-2-yl)-[1,2,4]oxadiazol -3-yl]-2,6-dimethyl-phenoxy}-propyl)-acetamide;
N-(3-{2-ethyl-4-[5-(4-isobutyl-5-methyl-thiophen-2-yl)-[1,2,4]oxadiazol-3-yl]-6-methyl -phenoxy}-2-hydroxy-propyl)-2-hydroxy-acetamide;
N-(3-{2-ethyl-4-[5-(4-isobutyl-3-methyl-thiophen-2-yl)-[1,2,4]oxadiazol-3-yl]-6-methyl -phenoxy}-2-hydroxy-propyl)-2-hydroxy-acetamide;
2-hydroxy-N-(2-hydroxy-3-{4-[5-(4-isobutyl-3-methyl-thiophen-2-yl)-[1,2,4]oxadiazol -3-yl]-2,6-dimethyl-phenoxy}-propyl)-acetamide;
N-(2-hydroxy-3-{4-[5-(4-isobutyl-3-methyl-thiophen-2-yl)-[1,2,4]oxadiazol-3-yl]-2,6-dimethyl-phenoxy}-propyl)-2-methylamino-acetamide;
2-hydroxy-N-(3-{4-[5-(4-isobutyl-3-methyl-thiophen-2-yl)-[1,2,4]oxadiazol-3-yl]-2,6-dimethyl-phenoxy}-propyl)-acetamide;
3-{4-[5-(4-isobutyl-3-methyl-thiophen-2-yl)-[1,3,4]oxadiazol-2-yl]-2,6-dimethyl -phenoxy}-propane-1,2-diol;
3-{4-[5-(3-ethyl-4-isobutyl-thiophen-2-yl)-[1,3,4]oxadiazol-2-yl]-2,6-dimethyl -phenoxy}-propane-1,2-diol;
3-{4-[5-(4-isobutyl-3-propyl-thiophen-2-yl)-[1,3,4]oxadiazol-2-yl]-2,6-dimethyl -phenoxy}-propane-1,2-diol;
3-{4-[5-(3,4-diisobutyl-thiophen-2-yl)-[1,3,4]oxadiazol-2-yl]-2,6-dimethyl-phenoxy}-propane-1,2-diol;
2-hydroxy-N-(2-hydroxy-3-{4-[5-(4-isobutyl-3-methyl-thiophen-2-yl)-[1,3,4]oxadiazol -2-yl]-2,6-dimethyl-phenoxy}-propyl)-acetamide;
N-(3-{4[5-(3-ethyl-4-isobutyl-thiophen-2-yl)-[1,3,4]oxadiazol-2-yl]-2,6-dimethyl -phenoxy}-2-hydroxy-propyl)-2-hydroxy-acetamide;
2-hydroxy-N-(2-hydroxy-3-{4-[5-(4-isobutyl-3-propyl-thiophen-2-yl)-[1,3,4]oxadiazol -2-yl]-2,6-dimethyl-phenoxy}-propyl)-acetamide;
N-(3-{4[5-(3,4-diisobutyl-thiophen-2-yl)-[1,3,4]oxadiazol-2-yl]-2,6-dimethyl-phenoxy}-2-hydroxy-propyl)-2-hydroxy-acetamide;
3-{4-[5-(4-isobutyl-5-methyl-thiophen-2-yl)-[1,2,4]oxadiazol-3-yl]-3-methoxy -phenoxy}-propane-1,2-diol;
2-hydroxy-N-(2-hydroxy-3-{4-[5-(4-isobutyl-5-methyl-thiophen-2-yl)-[1,2,4]oxadiazol -3-yl]-3-methoxy-phenoxy}-propyl)-acetamide; and
2-hydroxy-N-(2-hydroxy-3-{4-[5-(4-isobutyl-3,5-dimethyl-thiophen-2-yl) -[1,2,4]oxadiazol-3-yl]-2,6-dimethyl-phenoxy}-propyl)-acetamide;
or a salt thereof.

27. The compound according to claim 1 selected from the group consisting of:
- N—((S)-3-{2,6-diethyl-4-[5-(4-isobutyl-5-methyl-thiophen-2-yl)-[1,2,4]oxadiazol-3-yl]-phenoxy}-2-hydroxy-propyl)-2-hydroxy-acetamide;
- N—((S)-3-{2-chloro-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide;
- N—((R)-3-{2-chloro-4-[5-(4-isobutyl-5-methyl-thiophen-2-yl)-[1,2,4]oxadiazol-3-yl]-6-methyl-phenoxy}-2-hydroxy-propyl)-2-hydroxy-acetamide;
- 3-{2-ethyl-4[5-(4-isobutyl-5-methyl-thiophen-2-yl)-[1,2,4]oxadiazol-3-yl]-6-methyl-phenyl}-N-(2-hydroxy-ethyl)-propionamide;
- 2-hydroxy-N—((S)-2-hydroxy-3-{4-[5-(4-isobutyl-5-methyl-thiophen-2-yl)-[1,3,4]oxadiazol-2-yl]-2,6-dimethyl-phenoxy}-propyl)-acetamide;
- 2-hydroxy-N—((R)-2-hydroxy-3-{4-[5-(4-isobutyl-5-methyl-thiophen-2-yl)-[1,3,4]oxadiazol-2-yl]-2,6-dimethyl-phenoxy}-propyl)-acetamide;
- N—((R)-3-{2-ethyl-4-[5-(4-isobutyl-5-methyl-thiophen-2-yl)-[1,3,4]oxadiazol-2-yl]-6-methyl-phenoxy}-2-hydroxy-propyl)-2-hydroxy-acetamide;
- N—((S)-3-{2-ethyl-4-[5-(4-isobutyl-5-methyl-thiophen-2-yl)-[1,3,4]oxadiazol-2-yl]-6-methyl-phenoxy}-2-hydroxy-propyl)-2-hydroxy-acetamide;
- N-(2-hydroxy-1-hydroxymethyl-ethyl)-3-{4-[5-(4-isobutyl-5-methyl-thiophen-2-yl)-[1,3,4]oxadiazol-2-yl]-2,6-dimethyl-phenyl}-propionamide;
- 2-hydroxy-N—((S)-2-hydroxy-3-{4-[5-(4-isobutyl-3-methyl-thiophen-2-yl)-[1,2,4]oxadiazol-3-yl]-2,6-dimethyl-phenoxy}-propyl)-acetamide;
- 2-hydroxy-N—((R)-2-hydroxy-3-{4-[5-(4-isobutyl-3-methyl-thiophen-2-yl)-[1,2,4]oxadiazol-3-yl]-2,6-dimethyl-phenoxy}-propyl)-acetamide;
- N—((S)-3-{2-ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;
- N—((R)-3-{2-ethyl-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;
- N—((S)-3-{2-chloro-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;
- N—((R)-3-{2-chloro-4-[5-(4-isobutyl-3-methyl-thiophen-2-yl)-[1,2,4]oxadiazol-3-yl]-6-methyl-phenoxy}-2-hydroxy-propyl)-2-hydroxy-acetamide;
- N—((S)-3-{2,6-diethyl-4-[5-(4-isobutyl-3-methyl-thiophen-2-yl)-[1,2,4]oxadiazol-3-yl]-phenoxy}-2-hydroxy-propyl)-2-hydroxy-acetamide;
- N—((R)-3-{2,6-diethyl-4-[5-(4-isobutyl-3-methyl-thiophen-2-yl)-[1,2,4]oxadiazol-3-yl]-phenoxy}-2-hydroxy-propyl)-2-hydroxy-acetamide;
- N—((S)-3-{2-ethyl-4-[5-(4-isobutyl-3-methyl-thiophen-2-yl)-[1,3,4]oxadiazol-2-yl]-6-methyl-phenoxy}-2-hydroxy-propyl)-2-hydroxy-acetamide;
- N—((R)-3-{2-ethyl-4-[5-(4-isobutyl-3-methyl-thiophen-2-yl)-[1,3,4]oxadiazol-2-yl]-6-methyl-phenoxy}-2-hydroxy-propyl)-2-hydroxy-acetamide;
- 2-hydroxy-N—((S)-2-hydroxy-3-{4-[3-(4-isobutyl-3-methyl-thiophen-2-yl)-[1,2,4]oxadiazol-5-yl]-2,6-dimethyl-phenoxy}-propyl)-acetamide;
- 2-hydroxy-N—((R)-2-hydroxy-3-{4-[3-(4-isobutyl-3-methyl-thiophen-2-yl)-[1,2,4]oxadiazol-5-yl]-2,6-dimethyl-phenoxy}-propyl)-acetamide;
- N—((S)-3-{2-chloro-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide;
- N—((R)-3-{2-chloro-4-[5-(4-isobutyl-3,5-dimethyl-thiophen-2-yl)-[1,2,4]oxadiazol-3-yl]-6-methyl-phenoxy}-2-hydroxy-propyl)-2-hydroxy-acetamide;
- 2-hydroxy-N—((S)-2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide;
- 2-hydroxy-N—((R)-2-hydroxy-3-{4-[5-(4-isobutyl-3,5-dimethyl-thiophen-2-yl)-[1,3,4]oxadiazol-2-yl]-2,6-dimethyl-phenoxy}-propyl)-acetamide;
- N—((R)-3-{2-ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide; and
- N—((S)-3-{2-ethyl-4-[5-(4-isobutyl-3,5-dimethyl-thiophen-2-yl)-[1,3,4]oxadiazol-2-yl]-6-methyl-phenoxy}-2-hydroxy-propyl)-2-hydroxy-acetamide;

or a salt thereof.

28. A pharmaceutical composition comprising a compound according to claim 1, or a pharmaceutically acceptable salt thereof and a pharmaceutically acceptable carrier.

29. A compound selected from the group consisting of thiophenes of Formula (III)

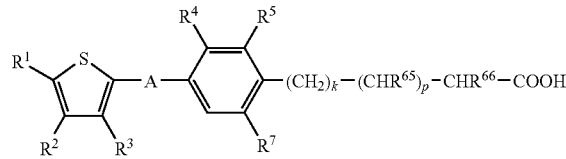

Formula (III)

A represents

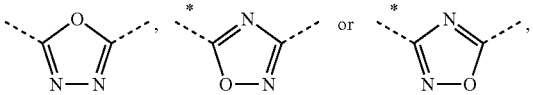

wherein the asterisks indicate the bond that is linked to the thiophene group of Formula (I);

$R^1$ represents hydrogen, methyl, or trifluoromethyl;
$R^2$ represents n-propyl, isobutyl, or cyclopropylmethyl;
$R^3$ represents hydrogen, methyl, trifluoromethyl, ethyl, n-propyl, isopropyl, or isobutyl;
$R^4$ represents hydrogen, $C_{1-4}$-alkyl, methoxy, or halogen;
$R^5$ represents hydrogen, $C_{1-4}$-alkyl, $C_{1-4}$-alkoxy, or halogen;
$R^{65}$ represents hydrogen;
$R^{66}$ represents hydrogen or hydroxy; and
in case $R^{66}$ represents hydroxy, $R^{65}$ may in addition represent hydroxy;
k represents 0;
p represents 0 or 1; and
in case p represents 1, k may in addition represent 1; and
$R^7$ represents hydrogen, $C_{1-4}$-alkyl, or halogen;
or a salt thereof.

* * * * *

UNITED STATES PATENT AND TRADEMARK OFFICE
CERTIFICATE OF CORRECTION

PATENT NO. : 8,003,800 B2
APPLICATION NO. : 12/160520
DATED : August 23, 2011
INVENTOR(S) : Martin Bolli et al.

Page 1 of 1

It is certified that error appears in the above-identified patent and that said Letters Patent is hereby corrected as shown below:

Column 79, line 45, please replace " $-CH_2-(CH_2)_n-NR^{61}R^{62}$ " with "$-CH_2-(CH_2)_n-NR^{61}R^{62}$";

Column 79, line 49, please replace "$-(CH_2)_2CH(OH)-CH_2-NHSO_2R^{63}$" with "$-(CH_2)_nCH(OH)-CH_2-NHSO_2R^{63}$";

Column 80, line 29, please replace "$-NR^{62}R^{62}$" with "$-NR^{61}R^{62}$"

Signed and Sealed this
Sixth Day of November, 2012

David J. Kappos
*Director of the United States Patent and Trademark Office*